(12) United States Patent
Flynn et al.

(10) Patent No.: US 9,248,131 B2
(45) Date of Patent: Feb. 2, 2016

(54) AQUAPORIN MODULATORS AND METHODS OF USING THEM FOR THE TREATMENT OF EDEMA AND FLUID IMBALANCE

(71) Applicant: THE ARIZONA BOARD OF REGENTS ON BEHALF OF THE UNIVERSITY OF ARIZONA, Tucson, AZ (US)

(72) Inventors: Gary A. Flynn, Oro Valley, AZ (US); Andrea J. Yool, South Australia (AU); Elton Rodrigues Migliati, Queen Creek, AZ (US); Leslie S. Ritter, Tucson, AZ (US)

(73) Assignee: ARIZONA BOARD OF REGENTS ON BEHALF OF THE UNIVERSITY OF ARIZONA, Phoenix, AZ (US)

( * ) Notice: Subject to any disclaimer, the term of this patent is extended or adjusted under 35 U.S.C. 154(b) by 0 days.

(21) Appl. No.: 14/678,818

(22) Filed: Apr. 3, 2015

(65) Prior Publication Data
US 2015/0224108 A1    Aug. 13, 2015

Related U.S. Application Data

(60) Continuation of application No. 14/299,999, filed on Jun. 9, 2014, which is a division of application No. 13/970,212, filed on Aug. 19, 2013, now Pat. No. 8,835,491, which is a continuation of application No. 13/048,676, filed on Mar. 15, 2011, now abandoned, which is a division of application No. 11/925,708, filed on Oct. 26, 2007, now Pat. No. 7,906,555.

(60) Provisional application No. 60/854,618, filed on Oct. 26, 2006.

(51) Int. Cl.
| | |
|---|---|
| *A61K 31/54* | (2006.01) |
| *A61K 31/24* | (2006.01) |
| *A61K 31/495* | (2006.01) |
| *A61K 31/5375* | (2006.01) |
| *A61K 31/341* | (2006.01) |
| *A61K 31/4402* | (2006.01) |
| *A61K 31/4409* | (2006.01) |
| *A61K 31/443* | (2006.01) |
| *A61K 31/496* | (2006.01) |
| *A61K 31/196* | (2006.01) |
| *A61K 31/4406* | (2006.01) |
| *C07C 311/39* | (2006.01) |
| *C07D 213/40* | (2006.01) |
| *C07D 213/75* | (2006.01) |
| *C07D 239/91* | (2006.01) |
| *C07D 279/12* | (2006.01) |
| *C07D 307/52* | (2006.01) |
| *C07C 311/16* | (2006.01) |
| *C07D 213/16* | (2006.01) |
| *C07D 241/04* | (2006.01) |
| *C07D 265/30* | (2006.01) |
| *C07D 307/36* | (2006.01) |
| *C07D 405/06* | (2006.01) |
| *C07D 405/12* | (2006.01) |
| *C07D 407/12* | (2006.01) |

(52) U.S. Cl.
CPC ............... *A61K 31/54* (2013.01); *A61K 31/196* (2013.01); *A61K 31/24* (2013.01); *A61K 31/341* (2013.01); *A61K 31/4402* (2013.01); *A61K 31/443* (2013.01); *A61K 31/4406* (2013.01); *A61K 31/4409* (2013.01); *A61K 31/495* (2013.01); *A61K 31/496* (2013.01); *A61K 31/5375* (2013.01); *C07C 311/16* (2013.01); *C07C 311/39* (2013.01); *C07D 213/16* (2013.01); *C07D 213/40* (2013.01); *C07D 213/75* (2013.01); *C07D 239/91* (2013.01); *C07D 241/04* (2013.01); *C07D 265/30* (2013.01); *C07D 279/12* (2013.01); *C07D 307/36* (2013.01); *C07D 307/52* (2013.01); *C07D 405/06* (2013.01); *C07D 405/12* (2013.01); *C07D 407/12* (2013.01)

(58) Field of Classification Search
None
See application file for complete search history.

(56) References Cited

U.S. PATENT DOCUMENTS

| | | | | |
|---|---|---|---|---|
| 3,565,920 | A | 2/1971 | Werner | 558/399 |
| 3,839,321 | A | 10/1974 | Weinstock | 549/426 |
| 3,971,819 | A | 7/1976 | Feit | 260/465 |
| 6,242,493 | B1 | 6/2001 | Gareau et al. | 514/569 |
| 7,906,555 | B2 * | 3/2011 | Flynn et al. | 514/602 |
| 8,835,491 | B2 * | 9/2014 | Flynn et al. | 514/471 |
| 2004/0213782 | A1 | 10/2004 | Wax | 424/143.1 |

(Continued)

FOREIGN PATENT DOCUMENTS

| | | | | |
|---|---|---|---|---|
| EP | 0 008 433 | | 3/1980 | ........... C07D 263/10 |
| WO | WO 90/15600 | | 12/1990 | ............. A61K 31/18 |

(Continued)

OTHER PUBLICATIONS

Stephen W. Wright, et al. "A Convenient Preparation of Heteroarly Sulfonamides and Sulfonyl Flourides from Heneroaryl Thiols" JOC Article, Journal of Organic Chemistry, American Chemical Society, vol. 71, No. 3, Feb. 3, 2006, pp. 1080-1084.

(Continued)

*Primary Examiner* — Kristin Vajda
(74) *Attorney, Agent, or Firm* — Hayes Soloway P.C.

(57) ABSTRACT

Compounds, including 3-carboxy aryl sulfonamide compounds, which agonize or antagonize aquaporin channels and methods of using them to treat disorders or diseases mediated by aquaporins.

4 Claims, 8 Drawing Sheets

(56) References Cited

U.S. PATENT DOCUMENTS

| | | | |
|---|---|---|---|
| 2005/0187280 A1 | 8/2005 | Minnich et al. | 514/408 |
| 2005/0288324 A1 | 12/2005 | Blume et al. | 514/307 |
| 2006/0089350 A1 | 4/2006 | Hochman et al. | 514/223.5 |
| 2007/0213391 A1 | 9/2007 | Minnich et al. | 514/427 |

FOREIGN PATENT DOCUMENTS

| | | | |
|---|---|---|---|
| WO | WO 98/27081 | 6/1998 | A61K 31/4025 |
| WO | WO 01/96889 | 12/2001 | H02H 3/16 |
| WO | WO 02/096889 | 12/2002 | C07D 405/06 |
| WO | WO 2005/082350 | 9/2005 | A61K 31/34 |

OTHER PUBLICATIONS

Examination Report dated May 18, 2013 as received in the corresponding Indian Patent Application No. 2984/DELNP/2009.

Communication pursuant to Article 94(3) EPC dated Feb. 15, 2013 as received in the corresponding European Patent Application No. 07 863 575.2.-1451.

Office Action dated Jan. 22, 2013 as received in Japanese Patent Application No. 2009-534902 (English Translation Only).

Examination Report as received in corresponding Israeli Patent Application No. 198439 2013.

First Office Action as received in Japanese Patent Application No. 2009-534902 dated Jan. 22, 2013.

Jpn. Pat. Appln. KOKAI Publication No. 49-126647 w/ English translation 1974.

J. Starklints et al. "Urinary excretion of aquaporin-2 after furosemide and felodipine in health humans" Scandinavian Journal of Clinical and Laboratory Investigation, 2005, 65 (3), 249-261.

Tetrahedron, 1993, 49 (41), 9353-9372.

Hartmut Lüddens, et al., "Structure-activity relationship of furosemide-derived compounds as antagonists of cerebellum-specific $GABA_A$ receptors," European Journal of Pharmacology, Mar. 1, 1998, 344 (2/3), XP 2128304, pp. 269-277.

Karl Sturm, et al., "Synthesen von 5-Sulfamayl-anthranilsaure-derivaten," Chemische Berichte, Jan. 1, 1966, 99(1), XP 2203298, 328-344.

De-Chun Zhang, et al., Three Isostructural Furosemide Prodrugs, Acta Crystallographica Section C, 1998 54 (12), 1911-1915.

Jpn. Pat. Appin. KOKAI Publication No. 55-036491 2013.

Japan Patent Application, KOKOKU Publication No. 49-039976 1974.

Japan Patent Application No. 2006-154063 (Japan Patent Application, KOKAI Publication No. 2007-320920 w/English Abstract).

Japanese Patent Application No. 2008-536698 (International Publication No. 2007/047447) 2008.

Office Action as received in the corresponding European Patent Application No. 07 863 575.2.-1211 dated. Jun. 27, 2012.

Extended European Search Report issued May 13, 2011, in Patent Application No. 07863575.2.

Supplementary European Search Report issued May 31, 2011, in Patent Application No. 07863575.2.

Helmut Vorbriiggen, et al., "A Simple Synthesis of Delta<2>-Oxazolines, Delta <2>-Oxazines, Delta <2>-Thiazolines and 2-Substituted Benzoxazoles," Tetrahedron, vol. 49, No. 41, XP 26636705, Jan. 1, 1993, pp. 9353-9372.

Leopoldo Suescun, et al., "Three Isostructural Furosemide Prodrugs," ACTA Crystallographica, Section C, Crystal Structure Communications, vol. 54, No. 12, XP 872052, Jan. 1, 1998, pp. 1911-1915.

Official Action issued in related U.S. Appl. No. 11/925,708 dated Feb. 11, 2009 (10 pgs).

Official Action issued in related U.S. Appl. No. 11/925,708 dated Jul. 7, 2009 (9 pgs).

Official Action issued in related U.S. Appl. No. 11/925,708 dated Mar. 16, 2010 (7 pgs).

Notice of Allowance issued in related U.S. Appl. No. 11/925,708 dated Nov. 1, 2010 (7 pgs).

Official Action issued in related U.S. Appl. No. 13/048,676 dated Jul 19, 2011 (5 pgs).

Official Action issued in related U.S. Appl. No. 13/048,676 dated Nov. 23, 2011 (7 pgs).

Official Action issued in related U.S. Appl. No. 13/048,676 dated Jul. 18, 2012 (9 pgs).

Official Action issued in related U.S. Appl. No. 13/970,212 dated Mar. 17, 2014 (7 pgs).

Official Action issued in related U.S. Appl. No. 13/970,212 dated Jan. 7, 2014 (9 pgs).

Notice of Allowance issued in related U.S. Appl. No. 13/970,212 dated May 1, 2014 (7 pgs).

Official Action issued in related U.S. Appl. No. 14/299,999 dated Jan. 5, 2015 (14 pgs).

Official Action issued in related U.S. Appl. No. 14/299,999 dated Aug. 20, 2014 (5 pgs).

* cited by examiner control bumetanide control bumetanide

AQUAPORIN MODULATORS AND METHODS OF USING THEM FOR THE TREATMENT OF EDEMA AND FLUID IMBALANCE

CROSS-REFERENCE TO RELATED APPLICATIONS

This application is a Continuation of U.S. application Ser. No. 14/299,999, filed Jun. 9, 2014, which is a Divisional of U.S. application Ser. No. 13/970,212, filed Aug. 19, 2013, now U.S. Pat. No. 8,835,491, which is a Continuation of U.S. application Ser. No. 13/048,676, filed Mar. 15, 2011, now abandoned, which is a Divisional of U.S. application Ser. No. 11/925,708, filed Oct. 26, 2007, now U.S. Pat. No. 7,906,555, which claims priority under 35 U.S.C. 119(e) and 120 to U.S. Provisional Application No. 60/854,618, filed Oct. 26, 2006, the entire contents of which are hereby incorporated by reference.

STATEMENT REGARDING FEDERALLY SPONSORED RESEARCH OR DEVELOPMENT

This invention was made with government support under Contract Numbers R01 GM059986 and R01 NR005208 awarded by the National Institutes of Health. The government has certain rights in the invention.

BACKGROUND OF THE INVENTION

1. Field of the Invention

Compounds that modulate water transport by aquaporin channels in cell membranes and methods of using these compound to treat diseases and disorders associated with aquaporin activity.

2. Description of the Related Art

Aquaporins (AQPs) represent a diverse family of membrane proteins found in prokaryotes and eukaryotes (Reizer et al., 1993; Hohmann et al., 2000; King et al., 2004). Aquaporin channels have a well known role for promoting transmembrane diffusion of water (Agre et al., 1993), as well a other molecules including ions, gases, and small organic compounds (Yool and Stamer, 2002). Aquaporins are encoded by members of the major intrinsic protein (MIP) gene family. In mammals, there are at least 12 classes of aquaporins (AQP0 to AQP11) that exhibit tissue-specific patterns of expression (Nielsen et al., 2002). Aquaporin channels play roles in various physiological process and have been implicated in pathophysiological conditions involving water imbalance.

AQP1 is a widely expressed water channel found in the basolateral and apical plasma membranes of the proximal tubules, the descending limb of the loop of Henle, and in the descending portion of the vasa recta of the kidney. It is also present in red blood cells, vascular endothelium, the gastrointestinal tract, sweat glands, and lungs.

AQP4 is expressed abundantly throughout the central nervous system, where it is concentrated in the perivascular endfeet of astroglial cells that surround blood vessels and maintain the integrity of the blood-brain barrier, suggesting an important role in the regulation of brain water balance (Nagelhus et al., 1998; Rash et al., 1998). Colocalization of AQP4 in astroglial endfeet occurs with $K_{ir}1.4$ (inward rectifier) and $K_{Ca}$ ($Ca^{+2}$-activated) potassium channels. AQP4 may be part of a complex organization of proteins that control salt and water influx (Price et al., 2002). Activation of protein kinase C (PKC) stimulates phosphorylation of AQP4 at serine 180 (Zelenina et al., 2002), and causes dose-dependent inhibition of water permeability. Levels of AQP4 expression also are influenced by protein kinase C (Yamamoto et al., 2001; (Han et al., 1998)), bradykinin (Monti et al., 2001), vasopressin (Niermann et al., 2001), and ischemia-related genes (Nicchia et al., 2003), and are massively upregulated in tumor-associated reactive astrocytes (Saadoun et al., 2002).

Verkman and colleagues (Manley et al., 2000) compared the effects of water intoxication and permanent stroke in wild type (+/+) and AQP4 knockout (−/−) mice. Water intoxication was imposed by giving mice intraperitoneal injections of distilled water equal to 20% of body weight. Outcomes focused on mortality, observed neurological deficits, and electron microscopic analyses of brain ultrastructure. Astrocytic endfoot areas in ten randomly selected micrographs were measured from wild-type and AQP4 deficient mice. The lower water content in brain tissue and the reduced astrocytic swelling in the AQP4−/− mice were consistent with improved neurological deficit scores and substantially better survival as compared with the AQP4+/+ mice.

Permanent middle cerebral artery (MCA) occlusion also was tested in AQP+/+ and AQP4−/− mice (n=10 per group). The measured outcomes at 24 h were hemisphere size and neurological deficits (FIG. 1). Significantly greater hemispheric enlargement from brain edema occurred in wild type (FIG. 1A). AQP4+/+ mice also had significantly higher (worse) neurological deficit scores as compared with the AQP4−/− mice (FIG. 1B). Manley and colleagues suggested that the reduced brain edema in AQP4-deficient mice indicates "the AQP4 water channel is a potential target for drug discovery."

AQP9 may also influence brain edema. It is permeable to water and small solutes (urea, glycerol), and is expressed in brain glial cells as well as in liver, spleen and other organs (Badaut et al., 2001; Badaut et al., 2002; Elkjaer et al., 2000; Nicchia et al., 2001). AQP9 is present in cell bodies and processes of astrocytes in contact with brain vessels and fluid compartments. In contrast with AQP4, AQP9 staining is not polarized on astrocytic endfeet (Badaut et al., 2004).

Edema results from many clinical conditions including several neurological conditions or pulmonary conditions. A major unmet medical need is treatment of edema associated with stroke. Stroke, as the third leading cause of death, is a devastating disease affecting more than 700,000 people in the United States each year. The extent of brain edema is a major determinant of patient survival after a stroke event (Dirnagl et al., 1999; Taylor et al., 1996). For progressive edema due to middle cerebral artery occlusion, mortality approaches 80% (Ayata and Ropper, 2002). The propensity of ischemic brain tissue to develop edema remains the major cause of death in patients with large infarctions, particularly within the middle cerebral artery territory and cerebellum involved in 15-20% of all strokes (Hacke et al., 1996). An important problem recognized in the prior art was the identification of molecular targets for intervention in the edema process. However, clinically acceptable strategies for management of ischemic brain edema have remained elusive, and available treatments are often of limited value for patients with massive edema.

Brain edema is classified as vasogenic (movement of water and solutes across the blood brain barrier), or cytotoxic (osmotic swelling of cells in the affected area) (Fishman, 1975; Klatzo, 1967). Cytotoxic edema correlates with initial infarct size, and vasogenic edema contributes to the delayed risk-prone processes of brain swelling (FIG. 2). Astrocytes play a role in both processes. Astrocyte endfeet covering the abluminal capillary surface promote maintenance of intercellular tight junctions between endothelial cells that create the blood-brain barrier (Huber et al., 2001). Blood-brain barrier disruption after ischemia involves altered transport, opening of paracellular pathways, and physical disruption of astrocyte-endothelial junctions (Sun and O'Donnell, 1996; Venero et al., 2001). Pericapillary astrocyte endfeet are the first cellular elements to swell during brain ischemia (Dodson et al., 1977), a process thought to result from uptake of extracellular $K^+$, $Cl^-$, and $Na^+$ and the osmotic flux of water (Su et al., 2002), promoting a progressive cascade of pathology.

Aquaporin expression has been associated with the formation of brain edema in studies comparing edema between mice expressing AQP4 and knockout mice not expressing AQP4. Less hemispheric enlargement was observed in knock out mice (FIG. 1A) and neurological scores of knockout mice improved (FIG. 1B), see (Manley et al., 2004). In addition, the selective removal of perivascular AQP4 by β-syntrophin deletion has been shown to delay the buildup of brain edema (assessed by Diffusion-weighted MRI) following water intoxication, despite the presence of a normal complement of endothelial AQP4 (Amiry-Moghaddarn et al., 2006).

Moreover, a significant positive correlation between AQP4 mRNA expression and blood brain barrier (BBB) permeability after experimental cerebral hemorrhage in rats has been observed and these changes are consistent with observed increases in cerebral edema. Other results associate the expression of AQP4 with edema and blood brain permeability (Teng et al., 2006; Chen et al., 2006). Inflammation related edema is also associated with AQP4. Cysteinyl leukotrienes (including LTC4, LTD4, and LTE4) are potent inflammatory mediators that can induce brain-blood barrier (BBB) disruption and brain edema. LTD4 has been shown to affect brain edema in two ways; the CysLT1 receptor mediates vasogenic edema while CysLT2 receptor may mediate cytotoxic edema via up-regulating AQP4 expression (Wang et al., 2006).

Brain edema is associated with a variety of infectious diseases of the brain. In one study, *Sreptococcus pneumoniae* was injected into cerebrospinal fluid (CSF) in wild type and AQP4 null mice. AQP4 protein was found to be strongly up-regulated as a result of meningitis, with an approximately 5-fold increase in water permeability (Pf) across the blood-brain barrier observed compared to non-infected wild type mice (Papadopoulos, et al., Journal of Biological Chemistry (2005), 280(14), 13906-13912. Conversely, other have demonstrated a protective effect of AQP4 on brain swelling in bacterial abscess, suggesting that AQP4 induction may reduce vasogenic edema associated with cerebral infection (Bloch, et al., Journal of Neurochemistry (2005), 95(1), 254-262).

The expression of mRNA for AQP1 and AQP4 was analyzed in a well-established mice model that simulates encephalitis caused by the human Herpes simplex virus encephalitis (HSVE). This study is consistent with a significant down-regulation of AQP4 in the acute phase of disease and an up-regulation of AQP1 and AQP4 in the long term. AQP4 modulation has been suggested as a potential target for treating brain edema associated with herpetic infection by HSVE (Torres et al., Journal of NeuroVirology (2007), 13(1), 38-46).

Two members of the aryl-sulfonamide structural class have been reported as inhibitors of the AQP4 channel (Huber et al., Biorganic & Medicianal Chemistry Letters (2007), 17, 1270-1273). One of these compounds, acetazolamde, has recently been claimed as a carbonic anhydrase inhibitor for the treatment of unstable cerebralspinal pressure syndrome (Yoshida, Application: WO 2006-JP322065 20061030). However, there is a lack of reliable information about the structures of compounds that regulate AQP4 function (Dun et al., Neural Regeneration Research (2007), 2(4), 234-238.).

It has been an unachieved objective to identify and characterize aquaporin modulators, such as AQP4 blockers or activators, as a potential adjunct therapy for clinical intervention in edema and stroke-related pathologies (Zador et al., Progress in brain research (2007), 161 185-94).

While little has previously been known regarding the pharmacology of AQP channels, some compounds, such as mercury and organic mercurials, selectively block some types of AQPs, such as AQP1, but not AQP4. However, these blockers exhibit high systemic toxicity negatating their potential therapeutic value. Other aquaporin blockers, such as tetraethylammonium and phloretin suffer from a lack of specificity and potency. While AQP4 expression have been associated with phenomena like edema, suitable pharmacological compounds for modulating AQP4 activity or suitable for prospective clinical use have not been available. There is also a significant need to develop novel and/or selective AQP modulators for further investigation of the role of aquaporins in edema and other disease phenomena.

To address these problems, the inventors have identified novel compounds that agonize or antagonize aquaporin activity and which lack the toxicity, poor potency and low specificity of prior art compounds.

BRIEF DESCRIPTION OF THE INVENTION

The inventors have discovered that bumetanide, furosemide, and other substituted 3-carboxy-aryl-sulfonamide derivatives or analogs are blockers, and in some cases stimulators, of aquaporin function in an oocyte expression system. Compounds having these basic core structures have been demonstrated to selectively modulate AQP1 and AQP4 function in cells. This important discovery of a class of aquaporin-modulating pharmacological agents has led to new ways to significantly decrease the formation of edema after ischemic stroke and acute brain injury. Furthermore, this class of aquaporin modulators allows treatment of other diseases associated with or mediated by aquaporins, such as glaucoma, macular degeneration, pulmonary disorders, and certain types of cancers, such as brain tumors.

In view of the above discovery, several nonlimiting aspects of the invention are:

Compounds having the 3-carboxy aryl sulfonamide structure defined by formula (I):

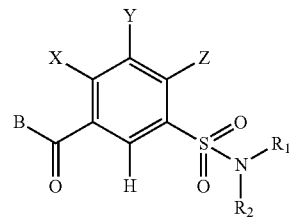

Formula I or additional aryl sulfonamides of structures II-IV:

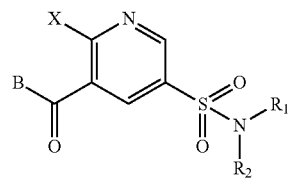

Formula (II)

-continued

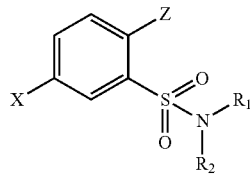

Formula (III)

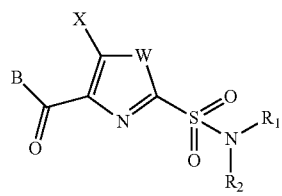

Formula (IV)

or a pharmaceutically acceptable salt thereof,
wherein:

B is —OH, —OR, —OCHR₁OCOR₂, or NR'₁R'₂;

X, Y, and Z are, independently, selected from the group consisting of hydrogen, halogen, —OH, —OR, —NHR, —NHCOR, —NHSO₂R, —SR, —SOR, or —SO₂R;

wherein R is one member of the group consisting of:
(a) a linear or branched C1 to C6 alkyl;
(b) aryl or aryl C1 to C6 alkyl, unsubstituted or substituted with at least one member of the group consisting of halogen, trihalomethane, hydroxy, alkoxy, aryloxy, amino, N-alkylamino, N,N-dialkylamino, alkylcarbamoyl, arylcarbamoyl, aminocarbamoyl, N-alkyl- or N,N-dialkylaminocarbamoyl, alkylsulfonylamino, arylsulfonylamino, carboxy, carboxyalkyl, N-alkylcarboxamido, N,N-dialkylcarboxamido, alkylthio, alkylsulfinyl, alkylsulfonyl, trifluoromethylsulfonylamino, arylthio, arylsulfinyl, arylsulfonyl, hydroxyalkyl, alkoxyalkyl, aryloxyalkyl, aminoalkyl, N-alkylaminoalkyl, N,N-dialkylaminoalkyl, alkylcarbamoylalkyl, arylcarbamoylalkyl, aminocarbamoylalkyl, N-alkylaminocarbamoylalkyl N,N-dialkylaminocarbamoylalkyl, alkylsulfonylaminoalkyl, arylsulfonylaminoalkyl,
(c) heteroaryl or heteroaryl C1 to C6 alkyl, unsubstituted or substituted with at least one member of the group consisting of halogen, trihalomethane, hydroxy, alkoxy, aryloxy, amino, N-alkylamino, N,N-dialkylamino, alkylcarbamoyl, arylcarbamoyl, aminocarbamoyl, N-alkyl- or N,N-dialkylaminocarbamoyl, alkylsulfonylamino, arylsulfonylamino, carboxy, carboxyalkyl. N-alkylcarboxamido, N,N-dialkylcarboxamido, alkylthio, alkylsulfinyl, alkylsulfonyl, trifluoromethylsulfonylamino, arylthio, arylsulfinyl, arylsulfonyl, hydroxyalkyl, alkoxyalkyl, aryloxyalkyl, aminoalkyl, N-alkylaminoalkyl, N,N-dialkylaminoalkyl, alkylcarbamoylalkyl, arylcarbamoylalkyl, aminocarbamoylalkyl, N-alkylaminocarbamoylalkyl N,N-dialkylaminocarbamoylalkyl, alkylsulfonylaminoalkyl, arylsulfonylamninoalkyl, alkylcarboxy, alkylcarboxyalkyl, N-alkylcarboxamindoalkyl, N,N-dialkylcarboxamindoalkyl, alkylthioalkyl, alkylsulfinylalkyl, alkylsulfonylalkyl, trifluoromethylsulfonylaminoalkyl, arylthioalkyl, arylsulfinylalkyl, and arylsulfonylalkyl; and R₁ and R₂ or R'₁ and R'₂ are:
(a) independently hydrogen or an optionally substituted linear or branched C₁-C₆ alkyl;

(b) a group of the formula —(CH₂)ₙCHR-Q or —CHR(CH₂)ₙ-Q where n=0-2 and Q is taken from aryl, heteroaryl, —CF₃, —CH₂OH, —OR₃, —CH₂NHCOR₃, —CH₂NHS(O)₂R₃, —SR₃, —S(O)R₃, —S(O)₂R₃; and R₃ may be either H, C1-C6 linear or branched alkyl, aryl C0-C3 alkyl-, heteroaryl C0-C3 alkyl-, (c) a group of the formula —CH₂CHR-Q or —CHRCH₂-Q where n=0-2 and Q is —NHCONR₃R₄ or —NR₃R₄, where R₃ and R₄ are independently H, C1-C6 linear or branched alkyl, aryl, heteroaryl, aryl C1-C3 alkyl, heteroaryl C1-C3 alkyl, or when taken together form a ring of:

wherein
A is selected from the group consisting of —(CH₂)ₙ—, —CH=CH— —(CH₂)ₙCO—, —(CH₂)ₙO—, —(CH₂)ₙSOₘ—, or —(CH₂)ₙNR—, and —NRCO—, n and m are independently integers between 0 and 2, and R is as defined above, D is —(CH₂)ₙ— and n is an integer between 0 and 2, E and F are, independently, —(CH₂)ₙ— wherein n is an integer between 0 and 2; or a substituted or unsubstituted adjacently attached aryl- or heteroaryl-ring system;

(d) when taken together with the nitrogen atom to which they are attached form a substituted or unsubstituted 5 to 7-membered heterocycloalkyl which may contain a heteroatom containing group, such as —O—, —S—, —SO—, —SO₂—, —NH—, —NR—, —NCOR—, —NSO₂R—, internal to the ring system and is optionally fused to a substituted or unsubstituted aryl or heteroaryl group and R is as defined above. Where W in formula (IV) is S, O, NR wherein R is H, alkyl, or aryl alkyl.

Preferable substituents for the compounds of formula (I) include the following: compounds where X is hydrogen, Y is —NHR, and/or Z is OR. Compounds where X is hydrogen, Y is —NHR, and Z is OR and R₁ and R₂ are hydrogen. Compounds where X is hydrogen, Y is —NHR, Z is OR, R₁ and R₂ are hydrogen, and B is —OR. Compounds where X is hydrogen, Y is —NHR, Z is OR, R₁ and R₂ are hydrogen, and B is —OR or B is —NR'₁R'₂ Compounds where X is —OR, Y is hydrogen, and/or Z is halogen, and where R, and R₂ may be hydrogen. Compounds where X is —OR, Y is hydrogen, and/or Z is halogen, and where R₁ and R₂ are hydrogen and where B is —OR or B is —NR'₁R'₂. |Other preferred compounds include those of formula (I) where B is —OR, or wherein B is —OR and wherein R is either —CHR₁—O—COR₂ or is —NH(CH₂)₂-morpholino.

A method for screening compounds for their ability to modulate aquaporin activity based on a water permeability assay in *Xenopus* oocytes expressing aquaporins which is used to identify, assess, and characterize compounds that either block or stimulate the aquaporin channels including AQP1, AQP4 and AQP9 channels.

New uses for previously marketed loop diuretics bumetanide and furosemide. These uses include therapeutic methods using these old agents (as well as new analogs and derivatives) in AQP4 expressing tissues or organs where regulation of edema or fluid balance is required. New ways to introduce bumetanide and furosemide into target cells where these compounds have significant activity on aquaporins such as AQP4 are disclosed, including design of prodrug forms of these compounds that produce molecules that are intracellularly active on aquaporins when taken up by cells. The acetoxymethyl prodrug of furosemide (Pandi, et al., Il Farmaco, 1992, 47, 249-263; Il Farmaco, 1992, 47, 1225-1230) shown below may be employed as an AQP4 modulator and antagonist:

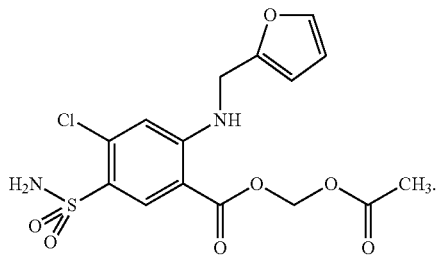 [SMILES: CC(=O)OCOC(=O)c1cc(S(N)(=O)=O)c(Cl)cc1NCc1ccco1]

The above compound is one example of a compound that has a new use for modulating aquaphorin activity when bioconverted to a known drug (furosemide) inside of a cell. Similar prodrugs based on either bumetanide and furosemide or other known loop diuretics which bioconvert inside of a target cell are contemplated and may be produced as described herein.

New compounds based on the core structure, such as that shown in formula (I), have been designed and methods for enhancing the modulatory efficacy, in vivo stability, solubility, and transport of these compounds into cells through derivatization, analog synthesis, and rescaffolding.

Novel methods for using prior art compounds like bumetanide and furosemide and new analogs and derivatives such as compounds of formula (I) for the treatment of edema, attenuation of cerebral pressure, and maintenance of fluid balance in aquaporin-expressing tissues or organs, especially those expressing AQP4, useful for treating conditions such as stroke, brain trauma, glaucoma, macular degeneration, brain tumors, and cerebral infectious diseases.

Pharmaceutical preparations and various modes of administering the compounds of the invention in ways that reduce edema in a subject suffering from edema associated with conditions including stroke, trauma, glaucoma, macular degeneration, brain tumors, and cerebral infectious diseases.

BRIEF DESCRIPTION OF THE DRAWINGS

FIG. 2A shows a dose-dependent block by extracellular bumetanide- and similar block at 100 μM by furosemide. FIG. 2B shows an absence of block by torsemide at concentrations up to 1 mM. FIG. 2C shows a corresponding summary histogram showing n values (below x-axis) and statistical significance. FIG. 2D shows structures of the loop diuretic compounds; differences provide insight into features relevant to AQP4 block. FIG. 2E shows an enhanced efficacy of internal injection of the blocker into the oocyte, consistent with an internal site of action; FIG. 2F shows a summary histogram of data for "i" intracellular, "e" extracellular applications of bumetanide and furosemide.

Symbols: o not different from untreated wild type; * $p<0.05$, ** $p<0.01$. Unpaired Student-t test.

Figure 3A:
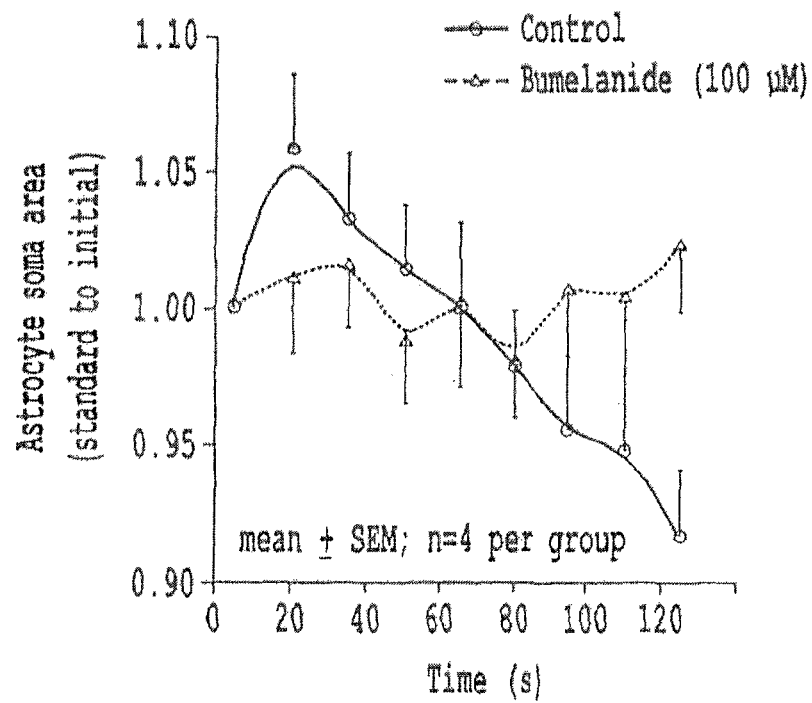
Figure 3B:
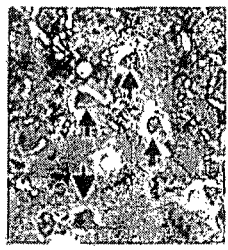
Figure 3C:
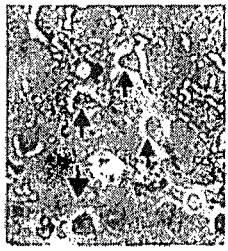

FIGS. 3A, 3B, and 3C show a protective effect of bumetanide on astroglial swelling in primary hippocampal cultures (14-15 days in vitro) after exposure to 50% hypotonic saline at time zero. FIG. 3A is a cell area visualized by phase contrast microscopy, standardized to the initial volume quantified by Scion Image (NIH) software. FIG. 3B shows glial cells (arrows) with bumetanide treatment before hypotonic saline and FIG. 3C shows glial cells (arrows) with bumetanide at 15 s in 50% hypotonic saline.

Figure 4:
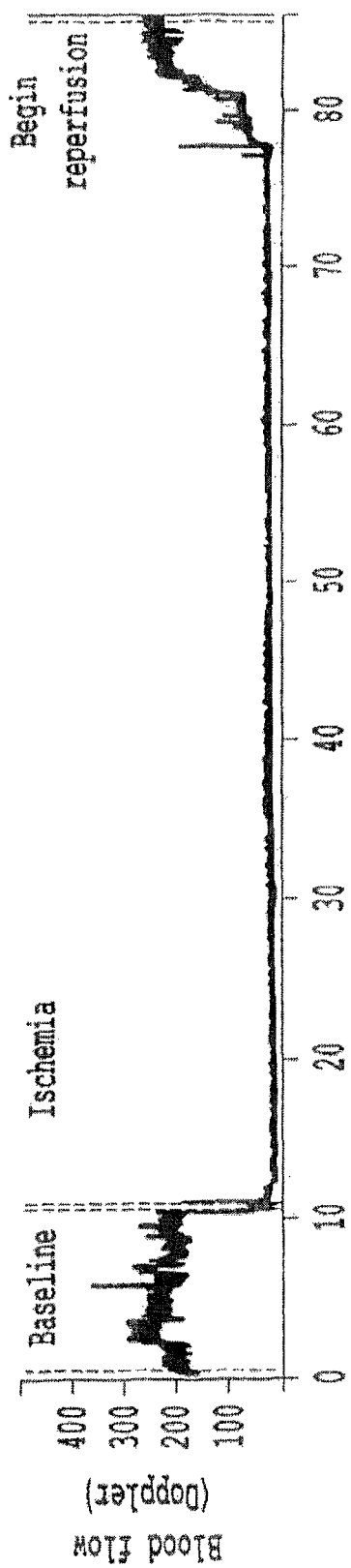

FIG. 4 shows the Doppler laser measures of blood flow rate before, during and after imposition of ischemic stroke by middle cerebral artery occlusion in a male control mouse.

Figure 5:
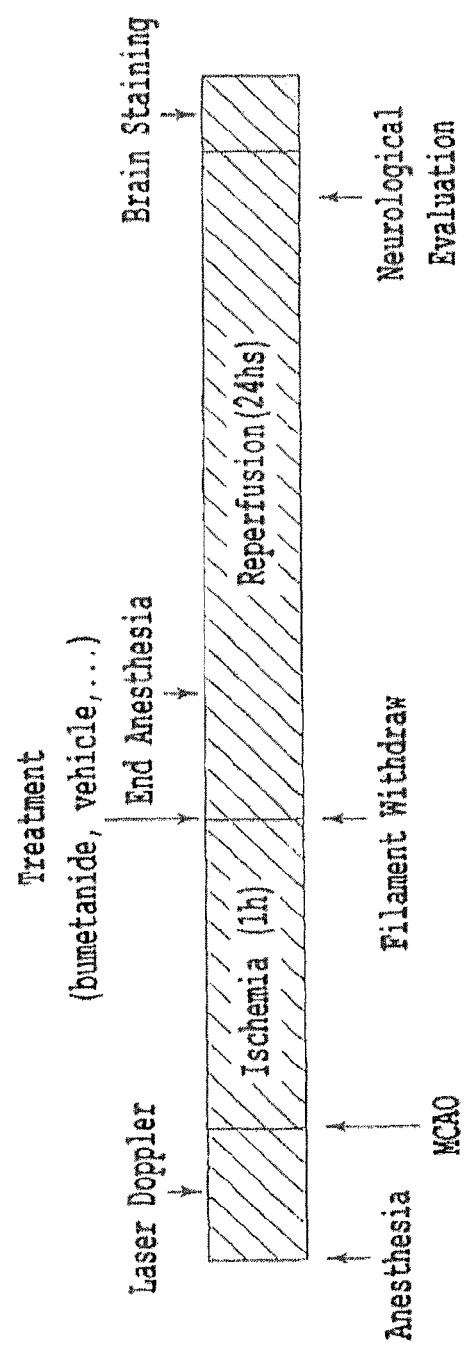

FIG. 5 depicts a schematic which illustrates the timeline for the standard in vivo experimental protocol.

Figure 6A:
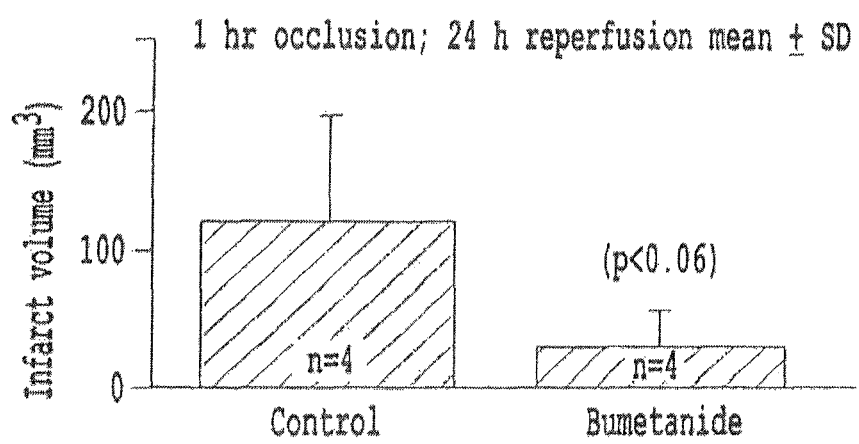
Figure 6B:
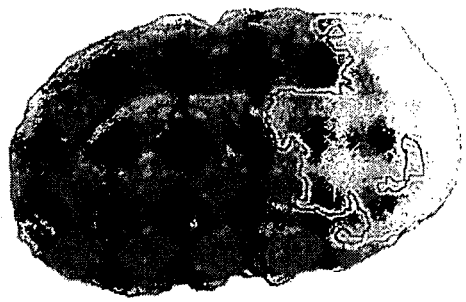
Figure 6C:
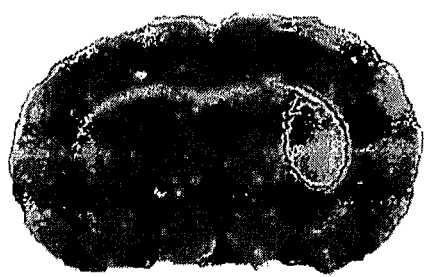
Figure 6D:
Figure 6E:

FIG. 6A shows a graph showing the effect of bumetanide treatment on the infarct volume. FIGS. 6B and, 6C, 6D, and 6E show cerebral edema samples in mice subjected to one hour of ischemia and 24 hours of reperfusion, with and without bumetanide (60 mg/kg) administered intravenously in a single bolus at 10 min before reperfusion. Stained with 2% TTC, the infarcted area is white; areas are analyzed using morphometric software by researchers blinded to the treatment group. Statistical significance (p<0.06) does not meet criteria, but indicates promise, and may be confirmed as the n value is increased.

Manley, et al., 2000, FIGS. 3 and 4B, show neurological deficits and extent of brain swelling after permanent occlusion in a stroke model. (A) Histological analysis of $AQP4^{+/+}$ and $AQP4^{-/-}$ mouse brain 24 h after MCA occlusion. Hemispheric enlargement was significantly less in $AQP4^{-/-}$ mice (n=7 each). (B). Neurological outcome following MCA occlusion in $AQP4^{+/+}$ and $AQP4^{-/-}$ mice at 24 h. Mean values: symbols with error bars.

Figure 1:
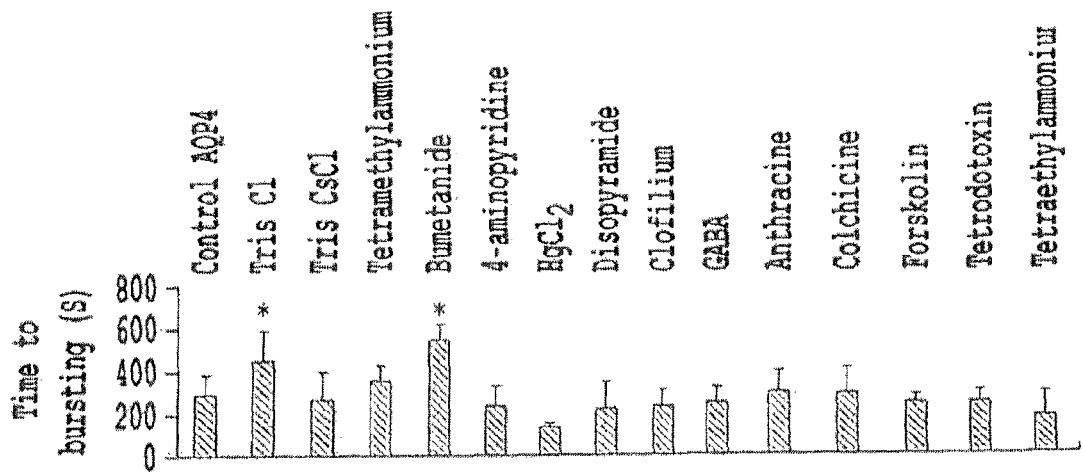
FIG. 1 shows an effect of agents on time to burst for AQP4-expressing oocytes. Of more than 30 compounds screened in our pilot study, 100 μM bumetanide was one of four compounds that significantly delayed bursting time in AQP4-expressing oocytes. AQP4 (also known as the 'mercury-insensitive water channel') showed no effect of $HgCl_2$.
Figure 2A:
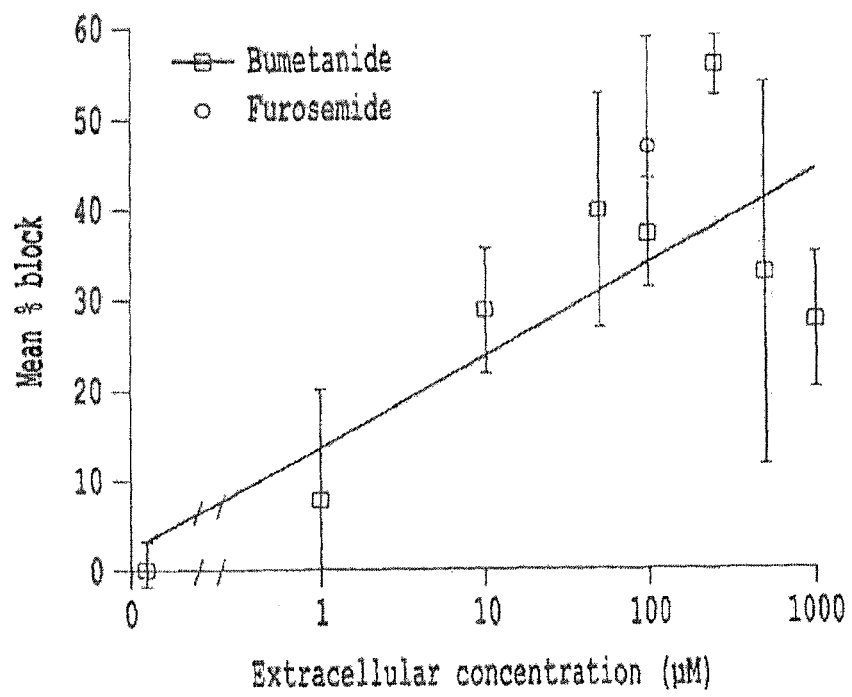
FIGS. 2A, 2B, 2C, 2D, 2E, and 2F show quantitative analyses of block in AQP4-expressing oocytes by bumetanide and related loop-diuretic compounds.
Figure 2B:
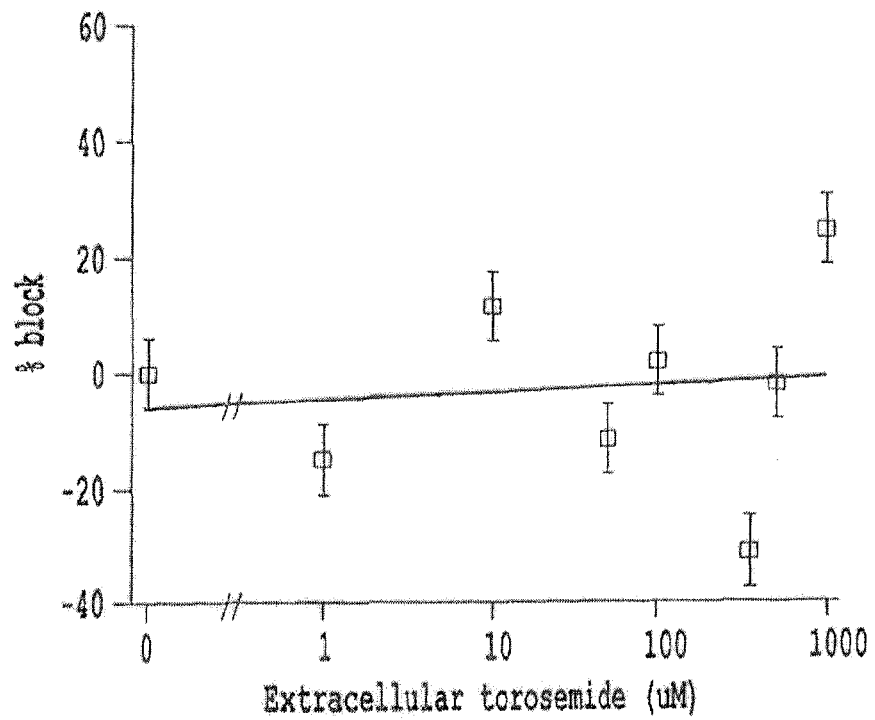
Figure 2C:
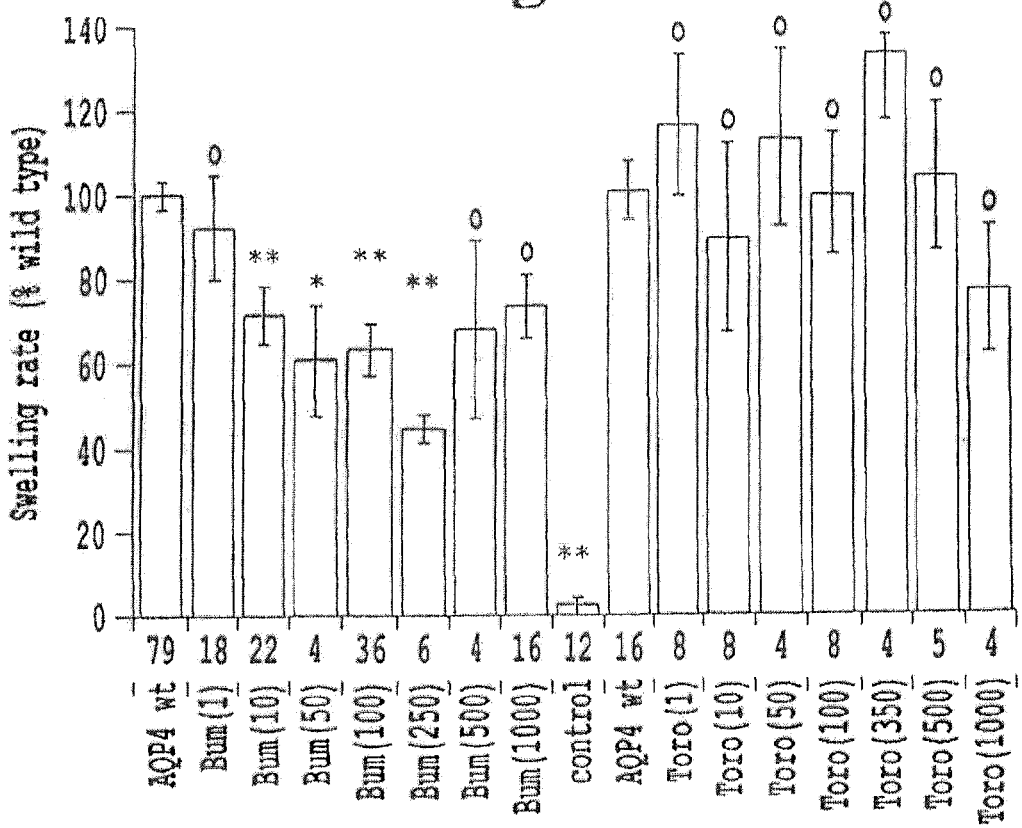
Figure 2D:
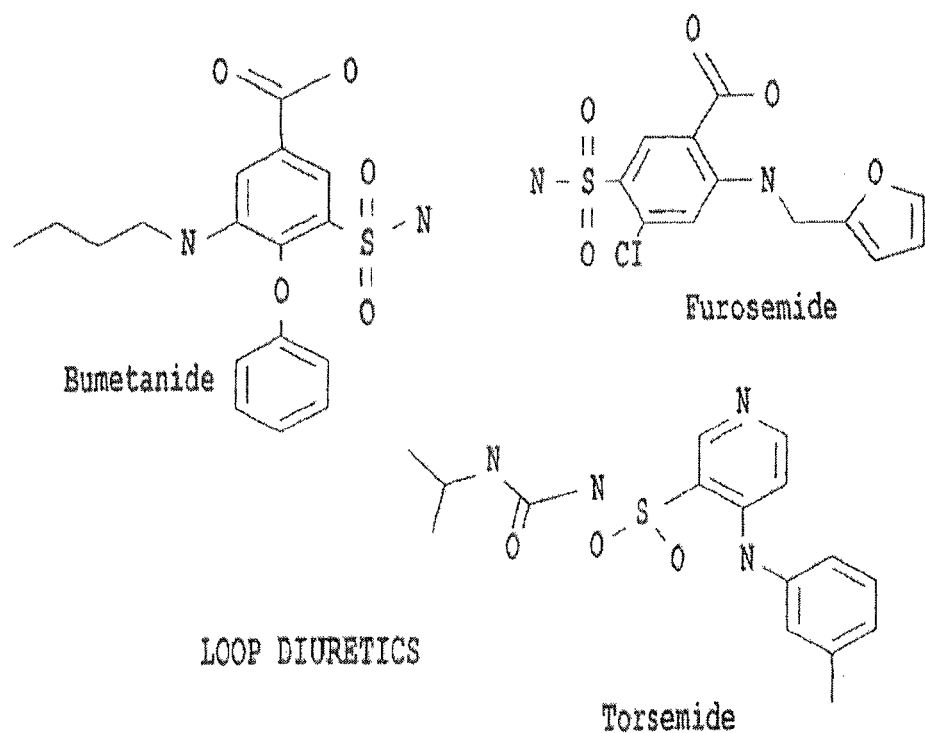
Figure 2E:
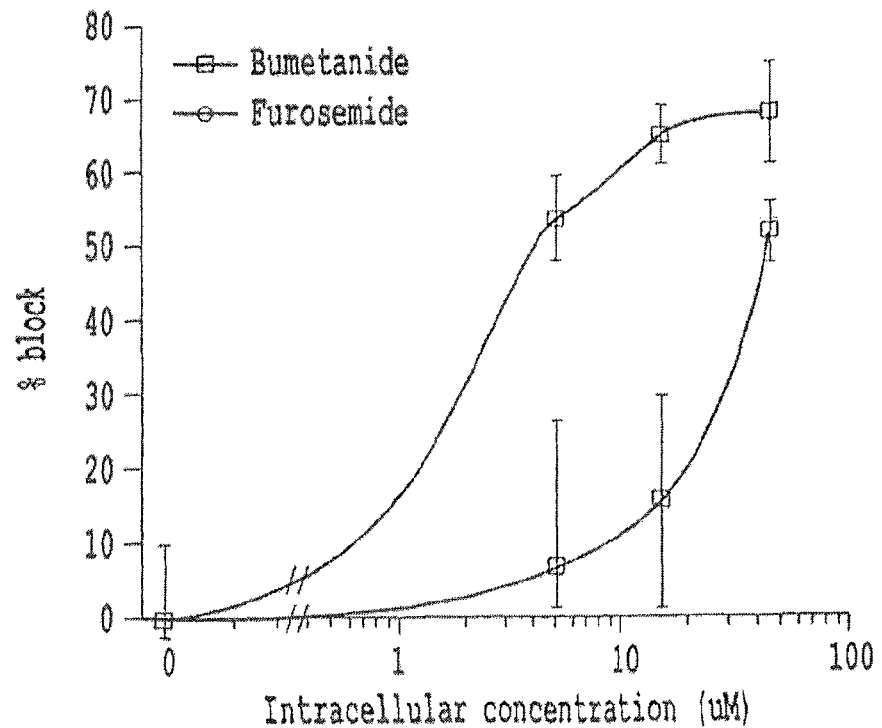
Figure 2F:
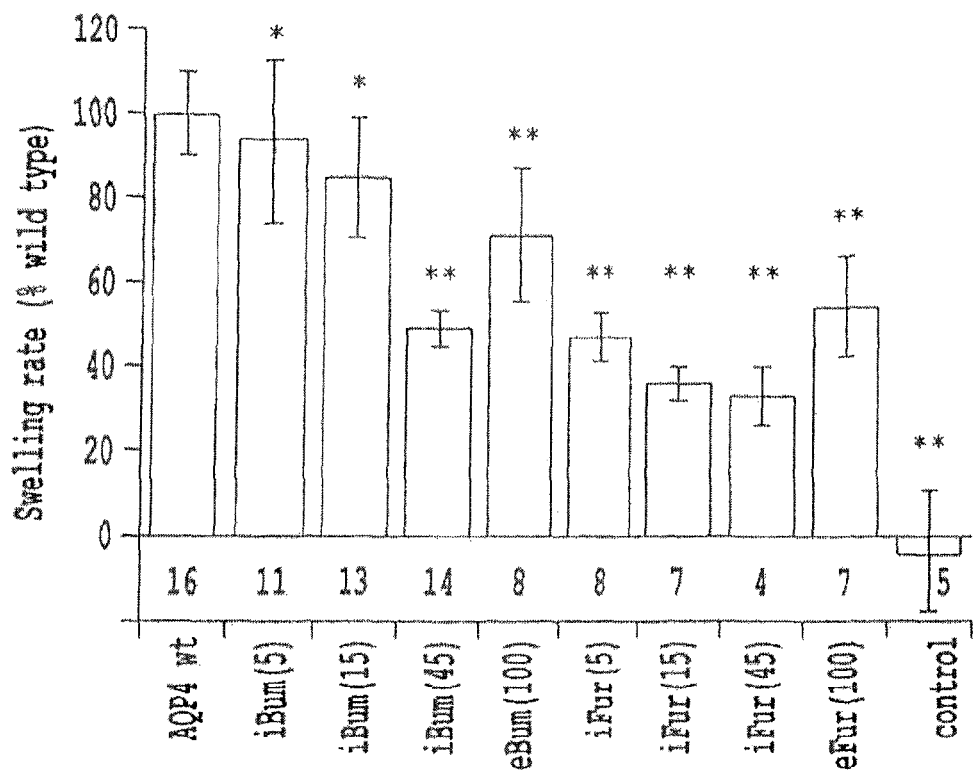

Dirnagl, et al., 1999, FIG. 1, provide a schematic diagram of the time scale of injury after ischemic stroke, and their relative impacts.

Brooks, et al., 2000, FIG. 6, show the effects of tetracthylammonium (TEA) on the water permeability (Pf) values of wild-type and site-directed mutant AQP1 channels expressed in oocytes.

De Groot and Grubmuller (2001), FIG. 1, depict the AQP1 crystal structure. (a) Extracellular view of the AQP1 tetrameric channel. A water pore is located in the center of each subunit. (b) Side view of a single subunit showing the signature NPA (arg-pro-ala) regions at the center of the hourglass-shaped pore. The N- and C-termini are located on the cytoplasmic side of the protein.

DETAILED DESCRIPTION OF THE INVENTION

The methods and compounds disclosed in this invention modulate aquaporin water channels, in particular aquaporin 1 (AQP1) and aquaporin 4 (AQP4), and as such may be used to treat patients suffering from various conditions mediated by edema, pathological water redistribution, distribution or flux, and inflammation. Treatment will reduce the level of edema in the brain or other tissues where AQP4 is abundantly expressed. Such conditions treatable by this invention include ischemic and hemorrhagic stroke, edema resulting from head trauma, edema from brain tumors, cerebral/pulmonary edema from certain infectious diseases including but not limited to encephalitis or meningitis.

The compounds of the invention may be administered to patients in a variety of forms. These include intravenous injection (bolus or infusion), intramuscularly (IM), oral delivery (via pill, tablets or capsules), inhalation (intranasal or pulmonary as aerosolized liquids or dry powders), rectally, buccally or across other mucosal tissues, or across the skin by "patch" technologies. The formulations to achieve these means of delivery are well known in the art, using known buffers, sugars, salts, osmotic agents, excipients, binders, physiologically acceptable solvents, and the like. The dosing may be determined by standard pharmacological methods well known in the art.

Aquaporin Compositions and Routes of Administration

The term "aquaporin modulator" includes both aquaporin agonists (e.g., a compound that enhances or facilitates aquaporin function) and antagonists (e.g., a compound that blocks water transport by an aquaporin).

The term "prodrug" includes both aquaporin modulators that are metabolized upon administration or ingestion into an active aquaporin modulator, e.g., after ingestion or transport into the circulatory system, as well as to compounds which are metabolized into an active aquaporin modulator once transported inside of a cell.

The term "administer" includes any method of introducing the aquaporin modulators of the present invention into a subject or exposing a subject to these compositions. This includes administration of prodrugs which convert into a compound of the invention when administered to a subject or which are otherwise treated to release an active form prior to administration.

The term "pharmaceutically acceptable carrier" includes any and all carriers and excipients such as diluents, solvents, dispersing agents, emulsions, lipid bilayers, liposomes, coatings, preservatives including antibacterial or antifungal agents, isotonic agents, pH buffers, and absorption modulating agents, and the like, compatible with the aquaporin modulators of the present invention and suitable for pharmaceutical administration. The use of such carriers, disintegrants, excipients and agents for administration of pharmaceutically active substances is well known in the art, see the *Handbook of Pharmaceutical Excipients*, 3$^{rd}$ edition, Am. Pharm. Assoc. (2000) which is incorporated by reference.

The pharmaceutical compositions of the invention are generally formulated for compatibility with an intended route of administration, such as for parenteral, oral, or topical administration. Routes of administration also include intravenous (i.v.), intradermal, subcutaneous (s.c.), intracerebral, transmucosal, transdermal, by inhalation (e.g., intratracheal, intrapulmonary, or intrabroncial), intransal, oral, subuccal, transdermal, and rectal administration. The pharmaceutical compositions of the invention may be formulated as unit doses or placed in individual containers, such as a syringe, ampule, vial, capsule or table, containing a unit dose. They may also be formulated as timed-release preparations that release the aquaporin modulator at a predetermined rate once ingested or administered, or which protect the aquaporin mediator from degradation or premature metabolization.

Orally administered compositions can include a solid carrier or excipient or may be formulated as liquid or gel preparations. Compositions for oral administration may include an edible or inert carrier and may be enclosed in capsules, compressed into tablets, or formulated as a troche. Orally administered compositions may be prepared in a time-release or encapsulated form to prevent degradation in the stomach and optimize uptake of an aquaporin modulator or a prodrug that is metabolized inside of a cell into an aquaporin modulator.

Injectable compositions may be formulated by methods well known in the art and may encompass sterile solutions or dispersions of aquaporin modulators. Such will usually include a sterile diluent, such as water, normal saline, or other buffer compatible with the aquaporin modulators of the invention. Conventional buffers and isotonic agents may be used and pH may be adjusted using well known agents, such as HCl or NaOH or buffers. Antimicrobial or bacteriostatic agents, chelating agents, such as EDTA or EGTA, and antioxidants and preservatives may be present.

An aquaporin modulator of the invention may be administered by inhalation, for example, by nebulization, atomization, or by delivery in the form of an aerosol spray. These may be placed in a pressurized container or dispenser containing a propellant and optional carrier suitable for pharmaceutical use.

The dosage of an aquaporin modulator will vary depending on the condition to be treated, its anatomical location, the underlying physiology of the disorder and the pharmacological properties of the aquaporin modulator. In general, a dosage ranging from 0.01 mg/kg to 10 mg/kg, preferably between 0.1 mg/kg and 5 mg/kg will be administered.

Treatment of Diseases and Disorders by Selective Targeting of Aquaporins

Aquaporins (AQPs) are a family of related proteins that are expressed in physiologically essential tissues and organs in which edema and fluid imbalances are of major concern. Compounds, such as those of general formula (I), that modulate aquaporin activity are useful in preventing or treating diseases and disorders mediated by aquaporins or characterized by abnormal expression of aquaporins. Such diseases and disorders include those associated with regulating brain water homeostasis and edema, angiogenesis, cell migration, development, neuropathological diseases, and cancer.

Treatment of Brain Edema Using Aquaporin Modulators.

The aquaporin modulators of the invention, such as the compounds of general formula (I), may be used to mediate edema, such as swelling due to fluid accumulation (edema) and fluid imbalances involving aquaporins are a major concern in the eye and the brain (Amiry-Moghaddam and Ottersen, 2003; King et al., 2004; Venero et al., 2004). The currently known blocking agents for AQP are mercury and organic mercurials, and are clearly not feasible for use as therapeutic agents due to their toxicity. Potassium homeostasis is essential for the control of neuronal excitability and is closely connected with mechanisms for the control of fluid volume. AQP4, the primary water channel of CNS astroglia, is colocalized with the inward rectifier Kir4.1 in specialized endfoot regions of astrocytes Efflux of Cl$^-$ in parallel with K+ export via Kir4.1 channels favors the export of KCl salt by electroneutral transport, and thus provides a reasonable driving force for water flow through associated AQP4 channels in the perivascular endfeet.

AQP4 channels in the CNS allow water homeostasis, with particular importance in mediating export of water from the brain under physiological conditions, but create vulnerability to edema under pathological conditions where there is unwanted "backflow" of water from the blood into the brain when the blood plasma is too dilute (a condition known as hyponatremia, or "water toxicity").

The loss of AQP4 in mouse genetic models from the glial endfoot zone provides a beneficial effect in delaying the onset of induced brain edema, and clinical treatments of pharmacologically blocking these water channels can provide a protective effect against edema. With an antagonist, the acute absorption of water might be prevented by an AQP4 blocker during early edema formation. With an agonist, the normal longer term mechanisms of AQP4 in restoring water homeostasis by exporting water from the brain could be enhanced. The natural response of brain glia to up-regulate AQP4 when faced with water overload would support the concept that the glial endfeet provide an important mechanism for water extrusion. The sequential application of an antagonist during the first few hours and an agonist subsequently can be used to optimize the clinical treatment of stroke- and injury-induced brain edemas.

Edema results from many clinical conditions including several neurological conditions or pulmonary conditions. One of the major unmet medical needs is in stroke. Stroke, as the third leading cause of death, is a devastating disease affecting more than 700,000 people in the United States each year. The extent of brain edema is a major determinant of patient survival after a stroke event (Dirnagl et al., 1999; Taylor et al., 1996). For progressive edema due to middle cerebral artery occlusion, mortality approaches 80% (Ayata and Ropper, 2002). The propensity of ischemic brain tissue to develop edema remains the major cause of death in patients with large infarctions, particularly within the middle cerebral artery territory and cerebellum involved in 15-20% of all strokes (Hacke et al., 1996). Thus, the identification of molecular targets for intervention in the edema process is a compelling research goal. At present, optimal strategies for management of ischemic brain edema remain elusive, and available treatments are often of limited value for patients with massive edema.

Brain edema is classified as vasogenic (movement of water and solutes across the blood brain barrier), or cytotoxic (osmotic swelling of cells in the affected area) (Fishman, 1975; Klatzo, 1967). Cytotoxic edema correlates with initial infarct size, and vasogenic edema contributes to the delayed risk-prone processes of brain swelling (FIG. 2). Astrocytes play a role in both processes. Astrocyte endfeet covering the abluminal capillary surface promote maintenance of intercellular tight junctions between endothelial cells that create the blood-brain barrier (Huber et al., 2001). Blood-brain barrier disruption after ischemia involves altered transport, opening of paracellular pathways, and physical disruption of astrocyte-endothelial junctions (Sun and O'Donnell, 1996; Venero et al., 2001). Pericapillary astrocyte endfeet are the first cellular elements to swell during brain ischemia (Dodson et al., 1977), a process thought to result from uptake of extracellular $K^+$, $Cl^-$, and $Na^+$ and the osmotic flux of water (Su et al., 2002), promoting a progressive cascade of pathology.

As noted above, the formation of brain edema is delayed following knockout of the AQP4 channel in mice, thus the aquaporin modulators of the invention, particularly modulators of AQP4 function, offer significant clinical benefits to patients suffering from conditions involving brain edema.

Treatment of Brain Trauma

Aquaporin modulators of the invention, such as the compounds of general formula (I) may be administered to subjects having brain trauma to reduce or control edema or intracranial pressure. Aquaporin antagonists, e.g., an AQP4 antagonist, may be administered to reduce the effects of increased expression of AQP4 that results in edema associated with stroke or head trauma. Attenuated head trauma induced by AQP4 loss observed with post-injury administration of sulforaphane (SUL), an isothiocyanate present in abundance in cruciferous vegetables such as broccoli. were accompanied by a significant reduction in brain edema (assessed by percentage water content) at 3 days post-injury. (Zhao et al., Journal of Neuroscience Research (2005), 82(4), 499-506).

Aquaporin agonists may be given to subjects having head injuries to reduce intracranial pressure associated with the decreased expression of aquaporins, such as AQP4 (Hoshi et al., Sei Marianna Ika Daigaku Zasshi (2005), 33(5), 373-381).

Treatment of Heavy Metal Poisoning Using Aquaporin Modulators

Subjects exposed to lead may be treated by administering an aquaporin modulator to reduce the effects of lead poisoning on water permeability. Exposure of a subject to lead induces a significant 40% increase in water permeability (Pf) in astrocytes expressing AQP4, but had no effect on Pf in astrocytes not expressing AQP4 (Gunnarson, et al., Neuroscience (Oxford, United Kingdom) (2005), 136(1), 105-114). Furthermore, although the increase in water permeability persisted after lead washout, treatment with a lead chelator (meso-2,3-dimercaptosuccinic acid) abolished the lead-induced increase in Pf. These data point to the role of AQP4 in the pathology and neurotoxicity associated with lead exposure for which treatment with a small molecule AQP4 blocker may be beneficial.

Heavy metals such as, mercury and organic mercurials, are known to selectively block some types of AQPs, such as AQP1, but not AQP4. Thus, abnormalities in aquaporin function caused by exposure to mercury compounds may be reversed or compensated by the administration of a selective aquaporin modulator of the invention.

The toxic effects of other heavy metals which affect aquaporin activity may be similarly treated using the aquaporin modulators of the invention.

Treatment of Ocular Disorders, Including Glaucoma, Macular Degeneration and Retinal Detachment Using an Aquaporin Modulator Aquaporin modulators of the invention, including the compounds of general formula (I) may be administered to subjects to regulate fluid volume, tissue hydration, and pressure associated with glaucoma and macular degeneration.

AQPs facilitate fluid secretion and absorption in the eye, and hence are involved in the regulation of pressure, volume and tissue hydration. For example, AQP4 is selectively expressed in ciliary epithelium and retinal Muller cells and mice lacking AQP4 have reduced light-evoked potentials by electroretinography (Verkman, et al., Experimental eye research (2003), 76(2), 137-43). Therefore, pharmacological alteration of AQP function provides a new therapy of glaucoma, corneal edema, macular degeneration and other diseases of the eye associated with abnormalities in IOP or tissue hydration.

AQP1 is the water channel expressed in retinal pigmented epithelium (RPE), a pigmented tissue that covers the back of the eye, absorbs stray light, and supports the function of the adjacent layer of photoreceptors. Working in parallel with salt ion channels and transporters, AQP1 enables the export of the water from the eye into the plasma across the RPE. The pull of salt and water out of the eye across the RPE has been suggested to be important in maintaining the attachment of the retina to the back of the eye. An agonist of AQP1 may be administered to slow or reduce the risk of blindness due to retinal detachment. Preferably, a blocker selective for AQP1 is employed, since it will not affect the AQP4 function of the glial cells in the adjacent retinal layers where primary visual information processing is occurring.

Treatment of Seizures and Emesis Using Aquaporin Modulators

Aquaporin modulators of the invention, such as the compounds of general formula (I) may be administered to subjects susceptible to seizures and emesis. AQP4 is the most important structural basis for the regulation and transportation of liquids between glia and interstitial fluid, and between cerebrospinal fluid and vascular blood vessel. It has been reported that mice deficient in the glial water channel aquaporin-4 (AQP4) show decreased cerebral edema and improved neurological outcome following water intoxication or ischemic challenge (Binder, et al., Neuroreport (2004), 15(2), 259-62). AQP4 participates in the formation of hydrocephalus and the occurrence of seizure, which result from various causes such as injury, stroke, brain tumor, and the like (Liu et al., Guoji Jianyan Yixue Zazhi (2006), 27(11), 999-1000, 1003). In addition, AQP4 expression in the brain of patients with medically intractable epilepsy have been shown to display a statistically significant increase in both mRNA and protein levels ($P<0.01$) that correlates with secondary cerebral edema after epilepsy attack (Chen et al., Neuroscience Bulletin (2005), 21(6), 413-417). Taken together, these show that glial water channels modulate brain excitability and the initiation and generalization of seizure activity. Blockade of AQP4 using an aquaporin antagonist of the invention may be used to reduce the severity and duration of seizures.

Improved Ability to Provide Osmoregulation Using Aquaporin Modulators

Aquaporin modulators of the invention, including compounds of general formula (I) are useful for regulating osmosis.

For example, AQP4 agonists and antagonists can be used to adjust the responsiveness of vasopressin secretion by the hypothalamus/pituitary axis in response to stimulation by changes in systemic blood plasma. Vasopressin is a hormone that controls body fluid homeostasis, with AQP channels expressed in both the source and target tissues for the signaling. The source of vasopressin is in the brain, specifically in the hypothalamic-neurohypophysial system where the magnocellular neurosecretory cells that synthesize the hormones vasopressin and oxytocin (involved in reproductive functions such as parturition and lactation) are located in the paraventricular and supraoptic nuclei (Young and Gainer 2003). These osmosensitive regions of the brain express high levels of AQP4 (Jung and others 1994; Nielsen and others 1997). Single axons from magnocellular neurons project to the neurohypophysis, releasing hormonal signals directly in the blood stream. The target of vasopressin is the collecting duct of the kidney, where V2-receptor binding induces the translocation of AQP2 channels to the plasma membrane to increase water reabsorption, hence producing an antidiuretic effect countering dehydration (Brown 2003). The presence of AQP4 controls the sensitivity of the osmosensory system; thus, antagonists of AQP4 can be used to dampen the responsiveness of the hormone secretion, whereas agonists can be used to boost the natural vasopressin control system for treatment of fluid loss, water retention, or high blood pressure.

Control of Hydrocephaly Using Aquaporin Modulators

Hydrocephaly is a disorder which is associated with abnormal accumulation of cerebrospinal fluid in the ventricles of the brain and may be ameliorated using the aquaporin modulators of the invention. Cerebral spinal fluid (CSF) that bathes the brain and spinal cord is produced by the choroid plexus, which expresses high levels of AQP1 channels. The AQP1 channels provide the pathway for water importation into the brain in parallel with transporters for $Na^+$ and $Cl^-$. Obstruction of the outflow of CSF through the arachnoid villi causes hydrocephalus, resulting in enlargement of the head in infants and neuropathology in older patients due to the internal increase in pressure. The current effective treatment for hydrocephalus is the surgical insertion of a shunt to vent excess fluid, although this method has drawbacks such as plugging and infection. Use of aquaporin antagonists of the invention, such as AQP1 antagonists, provides a way to ameliorate this condition without surgical intervention by adjusting fluid homeostasis-balancing CSF production with its removal from the brain.

Amelioration of Alzheimer's Disease Using Aquaporin Modulators

The aquaporin agonists of the invention can ameliorate Alzheimer's Disease by augment CSF product and turnover and flush out neurotoxins and toxic metabolite associated with Alzheimer's disease. Compromised function of the choroid plexus and decreased production of cerebral spinal fluid (CSF) may contribute to late-onset forms of Alzheimer's disease. CSF traditionally has been considered as a cushion providing physical protection of the brain, a reservoir of salts and nutrients, and a drainage system for removal of waste products and metabolites. Newer views extend the role of the choroid plexus and CSF into the development, homeostasis, and repair of the CNS (Redzic and others 2005). As reviewed by Redzic and colleagues, the choroid tissue synthesizes trophic and angiogenic factors, controls the entry of nutrients and peptide hormones, and serves in the clearance of toxins and drugs. Choroid-derived growth factors influence patterns during development; in adult CNS the choroid plexus appears to be involved in neuronal repair and recovery from traumatic and ischemic brain injury. With age, CSF secretion decreases, and can increase the risk for development of late-onset diseases such as Alzheimer's disease (Redzic and others 2005). Agonists of AQP1 can augment the CSF production, increasing the rate of turnover of the CSF and the corresponding flushing of extracellular space to offset the proposed neurotoxic accumulations of metabolites, toxins and waste products that are thought to contribute to Alzheimer's disease progression.

Maintaining or Restoring a More Normal Lung Function Using Aquaporin Modulators

The aquaporin modulators of the invention, such as those of general formula (I) may be used to treat disorders or diseases of the lung involving aquaporins. The degree of hydration of lung tissue plays a role in maintaining the normal function of the lung. Disorders in hydration including swelling, accumulation of fluid, and impaired gas exchange (pulmonary edema) can result. For instance, AQP4 is expressed in lung tissue and the compounds of the invention can modulate water transport and hydration in the lung by their effects on AQP4. The modulators of the invention may be used alone or in conjunction with other agents to treat disorders caused by disregulation of water in the lungs.

Treatment of Kidney Disorders and Diseases Using Aquaporin Modulators

The aquaporin modulators of the invention, especially, the antagonists may be used to manage water reabsorbtion in the kidney. For example, AQP1 is the primary mechanism for water reabsorption into the body from the lumen of the kidney in the proximal tubule and in the descending thin limbs of Henle. Thus, an antagonist of AQP1 may be employed to decrease water reabsorption and increase urine volume as a diuretic. AQP4 is present in the distal kidney, along with other AQPs, so possible agonist or antagonist effects in the kidney may muted by the presence of at least partially redundant mechanisms associated with AQP1 and AQP4. Thus pharmacological modulation of either or both of these aquaporins may be used to control water transport in the kidneys.

Treatment of Vascular Diseases and Disorders Associated with Aquaporin Expression Aquaporin antagonists may be administered to subjects having vascular disorders or diseases in order to modulate the effects of aquaporins in these diseases. For example, AQP1 is expressed in the endothelial cells of the peripheral vascular system, but is not present in the capillary beds of the central nervous system. AQP1 mediated changes in endothelial cell surface-to-volume ratios that are involved in controlling the paracellular permeability of the peripheral circulation, and the cell morphological changes associated with angiogenesis could thus be therapeutically controlled. In such a case, an antagonist of AQP1 could be used to decrease angiogenesis, a function of particular interest as an adjunct treatment in cancer therapy.

Treatment of Cancers or Tumors that Over-express Aquaporins or in which Aquaporins Contribute to Etiology or Morbidity The aquaporin modulators of the invention may be used to treat cancers in which aquaporins are up-regulated. Administration of an aquaporin antagonist of the invention can reduce the detrimental effects caused by up-regulation of aquaporins in such cancers. For example, AQP1 is up-regulated in brain glioblastoma and in breast cancer cells and is implicated in promoting cell shrinking, elongation and migration that enhances cancer spread. To prevent or ameliorate these detrimental effects, an antagonist of AQP1 is administered. Thus, the aquaporin modulator (antagonist) may be provided to a cancer patient as an adjunct treatment in cancer therapy, particularly for the glioblastoma multiforme which is highly invasive and thus extremely difficult to remove by surgery.

Recent evidence suggests that the membrane water channel protein aquaporin 4 (AQP4) plays a role in brain tumor edema. AQP4-deficient mice show remarkably altered brain water balance after various insults, including brain tumor implantation (Papdopoulos et al., Neuroscience (Oxford, United Kingdom) (2004), 129(4), 1011-1020). AQP4 expression increases in human brains after traumatic brain injury, within brain-derived tumors, and around brain tumors (Hu et al., Journal of Zhejiang University, Science, B (2005), 6B(1), 33-37). Because redistribution of AQP4 and Kir4.1 are different in low- and high-grade gliomas, the mechanisms of clustering of AQP4 and Kir4.1 at the glial endfeet membrane domains are also likely different and might be causatively involved in the formation of brain edema (Warth et al., Acta Neuropathologica (2005), 109(4), 418-426). Indeed, the intra-cerebral pressure created in high grade gliomas by AQP4 redistribution may be in part responsible for the pour response of some cancers of the brain to current chemotherapies. Benefits are, therefore, expected for the use of small molecule AQP4 blocking agents in adjunct therapy to attenuate the pressure gradient against which current and future brain cancer chemotherapies contend.

Remarkably impaired tumour growth has been observed in AQP1-null mice after subcutaneous or intracranial tumour cell implantation, with reduced tumour vascularity and extensive necrosis. However, stable transfection of non-endothelial cells with AQP1 or with a structurally different water-selective transporter (AQP4) accelerated cell migration and wound healing in vitro. These findings show a fundamental role of water channels in cell migration, which is central to diverse biological phenomena including angiogenesis, wound healing, tumour spread and organ regeneration (Saadoun et al., Nature (2005), 434(7034), 786-92).

Functional Characterization of Aquaporin Modulators

The aquaporin modulators of the present invention, including those having the structures of general formula (I) may be further characterized by particular functional properties. These properties include:

The increased ability of an aquaporin modulator to gain entry into a cell compared to bumetanide or furosemide when administered to a subject in an equivalent dose by the same route of administration. This increased ability may be imparted by modifications of the core structure of bumetanide or furosemide that make the modified compound (the aquaporin modulator) more easily transported or diffused across the cellular membrane to sites which modulate aquaporin activity inside of a cell and/or by an increased in vivo stability of the aquaporin modulator.

The functional characteristics of particular aquaporin modulators as characterized by molecular weight, $C_{log}P$, tPSA, or by a ratio of the modulator's hydrophobic and polar properties. An aquaporin modulator of the invention may have a molecular weight ranging from 250-550, preferably between 300 to 470; a $C_{log}P$ ranging from 0 to 5 preferably between 1 and 4; and a tPSA ranging from 70 to 170 $Å^2$, preferably between 100 to 150 $Å^2$ The aquaporin modulators of the invention as characterized by their effects on water transport in the oocyte swelling assay as disclosed above. When applied extracellularly the aquaporin modulators of the invention may have at least a 1, 5, 10, 20, 30, 40, 50, 60, 90 or 100% increased degree of agonism or antagonism or aquaporins, such as AQP1 or AQP4, compared to bumetanide or furosemide as measured by this assay. These range above includes all intermediate subranges and values.

Aquaporin modulators, especially antagonists, may selectively modulate one type of aquaporin channel, such as AQP1 or AQP4 and have no or a substantially reduce ability to agonize or antagonize other aquaporin channels. For example, a selective aquaporin antagonist could reduce aquaporin activity of AQP4 to 5, 10, 20, 50, 70 or 90% of its normal value, but not antagonize the activity of other aquaporin channels at all or significantly less than it antagonizes AQP4. A selective aquaporin antagonist would have a 5, 10, 20, 50, 75% or 100% greater ability to antagonize one type of aquaporin channel compared to another. An example of such a modulator would be a compound that blocks water flow via AQP4 channels, but which does not substantially block AQP1 or AQP9 channels, or a modulator which blocks AQP1, but does has substantially no activity on AQP4 channels.

Aquaporin modulators of the invention may have less activity on the Na—K—Cl cotransporter than bumetanide or furosemide. Relatively decreased Na—K—Cl transporter function activity of these aquaporin modulators may be characterized by measuring the torsemide-sensitive Na uptake into a cells. The cotransporter function is the classic target of the loop diuretics. From the loop diuretic family, torsemide does not affect Aquaporins, as is evident from the oocyte swelling assay data disclosed above, but still is a potent blocker of the cotransporter, so it can be used to characterize the activity of an aquaporin modulator on an Na—K—Cl transporter pathway vis-à-vis a control compound, such as bumetanide or furosemide.

The aquaporin modulators of the invention, such as compounds of general formula (I) may exhibit no activity on Na—K—Cl transporters compared to loop diuretics such as bumetanide or furosemide or at least a 1, 5, 10, 20 or 50% decrease in activity on Na—K—Cl transporters. The loop diuretic effect of an aquaporin modulator can be modifying the carboxylic acid group needed for the loop diuretic drug actions.

The range above includes all intermediate subranges and values. The differential activity of an aquaporin modulator of the invention on aquaporins and on Na—K—Cl transporters allows the therapeutic benefits of each to be differentially controlled. Sets of complementary and selective blockers permit customized adjustment of the treatment regime. For example, for treatment of brain edema it may be preferable to select an aquaporin modulate that blocks AQP4 and which also exhibits a loop diuretic action.

EXAMPLES

Example 1

Selection rationale and methodology. The ability of compounds, analogs and/or agents to block an aquaporin channel was quantified by videomicroscopic analyses of cross-sectional area of AQP-expressing oocytes as a function of time in a defined osmotic gradient, allowing the calculation of the water permeability factor (Pf), statistical evaluation of significant differences in the rate of water entry, and definition of dose response curves with $IC_{50}$ values (concentration required for half-maximal block).

This compound evaluation method has been utilized with AQP1,-4,-5, and -9 channels. Observations of channel stimulation were made using the same assay method, however, the results were reported as % stimulation over control at a given concentration. Previous studies by Yool and colleagues (Brooks et al., 2000; Yool et al., 2002) identified tetraethylammonium (TEA) as the first nonmercurial agent that blocks water flux through AQP1 channels (Brooks, et al., 2000). TEA is known as a blocker of $K^+$ channel subtypes and nicotinic acetylcholine receptors. TEA sensitivity of AQP1 was removed by site-directed mutagenesis of tyrosine 186 to phenylalanine (Y186F) in the outer vestibule of the water pore, and confirmed that the inhibitory action of TEA is not due to nonspecific effects on endogenous channels (Brooks et al., 2000).

Native AQP1 channels in kidney and recombinant AQP1 channels in Madin-Darby Canine Kidney (MDCK) cell line also showed block of water permeability by TEA (Yool et al., 2002), demonstrating this effect is not limited to the oocyte expression system. Inhibition of water permeability by TEA was seen in rat renal descending thin limbs of Henle's loops (which abundantly express native AQP1), and not in ascending thin limbs (which do not). This work has been independently confirmed and extended (Detmers et al., 2006; Tyagi and Namboodri, 2005), proving the feasibility of screening for blockers of aquaporin channels in the oocyte expression system. Brooks et al. (2000) shows the effects of tetraethylammonium (TEA) on the water permeability (Pf) values of wild-type and site-directed mutant AQP1 channels expressed in oocytes. Structural insights into understanding the mechanisms of AQP blocking agents were gained from the study of the deposited bovine AQP1 X-ray structure (IJ4N), see De Groot and Grübmuller. Block of the water flux through AQP1 was reported to involve the covalent binding of mercury ($HgCl_2$) at cysteine 189 (Preston et al., 1993). Because Cys-189 is in the outer water pore vestibule, block of AQP1 by mercurial compounds is believed to be a result of direct occlusion. However, molecular modeling studies reveal the corresponding residue in AQP4 to be a mercury-insensitive alanine, Conversely, AQP4 channel inhibition was reported to result from phosphorylation of serine 180 by PKC (Zelenina et al., 2002) while the equivalent residue in AQP1 is arginine. Furthermore, because Ser-180 is located away from the water pore, it is likely that channel inhibition is mediated by a conformational change, thus implying the capacity for allosteric modulation of AQP4 function. For these reasons the inventors first chose to evaluate a biased library of compounds as potential AQP4 channel blockers.

The composition of the library for initial AQP channel screening included various channel, transporter and receptor blocking compounds based on intuition and from clues regarding clinical side effects that involved water transporting tissues. In a simple screen (FIG. 1), control and AQP4-expressing oocytes were preincubated in isotonic saline (100 mM NaCl; 5 mM $MgCl_2$; 5 mM HEPES, pH 7.3; ~200 mOsm) containing the test compound for 10-15 min before each experiment; then the time to oocyte bursting (physical explosion) after transfer to 100 mOsm saline was monitored visually. In the absence of a blocking compound, osmotically-driven water influx led to rapid swelling and bursting. Block was evident in the increased time required for bursting in hypotonic saline. Control oocytes, adapted for a freshwater environment and lacking AQPs, show no detectable swelling at 10 min or more.

FIG. 1 shows the effects of agents on time-to-burst for AQP4 expressing oocytes. Of more than 30 compounds screened by the inventors, 100 µM bumetanide was one of four compounds that significantly delayed bursting time in AQP4-expressing oocytes. AQP4 (also known as the 'mercury-insensitive water channel') showed no effect of $HgCl_2$ These data show that significant APQ4 block resulted from treatment with 100 µM bumetanide. However, due to the cellular nature of this assay and the known Na—K—Cl channel blocking properties of bumetanide, it was essential to demonstrate that the blocking effect of bumetanide on oocyte swelling results from direct interaction with the AQP4 channel. The direct action of bumetanide on AQP4 was unambiguously demonstrated through site-directed mutagenesis studies which impaired the ability of bumetanide to block the AQP4 mutant but for which the rate of water flux was not altered. Noteworthy in these mutagenesis sites is their location at or near the intracellular surface of AQP4.

In addition to bumetanide, other classic loop diuretic drugs, such as furosemide and torsemide, were tested and found to vary significantly in their ability to block AQP4. In AQP4-expressing oocytes (FIGS. 2A-D), furosemide was less effective then bumetanide in blocking the swelling rate when administered in the normal extracellular fashion. Based on the site directed mutagenesis results, experiments were designed to test the proposed intracellular binding site for these agents. The observation that bumetanide and, in particular, furosemide exhibit improved block at lower concentrations, (FIGS. 2E and F), support our hypothesis that the putative binding site for these agents is on or near the intracellular side of the AQP4 channel. Moreover, this result revealed the importance of the 3-(sulfamoyl)benzoic acid scaffold, which is common to both furosemide and bumetanide, as a key pharmacophore element for AQP4 blocking agents.

Consistent with this finding is the finding that torsemide, which is dissimilar to bumetanide and furosemide, had no blocking effect on swelling in AQP4-expressing oocytes at concentrations up to 1 mM. Moreover, $IC_{50}$ values reported for these loop diuretics against the Na—K—Cl cotransporter (NKCC1) in cells differs from the values and trends observed in these AQP4 experiments. For example, furosemide exhibits a half-maximal blocking concentration ($IC_{50}$) of 23 µM and the $IC_{50}$ for bumetanide is 0.33 µM measured in a mouse kidney collecting duct cell line (Glanville et al., 2001), while the $IC_{50}$ for torsemide measured in perfused kidney ascending loops of Henle is 0.3 µM, (Greger, 1988). Thus, the inventors concluded that the contribution of endogenous volume regulatory responses is small in oocytes heterologously expressing abundant AQP4.

FIG. 2 presents a quantitative analyses of block in AQP4-expressing oocytes b bumetanide and related loop-diuretic compounds. (a) Dose-dependent block by extracellular bumetanide, and similar block at 100 µM by furosemide. (b) Absence of block by torsemide at concentrations up to 1 mM. (c) Corresponding summary histogram showing n values (below x-axis) and statistical significance. (d) Structures of the loop diuretic compounds; differences provide insight into features relevant to AQP4 block. (e) Enhanced efficacy of internal injection of the blocker into the oocyte, consistent with an internal site of action; (f) Summary histogram of data for "i" intracellular, "e" extracellular applications of bumetanide and furosemide. (e). Symbols: ○ not different from untreated wild type; * $p<0.05$, ** $p<0.01$. Unpaired Student-T test.

Example 2

In Vivo Effects of AQP4 Block

The role of native AQP4 as a target of block by bumetanide was tested in primary cultures of astroglia (FIG. 4). We compared the swelling responses of rat astroglial cells in primary hippocampal cultures after 15 min preincubation with or without drug. Swelling was induced by rapid perfusion of the culture plate with 50% hypotonic saline, either with or without extracellular bumetanide (100 μM) to match the preincubation condition. Glial cells were identified by morphological comparison with cells positive for a glial-specific marker (GFAP). Time-lapse images were taken at 15 second intervals before and during hypotonic challenge. The response was determined by the change in soma area as a function of time, as visualized by time-lapse digital imaging (Olympus MagnaFire™ camera and image acquisition software) using an inverted phase contrast microscope (Nikon); data were analyzed by Scion Image (NIH) software. Each culture was used for only one swelling trial. Control cultures were treated in parallel with equivalent doses of vehicle (DMSO) in the preincubation and hypotonic salines. The dose of DMSO had no appreciable effect on glial cell responses (not shown). Both the glial initial swelling and the subsequent regulatory volume decrease (RVD) were reduced by bumetanide treatment as compared with controls. Effects on RVD might be predicted from the block of ion transport systems, but the block of the initial swelling phase is consistent with a direct effect on the AQP4 water channel. Thus, AQP4 is a candidate target for the use of bumetanide (and more potent derivatives) in the mitigation of brain edema formation.

The inventors have shown that block of AQP4 protects astroglia from swelling (FIG. 3) and thus can reduce physical disruption of the blood-brain barrier caused by such swelling in the early stages post-stroke and mitigate the subsequent spread of damage.

FIG. 3 illustrates the protective effect of bumetanide on astroglial swelling in primary hippocampal cultures (14-15 days in vitro) after exposure to 50% hypotonic saline at time zero. Plot (left): Cell area visualized by phase contrast microscopy, standardized to the initial volume quantified by Scion Image (NIH) software. Images (right): Glial cells (arrows) with bumetanide treatment before hypotonic saline (top) and at 15 s (bottom) in 50% hypotonic saline.

Although the protective effect of bumetanide in brain edema had been previously reported in the literature (Lam et al., 2005), this effect was interpreted as block the Na—K—Cl cotransporter, not by altering kidney function, but instead probably by acting on transport mechanisms in blood-brain barrier. In these studies, it was noted that both intact and nephrectomized rats experienced reduced brain edema in a model of middle cerebral artery occlusion (MCAO) and that the 30-mg/kg dose of bumetanide used was higher than the normal pharmacologic dose for use as a diuretic." Nonetheless, this dose of bumetanide effectively reduced ischemia-induced cerebral edema in rats subjected to middle cerebral artery occlusion. O'Donnell and colleagues (O'Donnell et al., 2004) also used magnetic resonance diffusion-weighted imaging studies to show that intravenous bumetanide reduced edema formation within the first 3 hours of MCAO-induced cerebral ischemia. The protective effect was observed in nephrectomized rats, and thus was not due indirectly to renal diuresis. Bumetanide was effective at doses as low as 7.6 mg/kg.

Anatomical measures of infarct size, brain volume, neurological assessments, and mortality rate can be used to assess the consequences of middle cerebral artery occlusion (MCAO) model in mice. The rodent MCAO model, an accepted model of cerebral ischemia and reperfusion (Clark et al., 1997), uses a silicone-coated filament to promote cerebral artery occlusion (Migliati et al., 2001). An innovative method to measure effective occlusion in real time is by laser Doppler monitoring of blood flow rate FIG. 4 shows the Doppler laser measures of blood flow rate before, during and after imposition of ischemic stroke by middle cerebral artery occlusion in a male control mouse.

Typical procedure for MCAO model in mice: Wild-type C57BL/6J male mice at 9-11 weeks old are anesthetized, and cerebral blood flow is recorded as baseline using laser Doppler. The monofilament is placed in the internal common carotid and advanced to the ostia of the middle cerebral artery. Filament placement is considered successful with ≥75% reduction in cerebral blood flow. The Doppler flow tracing in FIG. 4 indicates that >80% reduction in cerebral blood flow was sustained for the full period (~60 min) of ischemia. After 1 h of ischemia, reperfusion is initiated by retraction of the filament and blood flow returns toward baseline. After 24 h, animals are evaluated for neurological, behavioral, and general deficits, and then sacrificed for anatomical analysis of the infarcted and contralateral control hemispheres. The standard procedure is summarized in FIG. 5 which provides a schematic illustration of the timeline for the standard in vivo experimental protocol.

FIG. 6 illustrates cerebral edema and infarct size in mice subjected to one hour of ischemia and 24 hours of reperfusion, with and without bumetanide (60 mg/kg) administered intravenously in a single bolus at 10 min before reperfusion. Stained with 2% TTC, the infarcted area is white; areas are analyzed using morphometric software by researchers blinded to the treatment group. Statistical significance ($p<0.06$) does not meet criteria, but indicates promise, and may be confirmed as the n value is increased.

The protective effect of the demonstrated AQP4 blocking agent, bumetanide, in vivo is consistent with the reduction in edema observed in ASP4 knock-out mice.

FIG. 6 illustrates cerebral infarcts in brains of MCAO mice after 1 h occlusion and 24 h reperfusion, without (control) and with bumetanide (60 mg/kg) applied 10 min before initiation of reperfusion. (A) Summary histogram of infarct areas. (B) Images of four sliced brains with infarct areas visualized by lack of dye (TTC) staining.

Preparation of Analogs of Bumetanide, Furosemide and Related Compounds.

Ester, Amide, and Sulfonamide Derivatives of Bumetanide as AQP Modulators: Esters of bumetanide can be prepared in two ways. The first method is treatment of bumetanide with diazoalkanes such as diazomethane, diazoethane, and the like, Scheme 1. For example, titration of bumetanide with one equivalent of diazomethane yields methyl ester 1. However, prolonged treatment with excess diazomethane ($R^1R^2C=CH_2$) or other diazoalkane (path a) results in conversion of the sulfonamide function to N-substituted- and N,N-disubstituted-bumetanide methyl ester derivatives 2 and 2b, respectively. In another method (path b), methyl ester 1 is treated with an alkyl halide or equivalent of general formula $R^1R^2CH-X$ in the presence of a non-nucleophilic base such as potassium t-butoxide or sodium hydride in an appropriate solvent such as dimethylformamide (DMF) to yield sulfonamide esters of general formula 2. Subsequent saponification of 2 with LiOH affords alkyl sulfonamide bumetanide analog 3. Formation of ester and amide derivatives of acid 3, as outlined in Scheme 2, is used to prepare additional esters, amides, and prodrugs of structure 4.

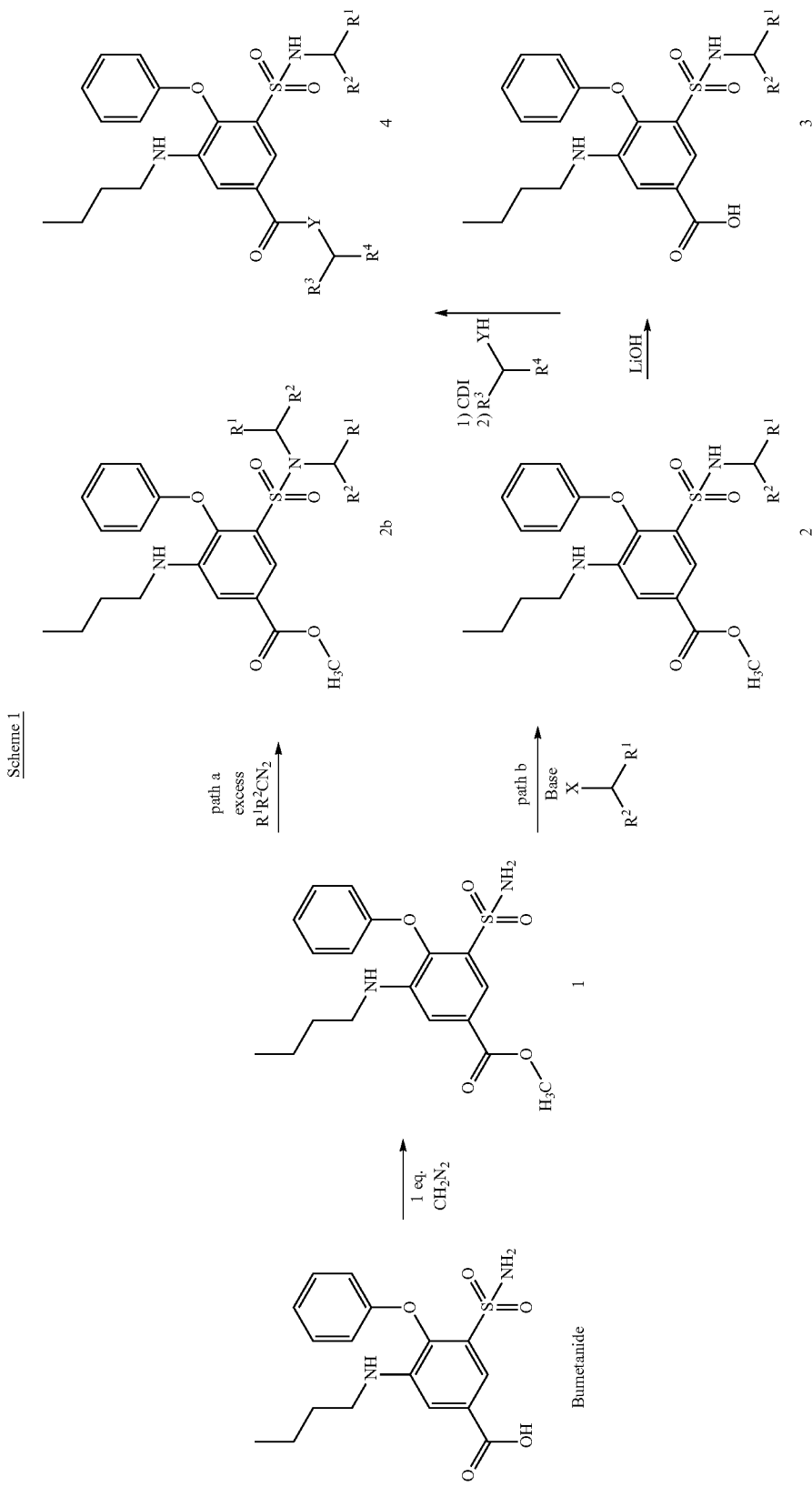
Scheme 1

Alternatively, bumetanide can be treated with carbonyl diimidazole (CDI) and the resulting imidazolide 4 can be reacted with an alcohol to cleanly form the ester 5, Scheme 2-path a.

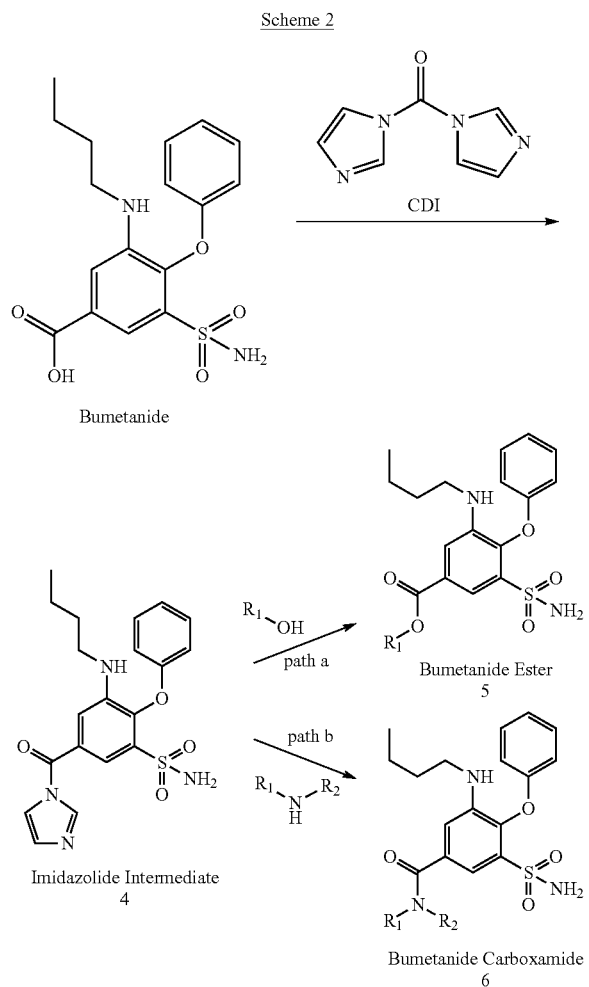

Conversely, treatment of imidazolide intermediate 4 with an primary or secondary amine yields the corresponding carboxamide derivative 6, Scheme 2-path b.

Preparation of Ring Substituted Derivatives of Bumetanide as AQP Modulators:

The preparation of ring substituted derivatives of bumetanide has been well documented (Feit, J. Med. Chem. 1970, 13(6) 1071-1075, J. Med. Chem. 1971, 14(2) 432-439) as well as closely related 3,4-disubstituted 5-sulfamoylbenzoic acids (Nielsen, J. Med. Chem. 1973, 16(10) 1170-1177, J. Med. Chem. 1974, 18(1) 41-50; Feit, J. Med. Chem. 1974, 17(6) 572-578). The general approach to these derivatives is outlines in Scheme 3. In this simple process, commercially available 4-chloro-3-nitro-5-sulfamoylbenzoic acid 1 is treated with a nitrogen, oxygen, or sulfur nucleophile ($R^1XH$), with or without addition of a non-nucleophilic base, to produce the nucleophilic aromatic substitution product 2. Reduction of the nitrogroup can be affected using a variety of standard conditions well known in the art including catalytic hydrogenation, the action of $Na_2S_2O_4$, and the action of stannous chloride. The resulting aniline derivative 3 may, then be either reductively alkylated with an aldehyde ($R^2CHO$) in the presence of a reducing agent such as $NaBH_3CN$, $NaBH(OAc)_3$, or catalytic hydrogenation to give the desired 4-$R^1$X-3-$R^2$NH-5-sulfamolybenzoic acid 4a (path a). Alternatively, aniline intermediate 3 may be alkylated with an appropriate alkyl halide in the presence or absence of base to yield the acid product 4b or the corresponding ester 5 or a mixture of both (path b). An ester of structure 5 may be converted to the corresponding acid 4b by saponification with LiOH or acid hydrolysis with aqueous HCl. Analines of general structure 3 may also be converted to carboxamides 4c or sulfonamides 4d upon treatment with carboxylic acid halides (path c) or sulfonyl halides (path d) respectively.

Bumetanide derivatives outlined in Scheme 3 can be further modified as outlined in Schemes 1 and 2 to ester, prodrug, carboxamide, and sulfonamide derivatives of general structure 6, Scheme 3.

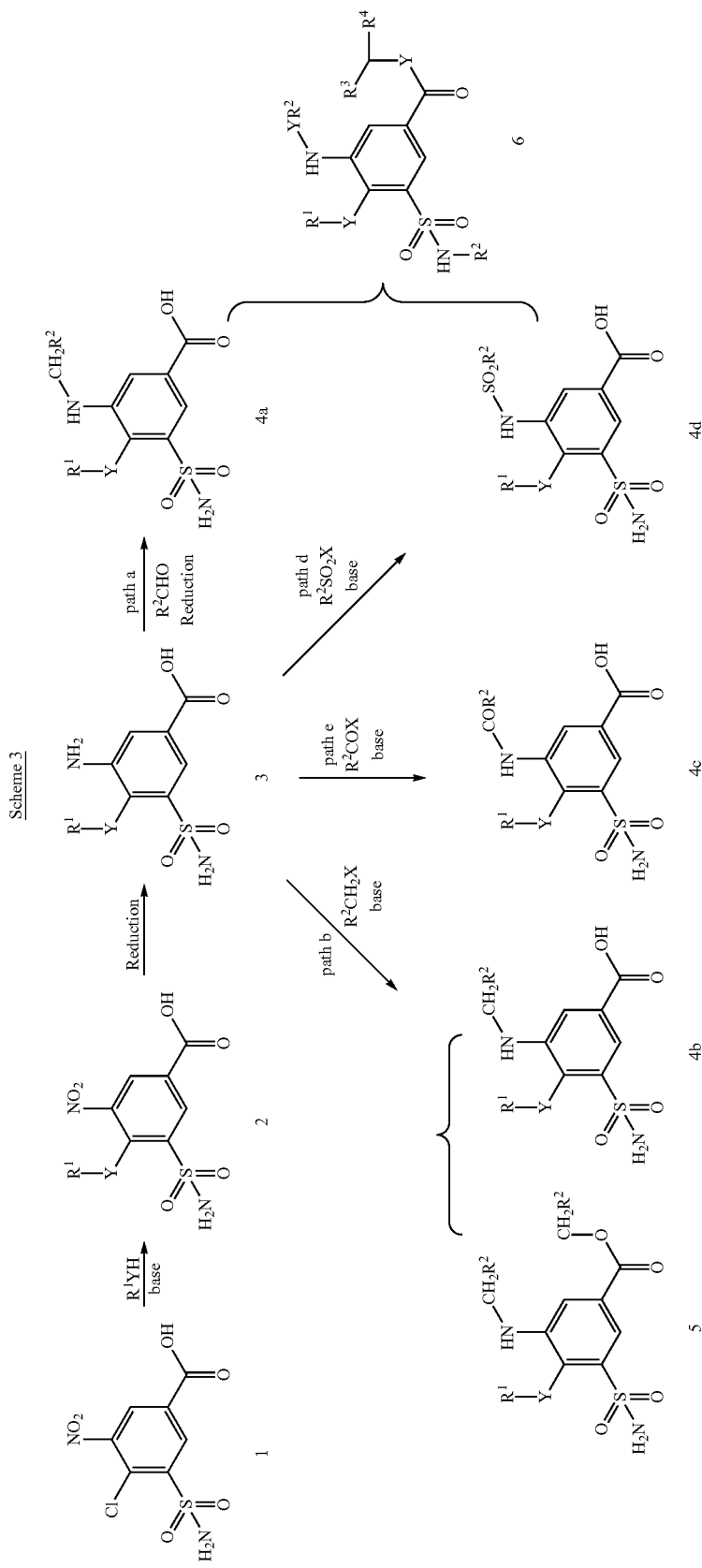
Scheme 3

Preparation of Ester and Prodrug Derivatives of Furosemide as AQP Modulators:

Esters of furosemide can be prepared in two ways. The first method is treatment of furosemide with diazoalkanes such as diazomethane, diazoethane, diazodiphenylmhnethane, ethyl diazoacetate, and the like, Scheme 4-path a. For example, titration of furosemide with one equivalent of diazoalkane yields ester 1. Alternatively, furosemide can be treated with carbonyl diimidazole (CDI) and the resulting imidazolide 2 can be reacted with an alcohol to cleanly form the ester 1, Scheme 4-path b.

Scheme 4
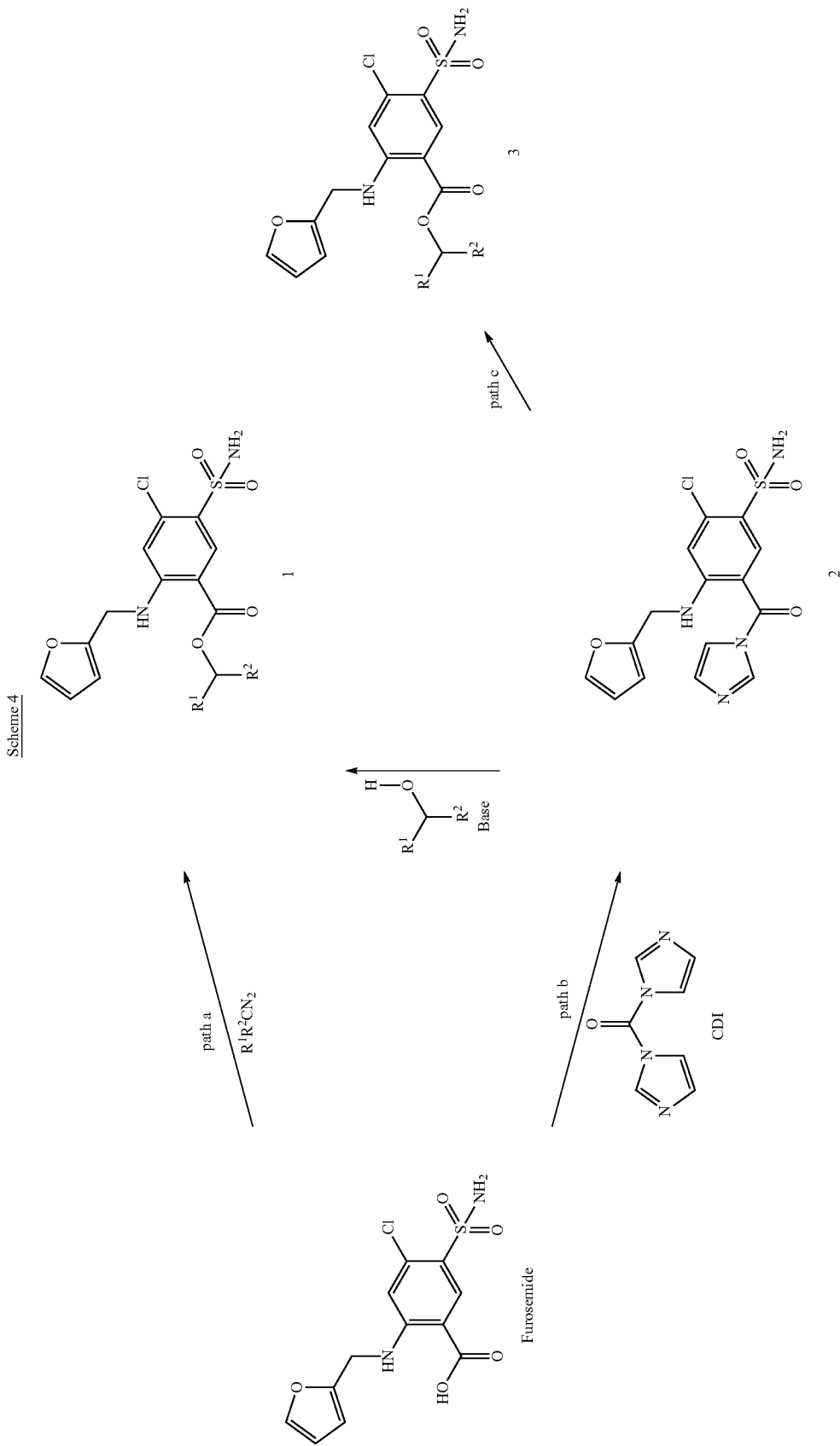

Preparation of Amide Derivatives of Furosemide as AQP Modulators:

Conversely, treatment of imidazolide intermediate 2 with an primary or secondary amine yields the corresponding carboxamide derivative 4, Scheme 4-path C.

Preparation of Sulfonamide Derivatives of Furosemide as AQP Modulators:

Sulfonamide derivatives of furosemide can be prepared by two methods. In the first method, prolonged treatment of furosemide methyl ester 1 with excess diazoalkane reagents results in conversion of the primary sulfonamide function to N-alkyl-sulfonamide 2 along with smaller amounts of N,N-alkyl-sulfonamide products, Scheme 5-path a. Subsequent saponification with LiOH afforded alkyl sulfonamide furosemide analog 3. Alternatively, the methyl ester 1 can be treated with an alkyl halide and a non-nucleophilic base to form N-alkyl-furosemide derivatives 2, Scheme 5-path b.

Formation of ester and amide derivatives of acid 3, as outlined in Scheme 2, is used to prepare additional esters, amides, and prodrugs of structure 4.

zoic acids is well documented (Sturm, Chemische Berichte 1966, 99(1), 328-344; Feit, J. Med. Chem. 1972, 15(1), 79-83, J. Med. Chem. 1973, 16(2), 127-130). Depending on the substitution pattern desired, the appropriate commercially available 2,4-dihalo-5-sulfamoylbenzoic acid can be used to achieve the desired order of addition selectivity during single or tandem nucleophilic aromatic substitution reactions, Scheme 6. Whereas 2,4-dichloro-5-sulfamoylbenzoic acid 1 provides selectivity for substitution at the 2-position (path a) and the initial product 4 may be driven to the bis-substitution product 1 under conditions of high temperature and extended reaction times (path d), the 2-addition product 6 (path b) or bis-substitution and tandem addition products 2 (path e) can more easily be achieved using 2,4-difluoro-5-sulfamoylbenzoic acid 2 as the starting material (path b). Alternatively, 4-substitution products 8 can be selectively achieved (path c) using 2-chloro-4-fluoro-5-sulfamoylbenzoic acid 3 as the starting material. A second nucleophile can be sequentially added to intermediate 8 to provide variations 9 on this 2,4-bis-substitution pattern (path f).

Scheme 5

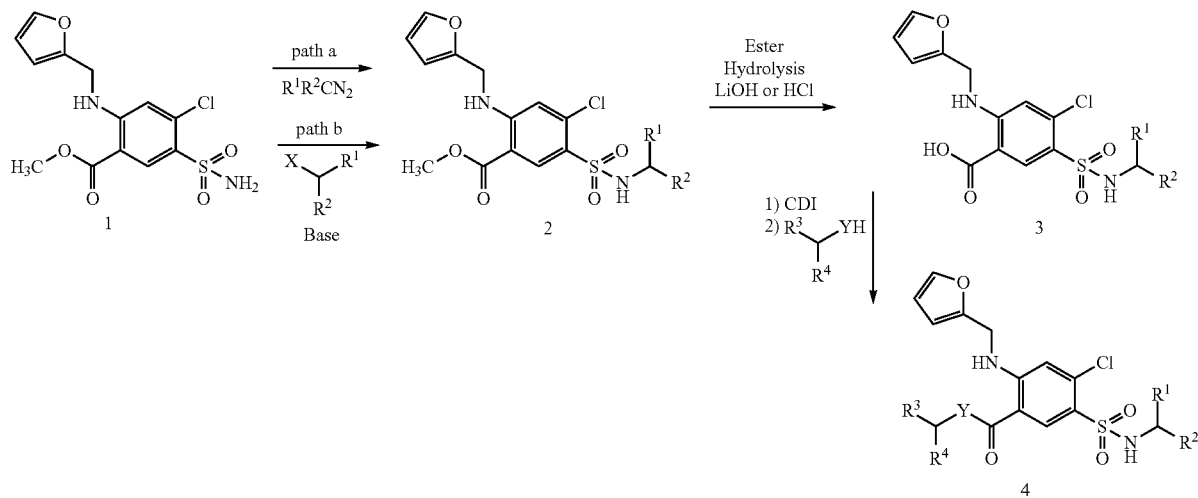

Preparation of Ring Substituted Derivatives of Furosemide as AQP Modulators:

Methods for the preparation of ring-substituted derivatives of furosemide and other 2,4-disubstituted 5-sulfamoylben- Formation of ester and amide derivatives of carboxylic acids, as outlined in Scheme 2, is used to prepare additional esters, carboxamides, and prodrugs of structure 4.

Scheme 6

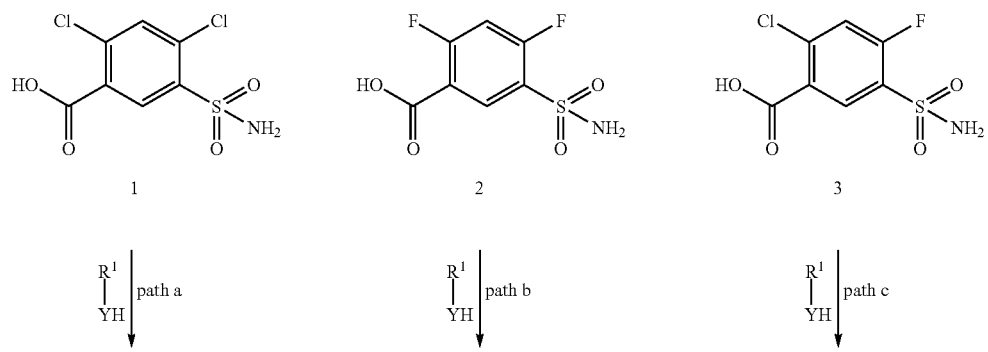

33

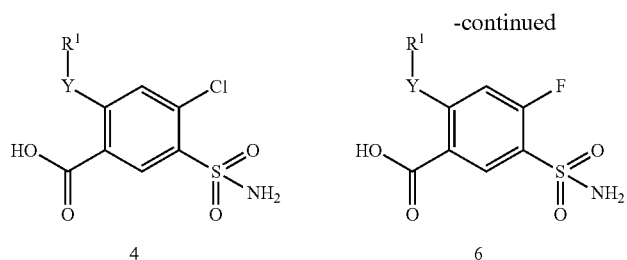

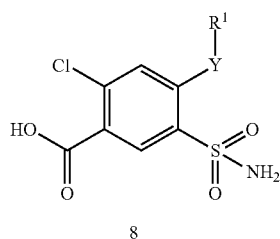

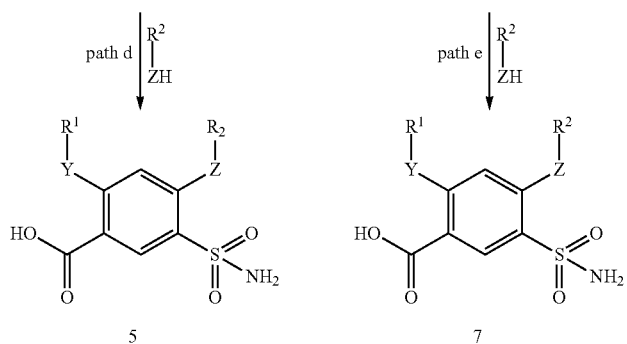

In one rescaffolding strategy, the 2,4-disubstituted-5-sulfamoylbenzoic acid scaffold is replaced by the 2-substituted-5-sulfamoyl-pyridine-3-carboxylic acid scaffold. Preparation of a versatile intermediate, Ethyl 2-Chloro-5-chlorosulfonyl-nicotinoate 4, from 2-hydroxynicotinic acid J scaffold has been described (Dunn, 2001). In this procedure, Scheme 7, 2-hydroxynicotinic acid is treated with fuming sulfuric acid to yield sulfonic acid 2 which upon refluxing in ethyl alcohol provided the ethyl ester 2. Treatment of 3 with sulfuryl chloride ($SOCl_2$) key 5-chlorosulfonyl intermediate 4. Treatment of sulfonyl chloride 4 with ammonia, a primary amine, or a secondary amine gives the corresponding sulfonamide 5. Treatment of sulfonamide 5 with a second nucleophile provides 6 via nucleophilic substitution at the 2-chloropyridine function. Reaction of 2-chloropyridines is well known to occur with oxygen, nitrogen, and sulfur nucleophiles (Z=O, NR, or S).

Formation of ester and amide derivatives of acid 7, as outlined in Scheme 2, is used to prepare additional esters, amides, and prodrugs.

Scheme 7

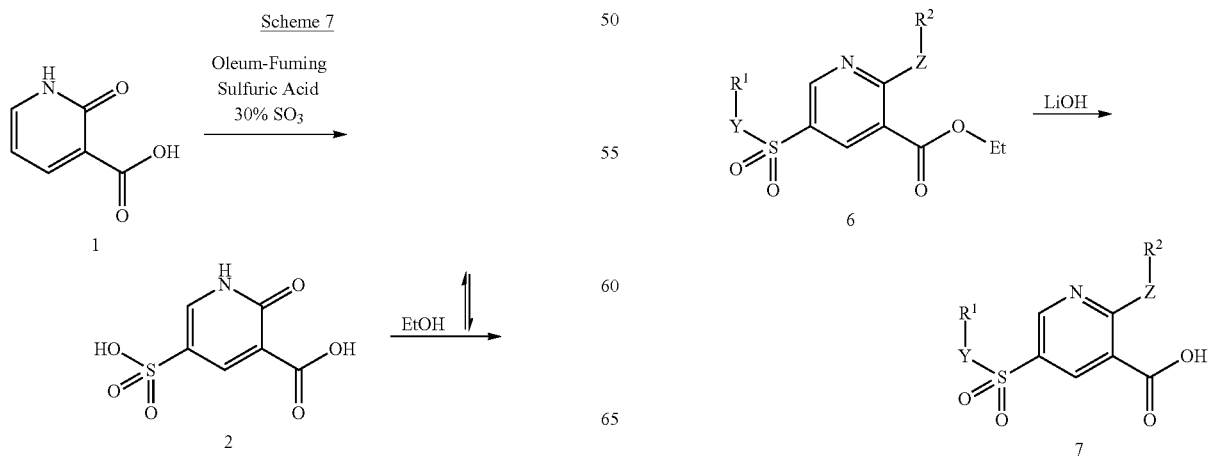

Process for the Preparation of Pyrazolopyrimidinones. Dunn P J, Dunn C, WO-01982

In a second rescaffoling strategy, the central 6-membered ring in bumetanide or furosemide is replaced by a 5 membered heterocyclic ring system as outlined in Scheme 8. In route A, the commercially available 4-thiazolecarboxylic acid 1 is converted to its ethyl ester 2 via an cyclic carmbamic anhydride intermediate. Reductive amination of the amino function with an appropriate aryl or alkyl aldehyde to give intermediate 3. Oxidization of 3 to a sulfonyl chloride is performed by methods known in the art such as sodium hypochlorite and this material is then reacted with an amine to yield sulfonamide 4. If desired the ethyl ester function of 4 can be hydrolyzed under acidic or alkaline conditions to yield acid 5.

In a related process, Scheme 8 route B, commercially available 5-amino-2-methylsulfanyl-1,3-thiazole-4 carboxylate 6 is reductively alkylated with and appropriate aryl or alkyl aldehyde by methods well known in the art to yield intermediate 7. Oxidation of 7 with meta-chloro-peroxybenzoic acid (MCPBA) would yield sulfone ester 8 that can optionally be saponified to the sulfone acid 9.

As described previously, formation esters and carboxamides of acids 5 and 2, as outlined in Scheme 2, is used to prepare additional ester, amide derivatives and prodrugs.

Scheme 8

Route A

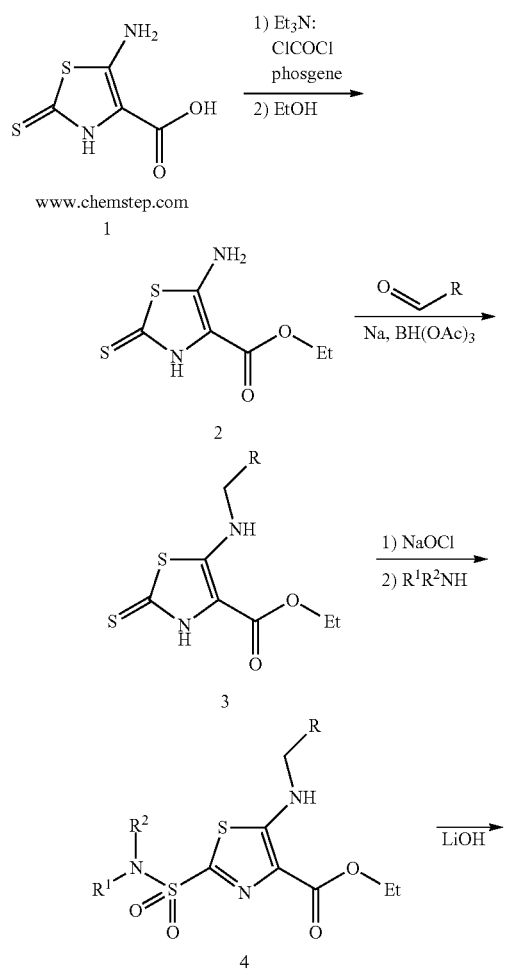

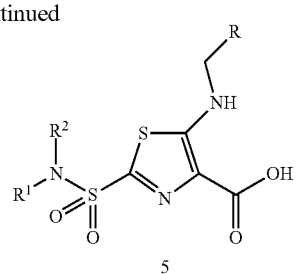

Route B

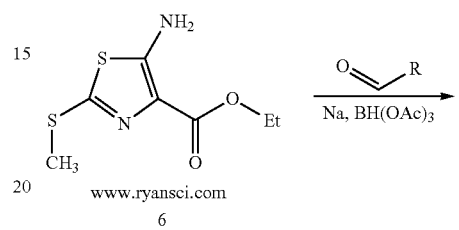

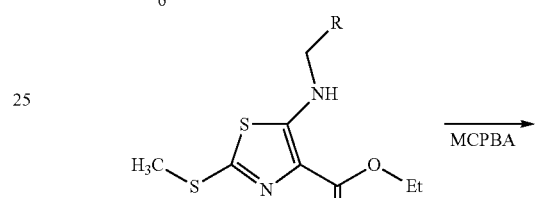

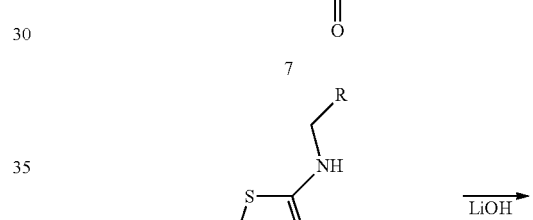

A convenient preparation of heteroaryl sulfonamides and sulfonyl fluorides from heteroaryl thiols. Wright, S W.; Hallstrom, K N. Journal of Organic Chemistry 2006, 71(3), 1080-1084.

Similar rescaffolding approaches can be used to gain access to other five membered heterocyclic scaffolds, Scheme 9. In this case, a commercially available 2-sulfamoyl-imidazole-4-carvoxylic acid 1 is converted to its ester 2 and the reacted with an appropriate alky or arylalkyl halide in the presence of 2 equivalents of strong based to yield the N-alkylated products 3 and 4. Ester hydrolysis 3 and 4 can optionally be achieved under either acidic or alkaline conditions to yield acids 5 and 6 respectively.

As described previously, formation esters and carboxamides of acids 5 and 6, as outlined in Scheme 2, is used to prepare additional ester, amide derivatives and prodrugs.

Scheme 9

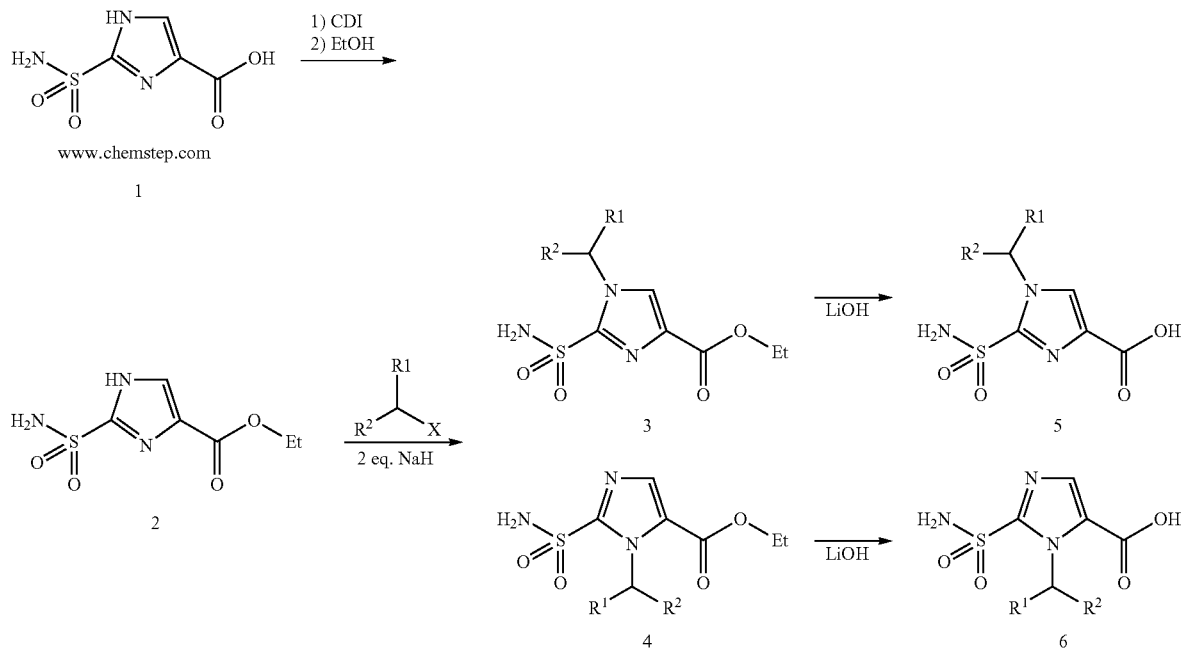

Another rescaffolding approaches can be used to gain access to other five membered heterocyclic scaffolds, Scheme 10. In this case, commercially available 2-chloro-5-nitro-benzenesulfonamide undergoes nucleophilic aromatic substitution with and appropriate alcohol, amine, or thiol to yield 2. Reduction of the nitro group is affected by methods previously described the resulting aniline is optionally coupled to a carboxylic acid derivative, isocyanate, isothiocyanate, carbamoyl chloride, or sulfonyl chloride to yield carboxamide 4, urea 5, thiourea 6, carbamate 7, or sulfonamide 8 respectively.

Furosemide can also be reacted with reagents to form bicyclic scaffolds of interest, Scheme 11. For example, Furosemide is known to react with formamide in the presence of phosphorousoxy chloride or under microwave assistance (Alexandre 2002), path a, to yield quinaolin-4-one derivative 1. Alternatively, furosemide can react in the presence of acid with an aldehyde 2 under dehydrating conditions, an acetal or ketal 3 and enol ether 4, or enol ester 5 to yield heterocycles of general structure 6 and 7, path b. these later agents may act directly on the aquaporin channels or act as prodrugs the deliver furosemide more effectively to the target binding site.

Scheme 10

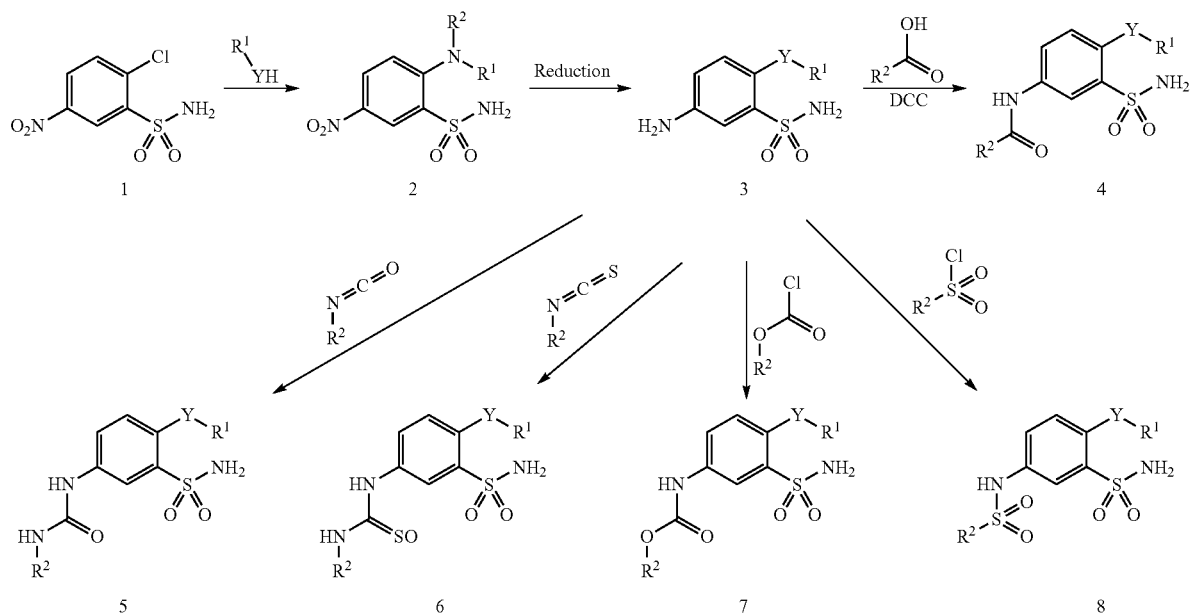

Scheme 11
path a
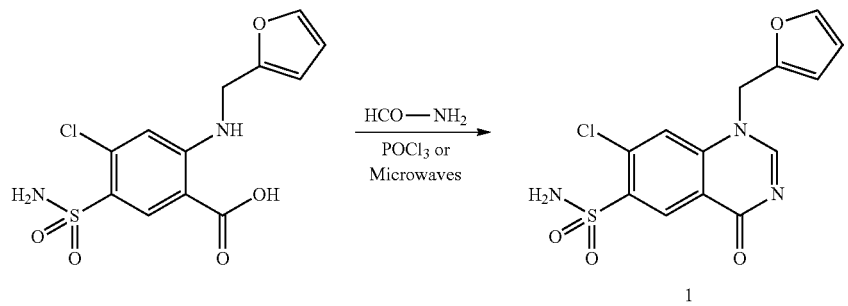
path a
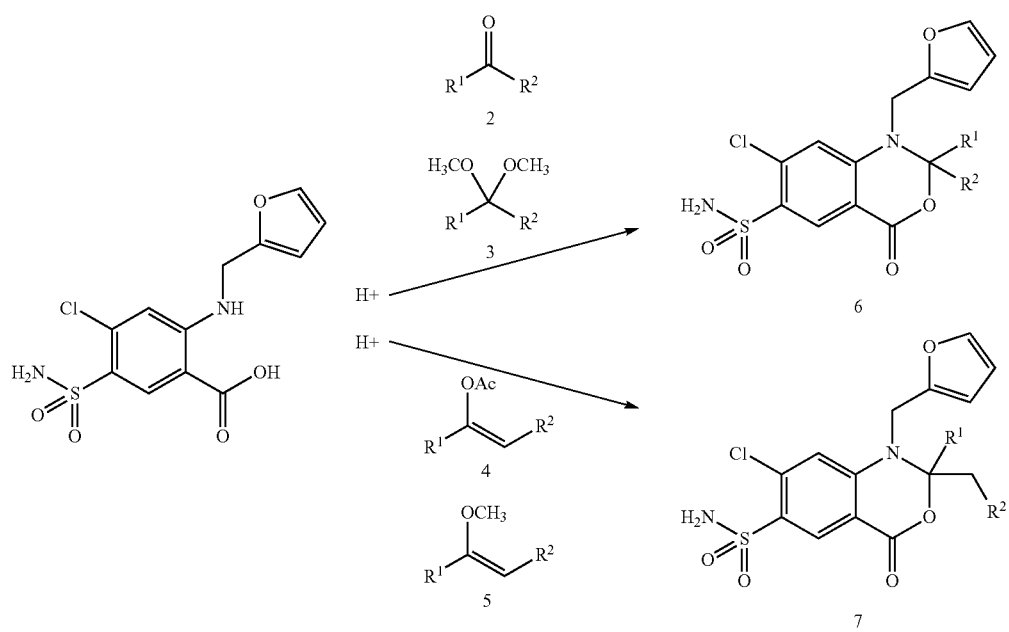
2. Preparation of AQP-0001 (Structure-A), AQP-0002 (Structure-B), AQP-0005 (Structure-C)
Reaction
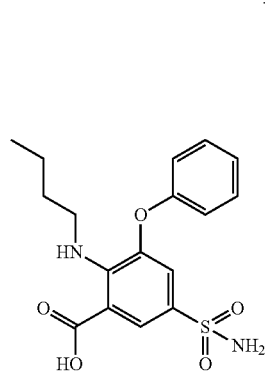
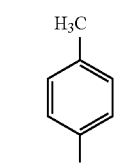
1) Diazald in EtOH/DCM added to:
   aq. KOH in EtOH @ 85°
   CH₂Cl₂ distill
2) Add to Bumetanide
-continued
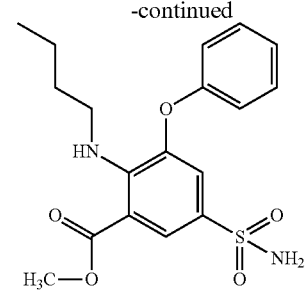
A
+
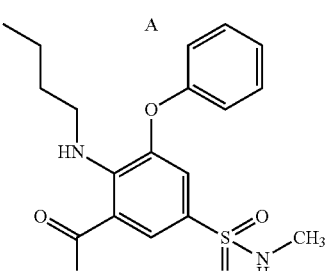
B
+

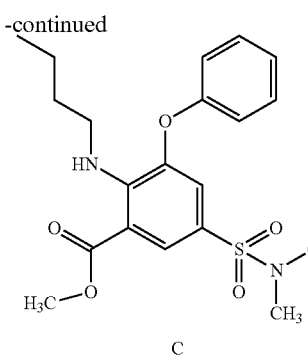

C

Reaction Conditons:

| | |
|---|---|
| Reaction Molarity | 10 equivalents |
| Pressure | Atm |
| Temperature | 25 deg C. |

Reactants:

| | Reactant | MF | Limit? | MW | Eq | Moles (mmol) | Sample Mass (mg) | Vol | Molarity | d | % Wt | FM (g/mol) | Reactant Mass (mg) |
|---|---|---|---|---|---|---|---|---|---|---|---|---|---|
| 1 | | C17H20N2O5S | Yes | 364.416 | 1.000 | 1.0 | 364 | | | | | 364 | 364 |
| 2 | Diazald | C8H10N2O3S | No | 214.242 | 10.000 | 10.000 | 2142 | | | | | 214 | 2142 |

Solvents:

| | Name | Solvent Ratio | Volume (ml) |
|---|---|---|---|
| 1 | Dichloromethane | | 12 |

Products:

| | Product | MF | Actual Mass (mg) | Actual Mol (mmol) | Yield (%) | Purity | MW | Eq | Theo Mol (mmol) | Theo Mass (mg) | FM (g/mol) |
|---|---|---|---|---|---|---|---|---|---|---|---|
| 1 | Methyl Estere | C18H22N2O5S | 160 | 0.423 | 42.3 | | 378.443 | 1.000 | 1.000 | 378 | 378 |
| 2 | Ester MeAmide | C19H24N2O5S | 110 | 0.280 | 28.0 | | 392.469 | 1.000 | 1.000 | 392 | 392 |
| 3 | Ester Me2Amide | C20H26N2O5S | 20 | 0.049 | 4.92 | | 406.496 | 1.000 | 1.000 | 406 | 406 |

Preparation:

To a solution of 8 gm KOH in 6 ml water and 6 ml EtOH in a 100 ml RBF equipped with teflon joint distillation head, chilled condenser with receiving flask in an ice-water bath, and addition funnel was added 10 ml of DCM and the two phase system was heated to 85° C. Once distillation had initiated, a solution of 2.14 g (10 mmol) Diazald in 10 ml DCM and 5 ml EtOH was added over 15 min. Once the distillation solution was not yellow, the resulting yellow distillate was stoppered and stored in an ice bath till used.

Two 50 ml Erlenmeyer flasks were prepared with 184 mg (0.5 mmol) of Bumetanide for two experiments. The first flask was treated with $CH_2N_2$ solution until a faint yellow color persisted, gas evolution was observed. The second flask was treated with the remaining $CH_2N_2$ solution, gas evolution was observed, stoppered loosely and allowed to stand over the weekend.

After 72 hrs, the first solution had evaporated and a solid remained. The second solution had a faint yellow tint still. TLC indicated that the first flak contained a nearly pure product while the second flask contained mostly a less polar product long with traces of a third even less polar product. The solid contents of the first flask, which is expected to contain primarily the bumetanide methyl ester, was taken up in 1.5 ml of $CHCl_3$ with mild heating and dilute with ~6 ml of hexanes. Crystals formed which were collected by filtration to give: 144 mg of white flakes.

The mother liquors were combined with the products in the second flask and chromatographed on al cm Biotage samplet guard column and chromatographed using a Si-12+M (160 mm) cartridge. The chromatogram is given below: Fractions 15-17 gave product-C(20 mg), 18-22 gave major product-B (110 mg), and 24+25 gave product-A (20 mg).

Product yields were: (140+20)=160 mg (A), 110 mg (B), and 20 mg (C); AQP-0001, AQP-0002, AQP-0005 respectively.

(A) NMR AQP-0001

$^1$HNMR (300 MHz, $CDCl_3$) 0.80 ppm (t, J=10 Hz, 3H), 1.19 ppm (m, 2H), 1.45 ppm (m, 2H), 2.68 ppm (bs, 1H), 3.14 ppm (q, J=6.6, 2H), 3.91 ppm (t, J=6.6 Hz, 1H), 4.1 ppm (s, 3H), 4.98 ppm (s, 1H), 6.92 ppm (d, J=7.8 Hz, 2H), 7.03 ppm (t, 7.2 Hz, 1H), 7.34 ppm (d, J=7.8 Hz, 1H), 7.43 ppm (t, 7.21 Hz, 1H), 7.55 ppm (s, 1H), 7.98 ppm (s, 1H)

13CNMR (75 MHz, $CDCl_3$) 14.02, 20.16, 31.32, 43.05, 52.89, 55.23, 115.72, 116.76, 117.07, 124.20, 128.40, 130.51, 136.45, 140.19, 142.59, 156.07, 166.35.

(B) NMR AQP-0002

$^1$HNMR (300 MHz, $CDCl_3$) 0.80 ppm (t, J=10 Hz, 3H), 1.19 ppm (m, 2H), 1.45 ppm (m, 2H), 2.55 ppm (d, J=5 Hz, 3H), 3.14 ppm (q, J=6.6, 2H), 3.91 ppm (t, J=6.6 Hz, 1H), 4.1 ppm (s, 3H), 4.98 ppm (s, 1H), 6.92 ppm (d, J=7.8 Hz, 2H), 7.03 ppm (t, 7.2 Hz, 1H), 7.34 ppm (d, J=7.8 Hz, 1H), 7.43 ppm (t, 7.2 Hz, 1H), 7.55 ppm (s, 1H), 7.98 ppm (s, 1H)

13CNMR (75 MHz, $CDCl_3$) 14.02, 20.16, 29.98, 31.32, 43.05, 52.89, 55.23, 115.72, 116.76, 117.07, 124.20, 128.40, 130.51, 136.45, 140.19, 142.59, 156.07, 166.35.

(C) NMR AQP-0005

¹HNMR (300 MHz, CDCl₃) 0.80 ppm (t, J=10 Hz, 3H), 1.19 ppm (m, 2H), 1.45 ppm (m,2H), 2.78 ppm (s, 6H), 3.14 ppm (q, J=6.6, 2H), 3.91 ppm (t, J=6.6 Hz, 1H), 4.1 ppm (s, 3H), 4.98 ppm (s, 1H), 6.92 ppm (d, J=7.8 Hz, 2H), 7.03 ppm (t, 7.2 Hz, 1H), 7.34 ppm (d, J=7.8 Hz, 1H), 7.43 ppm (t, 7.2 Hz, 1H), 7.55 ppm (s, 1H), 7.98 ppm (s, 1H)

13CNMR (75 MHz, CDCl₃) 14.04, 20.19, 31.35, 37.83, 43.45, 52.85, 55.23, 115.72, 116.76, 117.07, 124.20, 128.40, 130.51, 136.45, 140.19, 142.59, 156.07, 166.35.

3. Preparation of AQP-0003

Reaction

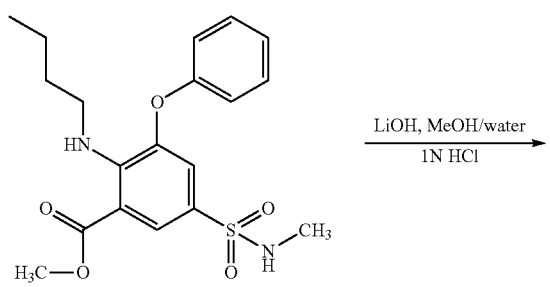

LiOH, MeOH/water
1N HCl

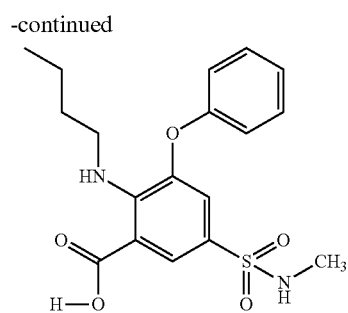

Reaction Conditions:

| | |
|---|---|
| Reaction Molarity | Excess |
| Pressure | Atm |
| Temperature | 25 dec C. |

Reactants:

| Reactant | MF | Limit? | MW | Eq | Moles (μmol) | Sample Mass (mg) | Vol | Molarity | % d Wt | FM (g/mol) | Reactant Mass (mg) |
|---|---|---|---|---|---|---|---|---|---|---|---|
| 1 | C19H24N2O5S | Yes | 392.469 | 1.000 | 178 | 70 | | | | 392 | 70.0 |

Solvents:

| | Name | Solvent Ratio | Volume (mL) |
|---|---|---|---|
| 1 | Methanol Water | 100% | 3 |

Products:

| Product | MF | Actual Mass (mg) | Actual Mol (μmol) | Yield (%) | Purity | MW | Eq | Theo Mol (μmol) | Theo Mass (mg) | FM (g/mol) |
|---|---|---|---|---|---|---|---|---|---|---|
| 1 | C18H22N2O5S | 70 | 185 | 104 | | 378.443 | 1.000 | 178 | 67.5 | 378 |

Preparation:

A mixture of 70 mg (0.18 mmol) ester and 42 mg (1.0 mmol) LiOH.H₂O in 2 ml 3:1 MeOH/water was stirred at RT for 24 hrs. 1.0 ml of 1N HCl was added and the white precipitate was filtered and suction dried to give 70 mg of product. ¹H NMR gaf_2005_36_1 and ¹³C NMR gaf_2005_36_2 were consistent with the desired product. Yield was essentially quantitative. Compound was registered as BIO5_AQP_GAF_003_01.

NMR AQP-0003

¹HNMR (300 MHz, CDCl₃) 0.80 ppm (t, J=10 Hz, 3H), 1.19 ppm (m, 2H), 1.45 ppm (m,2H), 2.55 ppm (d, J=5 Hz, 3H), 3.14 ppm (q, J=6.6, 2H), 3.91 ppm (t, J=6.6 Hz, 1H), 4.98 ppm (s, 1H), 6.92 ppm (d, J=7.8 Hz, 2H), 7.03 ppm (t, 7.2 Hz, 1H), 7.34 ppm (d, J=7.8 Hz, 1H), 7.43 ppm (t, 7.2 Hz, 1H), 7.55 ppm (s, 1H), 7.98 ppm (s, 1H)

13CNMR (75 MHz, CDCl₃, DMSO-d₆) 13.90, 19.98, 29.56, 31.13, 43.17, 115.56, 116.87, 117.07, 118.70, 123.48, 128.26, 130.24, 133.08, 140.16, 142.50, 156.34, 167/60.

4. Preparation of AQP-0004

Reaction

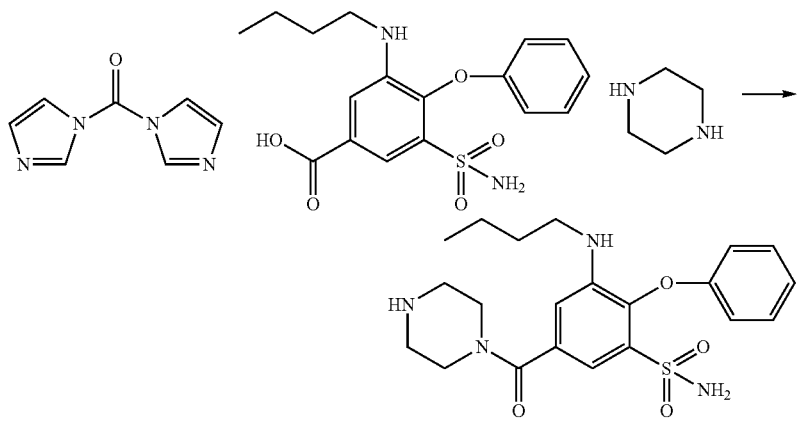

Reaction Conditions:

| | |
|---|---|
| Reaction Molarity | |
| Pressure | Atm |
| Temperature | Heat then RT |

Reactants:

| | Reactant | MF | Limit? | MW | Eq | Moles (mmol) | Sample Mass (g) | Vol | Molarity | % d Wt | FM (g/mol) | Reactant Mass (g) |
|---|---|---|---|---|---|---|---|---|---|---|---|---|
| 1 | CDI | C7H6N4O | No | 162.149 | 1.200 | 0.600 | 0.097 | | | | 162 | 0.097 |
| 2 | | C17H20N2O5S | Yes | 364.416 | 1.000 | 0.5 | 0.182 | | | | 364 | 0.182 |
| 3 | | C4H10N2 | No | 86.136 | 2.000 | 1.000 | 0.086 | | | | 86 | 0.086 |

Solvents:

| | Name | Solvent Ratio | Volume (ml) |
|---|---|---|---|
| 1 | Ethyl Acetate | | 4.0 |

Products:

| | Product MF | Actual Mass (g) | Actual Mol (mmol) | Yield (%) | Purity | MW | Eq | Theo Mol (mmol) | Theo Mass (g) | FM (g/mol) |
|---|---|---|---|---|---|---|---|---|---|---|
| 1 | C21H28N4O4S | 0.150 | 0.347 | 69.4 | | 432.536 | 1.000 | 0.500 | 0.216 | 433 |

Preparation:

To a 10 mil RBF containing a magnetic stirring bar was added Bumetanide (162 mg, 0.50 mmol) and 3.0 ml EtOAc. The mixture was stirred under argon at 25 deg. C. and 97 mg (0.60 mmol) carbonyldiimidazole (CDI) was added. The mixture was heated with a hot air gun until homogeneous and then allowed to cool. Upon cooling, a new precipitate formed and TLC indicated a new less polar light blue fluorescent spot. After standing for 10 minutes, a solution of 86 mg (1.0 mmol) piperazine in 3 ml EtOAc was added. The mixture was broken up with a stirring bar and stirred overnight. A small aliquot of the reaction was poured into EtOAc (1 ml) in a 2-dram vial, washed with 2×1 ml water, shaken with 1 ml brine, and the organic layer analyzed bu TLC. TLC indicated no starting material remaining and a major more polar spot.

The solution was poured into water, extracted into 25 ml EtOAc, washed with water (2×20 ml) and brine (20 ml), then dried over MgSO4 and concentrated.

The crude product was purified by flash chromatography on 50 ml silica gel using 10% MeOH/DCM providing a clean separation of 150 mg of a light yellow foam (ca. 69% yield). NMR was consistent with the desired product. Sample was designated AQP-0004.

NMR AQP-0004

$^1$HNMR (300 MHz, CDCl$_3$) 0.80 ppm (t, J=10 Hz, 3H), 1.19 ppm (m, 2H), 1.45 ppm (m,2H), 3.0 ppm (bs, 4H), 3.14 ppm (q, J=6.6, 2H), 3.50 (bs, 2H), 3.80 (bs, 2H), 3.91 ppm (t, J=6.6 Hz, 1H), 6.92 ppm (d, J=7.8 Hz, 2H), 7.03 ppm (t, 7.2 Hz, 1H), 7.34 ppm (s, 2-H), 7.45 ppm (t, 7.2 Hz, 1H), 7.55 ppm (s, 1H)

13CNMR (75 MHz, CDCl$_3$) 14.02, 20.16, 29.98, 31.32, 43.05, 52.89, 55.23, 115.72, 116.76, 117.07, 124.20, 128.40, 130.51, 136.45, 140.19, 142.59, 156.07, 166.35.

FABMS 434 (M+H)$^+$; HRMS calcd for $C_{21}H_{29}N_4O_4S^+$ 433.19. found 433.40.

Reference: See Ford, R. A., et. al., J. Med. Chem. 1986, 29, 538-549 (page 548 prep of 9b);
also see Schoenfield, R. C. and Ganem, B., Tet. Lett., 1998, 39, 414704150

5. Preparation of AQP-0006

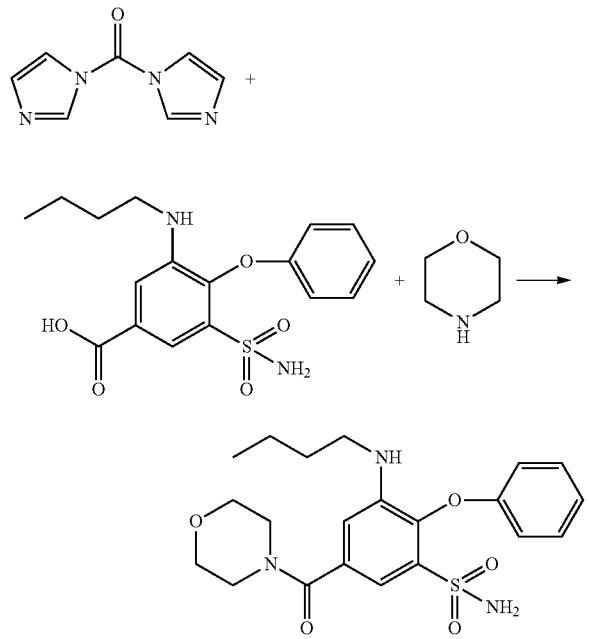

Reaction Conditions:

| | |
|---|---|
| Reaction Molarity | |
| Pressure | Atm |
| Temperature | Heat then RT |

Reactants:

| Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C7H6N4O | ☐ | 162.15 | 1.34 | 0.669 | 0.109 | | | | | 162.15 | 0.109 |
| 2 | C17H20N2O5S | ☑ | 364.42 | 1.00 | 0.499 | 0.182 | | | | | 364.42 | 0.182 |
| 3 | C4H9NO | ☐ | 87.12 | 2.24 | 1.119 | 0.097 | | | | | 87.12 | 0.097 |

Solvents:

| Name | Ratio | Volume |
|---|---|---|
| Ethyl Acetate | | |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C21H27N3O5S | 0.190 | 0.438 | 88 | | 433.52 | 1.000 | 0.499 | 0.217 | 433.52 |

Preparation:

To a 10 ml RBF containing a magnetic stir bar was added Bumetanide (182 mg, 0.5 mmol) in EtAOc (3 ml). Stirred this solution under argon. 1,1'-Carbonyldiimidazole (109 mg, 0.6 mmol) was added to the above solution and heated until homogeneous. Allowed the mixture to cool to room temperature. Upon cooling a white precipitate was formed. TLC on $SiO_2$ in 100% EtAOc against Bumetanide indicated a less polar spot.

Morpholine (97 mg, 1 mmol) was added to the above solution at room temperature using a pipet. Solution became homogeneous again. Stirred overnight. TLC on $SiO_2$ in 100% EtOAc indicated a less polar product.

Extracted the reaction mixture into 25 ml EtOAc. Washed with 2×20 ml distilled water and 20 ml brine. Combined the desired fractions and dried over anhydrous $MgSO_4$. Filtered and concentrated. Dissolved in the minimum amount of EtOAc and reprecipitated from hexanes. Filtered the precipitate and dried under vacuum.

$^1$H and 13C NMR in $CDCl_3$ with 2 drops of MeOD. Submitted for high resolution mass spec. Obtained a yield of 88% based on the limiting reagent, Bumetanide. Sample was designated NTF-2006-1-004A $^1$HNMR (300 MHz, $CDCl_3$) 0.81 (t, J=7.5 Hz, 3H), 1.18 (m, J=7.5 Hz, 2H), 1.41 (m, J=7.2 Hz, 2H), 3.05 (t, J=6.9 Hz, 2H), 3.75 (br m, 8H), 5.11 (s, 1H), 6.92 (br t, 1H), 6.95 (br d, J=1.5 Hz, 2H), 7.10 (t, J=7.5 Hz, 2H), 7.32 (td, J=9 Hz, 2H) 13C NMR (75 MHz, $CDCl_3$) 14.00, 20.17, 31.26, 43.27, 49.94, 67.22, 113.44, 114.74, 115.65, 124.14, 130.48, 133.68, 136.33, 156.16, 169.56

FABMS 434 $(M+H)^+$; HRMS calcd for $C_{21}H_{28}N_3O_5S^+$ 434.1750. found 434.1757.

6. Preparation of Imidazolide Intermediate

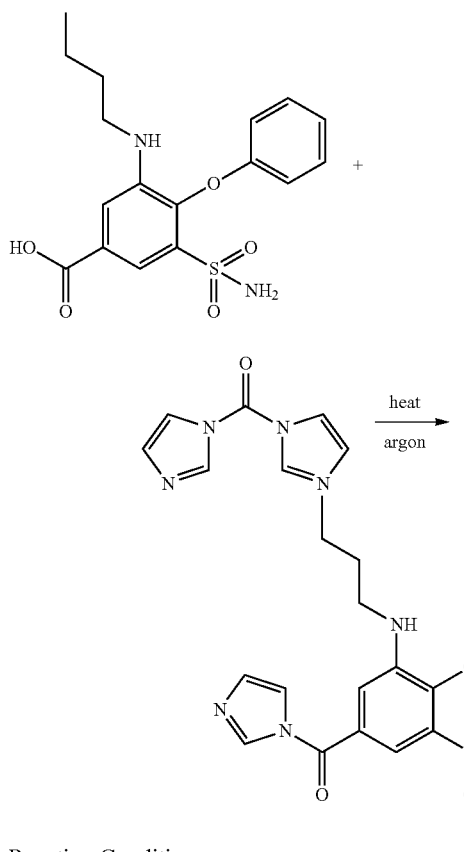

Reaction Conditions:

| | |
|---|---|
| Reaction Molarity | |
| Pressure | Atm |
| Temperature | 25 deg C. |

Reactants:

| Reactant | MF | Limit? | MW | Eq | Moles (mmol) | Sample Mass (mg) | Vol | Molarity | % Wt | FM | Reactant Mass (mg) |
|---|---|---|---|---|---|---|---|---|---|---|---|
| 1 | C17H20N2O5S | ☑ | 364.42 | 1.000 | 2.497 | 910 | | | | 364.42 | 910 |
| 2 | C7H6N4O | ☐ | 162.15 | 1.183 | 2.95 | 485 | | | | 164.16 | 485 |

Solvents:

| Name | Ratio | Volume |
|---|---|---|
| Ethyl Acetate | | |

Products:

| Product | MF | Actual Mass (mg) | Actual Mol (mmol) | Yield (%) | Purity | MW (g/mol) | Eq | Theo Mol (mmol) | Theo Mass (mg) | FM (g/mol) |
|---|---|---|---|---|---|---|---|---|---|---|
| 1 | C20H22N4O4S | 1058 | 2.457 | 99 | | 430.52 | 0.997 | 2.490 | 1072 | 430.52 |

Preparation:

To a 10 ml RBF with a clean stir bar added Bumetanide (910 mg, 2.49 mmol) directly from the bottle. Dissolved Bumetanide in EtOAc (15 ml). Stirred under argon. Added 1,1-carbonyldiimidazole (485 mg, 2.95 mmol). The mixture was heated until homogeneous and stirred under argon. Upon cooling the reaction mixture formed a white precipitate. TLC on $SiO_2$ in 100% EtOAc showed a less polar blue-green fluorescent spot.

Filtered the precipitate under vacuum. Washed thoroughly with EtOAc. Dried under argon to obtain a white powder yielding 99% with respect to the starting material. $^1$H and 13C NMR in $CDCl_3$ were consistent with the product.

$^1$H NMR (300 MHz, $CDCl_3$) 0.82 (t, J=7.5 Hz, 3H), 1.14 (m, J=7.5 Hz, 2H), 1.43 (m, J=6.6 Hz, 2H), 3.08 (t J=6 Hz, 2H), 6.97 (d, J=7.2 Hz, 2H), 7.18 (m, 2H), 7.34 (m, J=6.9 Hz, 2H), 7.58 (s, 1H), 7.64 (m, 1H), 8.14 (s, 1H)

13C NMR (75 MHz, $CDCl_3$) 13.94, 20.11, 31.13, 43.25, 50.0, 50.05, 77.63, 115.75, 116.34, 118.46, 130.64, 138.55

7. Preparation of AQP-0007

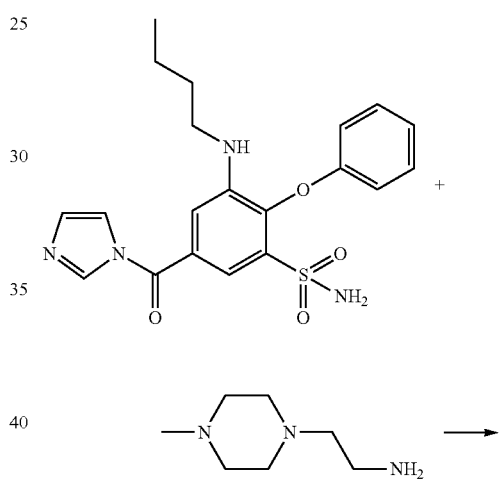

-continued

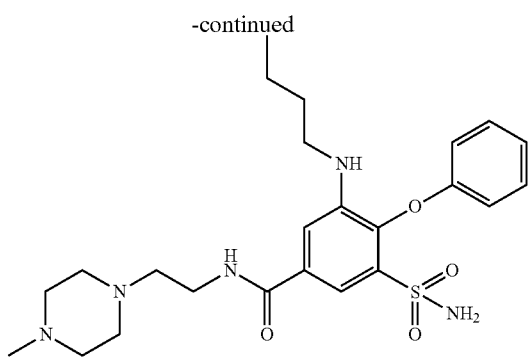

Reaction Conditions:

| | |
|---|---|
| Reaction Molarity | |
| Pressure | Atm |
| Temperature | 25 deg C. |

Reactants:

| Reactant | MF | Limit? | MW (g/mol) | Eq | Moles (mmol) | Sample Mass (g) | Vol | Molarity | d | % Wt | FM | Reactant Mass (g) |
|---|---|---|---|---|---|---|---|---|---|---|---|---|
| 1 | C20H22N4O4S | ☑ | 414.48 | 1.000 | 0.5 | 0.207 | | | | | 414.48 | 0.207 |
| 2 | C7H17N3 | ☐ | 143.23 | 2.000 | 1.000 | 0.143 | | | | | 143.23 | 0.143 |

Solvents:

| Name | Ratio | Volume |
|---|---|---|
| Dichloromethane | | |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C24H35N5O4S | 0.169 | 0.345 | 69.0 | | 489.63 | 1.000 | 0.500 | 0.245 | 489.63 |

Preparation:
To a 10 ml RBF containing a magnetic stir bar was added 2-(4-Methylpiperazine-1-yl)ethanamine (143 mg, 1 mmol) in DCM (1 ml). Let stir under argon at room temperature. 1,1'-Carbonyldiimidazole (207 mg, 0.5 mmol) was added to the above solution using a spatula. Started forming a white precipitate. TLC on SiO$_2$ in 100% MeOH against the imidazolde indicated a very polar product.
Let the solution stir overnight under argon. TLC indicated the completion of the reaction. Extracted the mixture into 25 ml EtOAc. Washed with 2×20 ml of distilled water and 20 ml brine. Combined the desired fractions and dried over anhydrous MgSO$_4$. Filtered and concentrated in vacuo. Dissolved in the minimum amount of EtOAc and reprecipitated from hexanes. Filtered the product as a colorless solid and dried under vacuum to obtain a 69% yield.
$^1$H and 13C NMR in CDCl$_3$ with 2 drops of MeOD. Sample was designated NTF-2006-1-006A
$^1$HNMR (300 MHz, CDCl$_3$) 0.78 (t, =7.5 Hz, 3H), 1.08 (m, J=7.5 Hz, 2H), 1.38 (m, J=7.5 Hz,4H), 1.47 (br s, 4H), 2.27 (s, 3H), 2.47 (br t,4H), 2.54 (br t, 4H), 2.60 (t, J=6 Hz, 3H), 3.08 (m, J=9.0 Hz, 2H), 3.52 (m, J=5.7 Hz, 2H), 6.89 (d, J. 9.0 Hz, 2H), 7.07 (t, J=6.9 Hz, 1H), 7.28 (t, J=8.4 Hz, 2H), 7.45 (br d, J=1.8 Hz, 1H), 7.55 (br d, 1H)
$^{13}$C NMR (75 MHz, CDCl$_3$) 14.00, 20.16, 31.32, 36.84, 43.26, 43.36, 46.23, 53.07, 55.21, 56.99, 112.96, 115.64, 124.05, 130.44, 132.81, 136.18, 142.79, 142.84, 156.20
FABMS 490 (M+H)$^+$; HRMS calcd for C$_{24}$H$_{36}$N$_5$O$_4$S$^+$ 489.2410. found 490.2510.

8. Preparation of AQP-0008

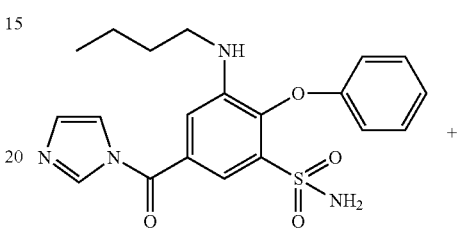
+

-continued

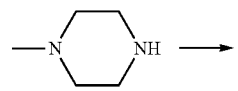
→

-continued

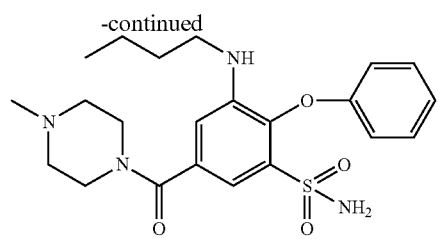

Reaction Condtions:

| | |
|---|---|
| Reaction Molarity | |
| Pressure | Atm |
| Temperature | 25 deg C. |

Reactants:

| Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C20H22N4O4S | ☑ | 414.48 g/mol | 1.000 | 0.5 | 0.207 | | | | | 414.48 | 0.207 |
| 2 | C5H12N2 | ☐ | 100.16 | 2.000 | 1.000 | 0.100 | | | | | 100.16 | 0.100 |

Solvents:

| Name | Ratio | Volume |
|---|---|---|
| Dichloromethane | | 15 |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C22H30N4O4S | 0.057 | 0.128 | 25.5 | | 446.56 | 1.000 | 0.500 | 0.223 | 446.56 |

Preparation:

To a 10 ml RBF containing a magnetic stir bar was added 1-Methylpiperazine (100 mg, 1 mmol) in DCM (1 ml). Stirred under argon at room temperature. Added 1,1'-Carbonyldiimidazole (207 mg, 0.5 mmol) using a spatula. With stirring the solution became homogeneous. TLC on SiO$_2$ in 10% MeOH in EtOAc against imidazolide showed a very polar product spot.

Let the solution stir overnight under argon at room temperature. TLC again against the starting imidazolide indicated completion of reaction. Extracted the reaction mixture into 25 ml of EtOAc. Washed with 2×20 ml distilled water and 20 ml brine. Combined the desired fractions and dried under anhydrous MgSO$_4$. Filtered and concentrated in vacuo. Dissolved in the minimum amount of EtOAc and reprecipated from hexanes. Filtered the colorless product and dried under vacuum to obtain a solid designated NTF-2006-1-007A. $^1$H and 13C NMR in CDCl$_3$ with 2 drops of MeOD. Submitted for high resolution mass spec.

$^1$HNMR (300 MHz, CDCl$_3$) 0.81 (t, J=7.5 Hz, 3H), 1.15 (m, J=7.5 Hz, 2H), 1.40 (m, J=7.5 Hz, 2H), 2.32 (s, 3H), 2.45 (br d, 4H), 3.05 (m, J=6 Hz, 2H), 3.64 (br 6, 4H), 3.93 (t, J=5.4 Hz, 1H), 5.29 (br s, 2H), 6.94 (brm, 3H), 7.09 (t, J=9 Hz, 1H), 7.24 (s, 1H), 7.31 (t, J=9 Hz, 2H)

13C NMR (75 MHz, CDCl$_3$) 13.56, 19.78, 30.82, 42.81, 42.91, 45.82, 112.97, 114.18, 115.24, 123.55, 129.97, 133.53, 135.95, 137.27, 142.49, 142.54, 155.80, 169.05

FABMS 447 (M+H)$^+$; HRMS calcd for $C_{22}H_{31}N_4O_4S+^+$ 447.2066. found 447.2060.

9. Preparation of AQP-0009

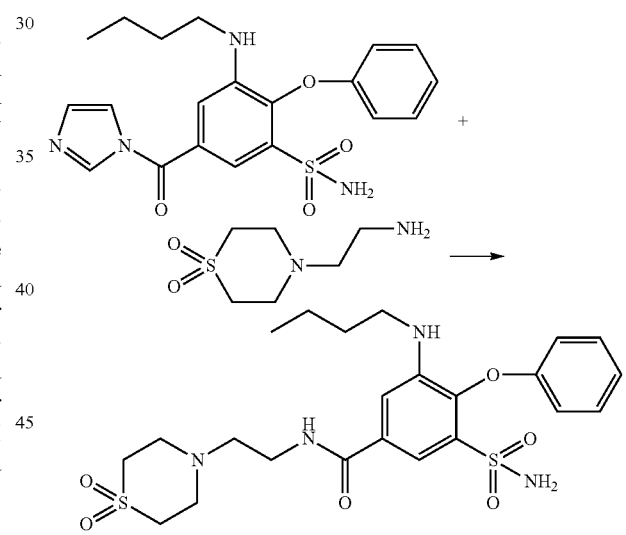

Reaction Conditions:

| | |
|---|---|
| Reaction Molarity | |
| Pressure | Atm |
| Temperature | 25 deg C. |

Reactants:

| Reactant | MF | Limit? | MW (g/mol) | Eq | Moles (mmol) | Sample Mass (g) | Vol | Molarity | d | % Wt | FM | Reactant Mass (g) |
|---|---|---|---|---|---|---|---|---|---|---|---|---|
| 1 | C20H22N4O4S | ☑ | 414.48 | 1.000 | 0.5 | 0.207 | | | | | 414.48 | 0.207 |
| 2 | C6H14N2O2S | ☐ | 178.25 | 2.000 | 1.000 | 0.178 | | | | | 178.25 | 0.178 |

Solvents:

| Name | Ratio | Volume |
|---|---|---|
| Dichloromethane | | |

Products:

| Product | MF | Actual Mass (g) | Actual Mol (mmol) | Yield (%) | Purity | MW (g/mol) | Eq | Theo Mol (mmol) | Theo Mass (g) | FM |
|---|---|---|---|---|---|---|---|---|---|---|
| 1 | C23H32N4O6S2 | 0.178 | 0.339 | 67.9 | | 524.65 | 1.000 | 0.500 | 0.262 | 524.65 |

Preparation:

To a 10 ml RBF containing a stir bar was added 4-(2-Aminoethyl)thiomorpholine 1,1-dioxide (178 mg, 1 mmol) in DCM (1 ml). The solution was stirred under argon at room temperature. To the above solution was added 1,1'-Carbonyldiimidazole(207 mg, 0.5 mmol) using a spatula. Solution became cloudy. TLC on SiO$_2$ in 100% MeOH against imidazolide.

Stirred the reaction overnight at room temperature under argon. TLC again using the same conditions solvent system showed the same spots. Extracted into 25 ml EtOAc. Washed with 2×20 ml distilled water and 20 ml brine. Combined the desired fractions and dried under anhydrous MgSO$_4$. Filtered and concentrated under vacuo. Dissolved in the minimum amount of EtOAc and reprecipitated from hexanes. Filtered the product and dried under vacuum to obtain a colorless solid product. $^1$H and 13C NMR in CDCl$_3$ 2 drops of MeOD. Submitted for high resolution mass spec. Sample was designated as NTF-2006-1-008A $^1$HNMR (300 MHz, CDCl$_3$) 0.80 (t, J=6.3 Hz, 3H). 1.13 (m, J=7.5 Hz, 2H), 1.25 (br d, J=7.2 Hz, 1H), 1.42 (m, J=7.2 Hz, 2H), 2.73 (t, J=6 Hz, 2H), 3.04 (br, 8H), 3.08 (m, 2H), 3.49 (t, J=6 Hz, 2H), 5.60 (br s, 1H), 6.90 (d, J-=9 Hz, 2H), 7.08 (t, J=6 Hz, 1H), 7.29 (t, J=9 Hz, 2H), 7.43 (d, 0.1=1.5 Hz, 1H), 7.53 (d, J=1.8 Hz, 1H)

13C NMR (75 MHz, CDCl$_3$) 8.0, 20.0, 31.0, 37.5, 43.0, 51.0, 52.0, 55.5, 61.0, 112.5, 115.7, 124.0, 130.5, 132.5, 136.0, 139.0, 142.5, 156.0, 167

FABMS 525 (M+H)$^+$; HRMS calcd for $C_{23}H_{33}N_4O_6S_2{}^+$ 525.1842. found 525.1819.

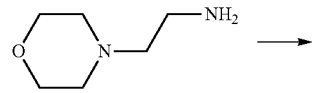

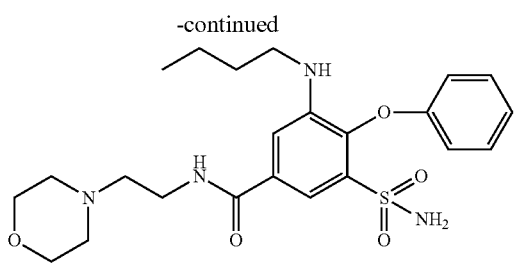

Reaction Conditions:

| Reaction | |
|---|---|
| Molarity | |
| Pressure | Atm |
| Temperature | 25 deg C. |

Reactants:

| Reactant | MF | Limit? | MW (g/mol) | Eq | Moles (mmol) | Sample Mass (g) | Vol | Molarity | d | % Wt | FM | Reactant Mass (g) |
|---|---|---|---|---|---|---|---|---|---|---|---|---|
| 1 | C20H22N4O4S | ☑ | 414.48 | 1.000 | 0.5 | 0.207 | | | | | 414.48 | 0.207 |
| 2 | C6H14N2O | ☐ | 130.19 | 2.000 | 1.000 | 0.130 | | | | | 130.19 | 0.130 |

10. Preparation of AQP-0010

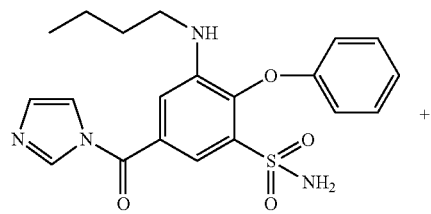

\+

Solvents:

| Name | Ratio | Volume |
|---|---|---|
| Dichloromethane | | |

Products:

| Product | MF | Actual Mass (g) | Actual Mol (mmol) | Yield (%) | Purity | MW (g/mol) | Eq | Theo Mol (mmol) | Theo Mass (g) | FM |
|---|---|---|---|---|---|---|---|---|---|---|
| 1 | C23H32N4O5S | 0.200 | 0.420 | 84 | | 476.59 | 1.000 | 0.500 | 0.238 | 476.59 |

Preparation:

To a 10 ml RBF containing a magnetic stir bar was added N-ethylaminemorpholine (130 mg, 1 mmol) in DCM (1 ml). Stirred the solution under argon at room temperature. To the above solution was added 1,1'-Carbonydiimidazole (207 mg, 0.5 mmol) using a spatula. TLC on SiO$_2$ in 10% MeOH in EtOAc indicated a very polar spot.

Stirred overnight under argon at room temperature. TLC showed completion of the reaction. No trace of starting material was left.

Worked up by extracting the reaction mixture into 25 ml EtOAc. Washed the organic layer with 2×20 ml distilled water and 20 ml brine. Combined the desired fractions and dried under anhydrous MgSO$_4$. Filtered and concentrated in vacuo. Dissolved again in the minimum amount of EtOAc and reprecipitated from hexanes. Filtered the precipitate to obtain a white solid designated as NTF-2006-1-009A. $^1$H and $^{13}$CNMR in CDCl$_3$ with 2 drops of MeOD. Submitted for high resolution mass spec.

$^1$HNMR (300 MHz, CDCl$_3$) 0.82 (t, J=6 Hz, 3H), 1.11 (m, J=6 Hz, 2H), 1.37 (m, J=6 Hz, 2H), 2.50 (dd, 4H), 2.60 (t, J=3 Hz, 2H), 3.10 (br dd, 2H), 3.55 (br dd, 2H), 3.70 (br dd, 4H), 3.89 (br t, 1H), 5.40 (br s, 1H), 6.87 (d, 0.1=6 Hz, 2H), 7.05 (br t, 1H), 7.26 (br t, 1H), 7.39 (br d, 1H), 7.50 (br d, 1H)

13CNMR (75 MHz, CDCl$_3$) 13.54, 19.69, 30.86, 36.33, 42.88, 53.28, 56.98, 66.71, 112.44, 115.08, 115.19, 123.56, 129.95, 132.29, 135.68, 138.53, 142.34, 155.72, 166.33

FABMS 477 (M+H)$^+$; HRMS calcd for C$_{23}$H$_{33}$N$_4$O$_5$S$^+$ 477.2172. found 477.2175.

-continued

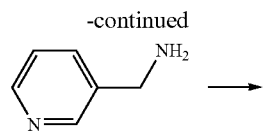

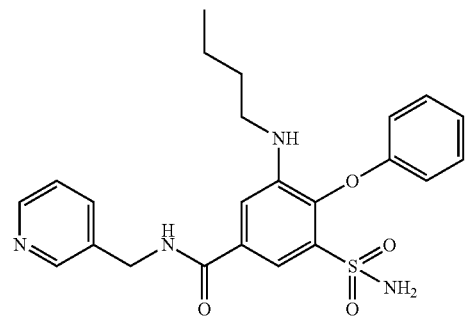

Reaction Conditions:

| Reaction Molarity | |
| Pressure | Atm |
| Temperature | 25 deg C. |

Reactants:

| Reactant | MF | Limit? | MW (g/mol) | Eq | Moles (mmol) | Sample Mass (g) | Vol | Molarity | d | % Wt | FM | Reactant Mass (g) |
|---|---|---|---|---|---|---|---|---|---|---|---|---|
| 1 | C20H22N4O4S | ☐ | 414.48 | 1.000 | 0.5 | 0.207 | | | | | 414.48 | 0.207 |
| 2 | C6H8N2 | ☑ | 108.14 | 2.000 | 1.000 | 0.108 | | | | | 108.14 | 0.108 |

Preparation of AQP-0011

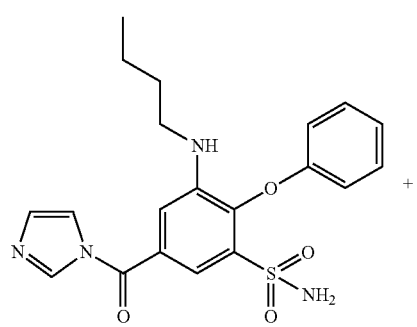

Solvents:

| Name | Ratio | Volume |
|---|---|---|
| Dichloromethane | | |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C23H26N4O4S | 0.181 | 0.398 | 80 | | 454.54 | 1.000 | 0.500 | 0.227 | 454.54 |

Preparation:

To a 10 ml RBF containing a magnetic stir bar was added 3-aminomethylpyridine (108 mg, 1 mmol) in DCM (1 ml). Stirred under argon at room temperature. To the above solution was added 1,1'-Carbonyldiimidazole (207 mg, 0.5 mmol). TLC was performed on the resulting solution against imidazolide in 10% MeOH in EtOAc.

Stirred overnight under argon. Maintained the reaction at room temperature. TLC again after 12 h indicated completion of reaction.

Extracted into 25 ml EtOAc. Washed the organic layer with 2×20 ml distilled water and 20 ml brine. Combined the desired fractions and dried under anhydrous MgSO$_4$. Filtered and concentrated in vacuo. Dissolved the resulting crude oil in the minimum amount of EtOAc and reprecipitated from hexanes. Filtered the resulting precipitate and dried under vacuum to obtain a white solid designated as NTF-2006-1-010A. $^1$H and 13C NMR in CDCl$_3$ with 2 drops of MeOD. Submitted for high resolution mass spec.

$^1$HNMR (300 MHz, CDCl$_3$) 0.74 (t, J=7.5 Hz, 3H), 1.07 (m, J=7.5 Hz, 2H), 1.34 (m, J=7.5 Hz, 2H), 2.59 (s, 4H), 3.03 (t, J=6.6 Hz, 2H), 4.56 (d, J=5.7 Hz), 6.85 (dt, J$_1$=7.5 Hz, J$_2$=2.1 Hz, 2H), 7.02 (tt, J$_1$=5.7 Hz, J$_2$=1.2 Hz, 1H), 7.26 (m, 1H), 7.43 (d, J=2.1 Hz, 1H), 7.53 (d, J=2.1 Hz, 1H), 7.20 (dt, J$_1$7.8 Hz, J$_2$=1.8 Hz, 1H), 8.01 (t, J=4.5 Hz, 1H), 8.40 (dd, J$_1$=4.8 Hz, J$_2$=1.5 Hz, 1H), 8.50 (br d, J=4.2 Hz, 1H)

13C NMR (75 MHz, CDCl$_3$) 13.93, 20.09, 31.25, 41.69, 43.19, 113.03, 115.59, 115.76, 123.93, 124.15, 130.34, 132.11, 134.97, 136.12, 142.79, 148.42, 149.17, 156.19

FABMS 455 (M+H)$^+$; HRMS calcd for C$_{23}$H$_{27}$N$_4$O$_4$S$^+$ 455.1753. found 455.1750.

Preparation of AQP-0012

Reaction Condtions:

| | |
|---|---|
| Reaction Molarity | |
| Pressure | Atm |
| Temperature | 25 deg C. |

Reactants:

| Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C20H22N4O4S | ☑ | 414.48 | 1.000 | 0.499 | 0.207 | | | | | 414.48 | 0.207 |
| 2 | C5H6N2 | ☐ | 94.11 | 2.000 | 0.999 | 0.094 | | | | | 94.11 | 0.094 |

Solvents:

| Name | Ratio | Volume |
|---|---|---|
| Dichloromethane | | |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C22H24N4O4S | 0.131 | 0.297 | 59.5 | | 440.52 | 1.000 | 0.499 | 0.220 | 440.52 |

Preparation:

To a 25 ml RBF containing a magnetic stir bar was added 2-aminopyridine (0.094 g, 0.999 mmol) and dissolved in 1 ml DCM. Stirred the above solution under argon at rt. To the above solution was added imidazolide of bumetanide (0.207 g, 0.499 mmol) and let stir.

Extracted the reaction mixture into EtOAc, washed with 2×20 ml distilled water and 2×20 ml brine. Dried under MgSO$_4$. Filtered and rotavapped. Took into the minimum amount of EtOAc and reprecipitated from hexanes to obtain a yellowish powder.

'H NMR in (CDCl$_3$, 300 MHz) 1.80 ppm (t, J=10 Hz, 3H), 1.13 ppm (m, 2H), 1.37 ppm (m, 2H) 1.90 ppm (s, br, 1H), 3.04 ppm (t, J=7 Hz, 2H), 6.92 ppm (d, J=7.8 Hz, 1H), 7.09 ppm (d, J=7.8 Hz, 1H), 7.13 ppm (dd, 1H), 7.23 ppm (dd, 1H), 7.57 (d, J=13.5 ppm, 1H), 8.11 ppm (s, 1H)

13CNMR (75 MHz, DMSO-d$_6$) 9.25, 15.39, 26.51, 38.53, 38.63, 44.77, 45.06, 45.34, 45.62, 45.91, 110.93, 111.99, 112.18, 117.13, 119.40, 123.59, 125.72, 130.56, 131.76, 135.46, 137.79, 151.32, 161.73

FABMS 441(M+H)$^+$; HRMS calcd for C$_{22}$H$_{25}$N$_4$O$_4$S$^+$ 441.16. found 441.1600.

Preparation of AQP-0013

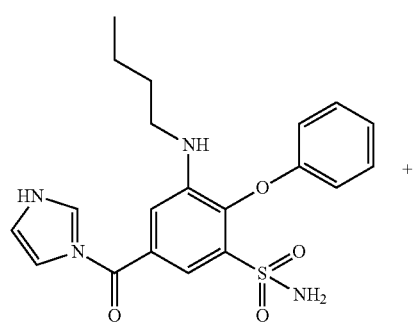

+

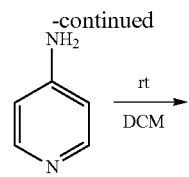

-continued

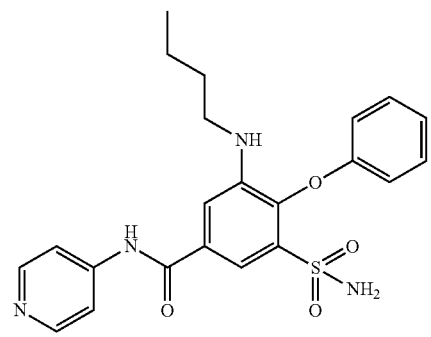

Reaction Conditions:

| | |
|---|---|
| Reaction Molarity | |
| Pressure | Atm |
| Temperature | 25 deg C. |

Reactants:

| | Reactant MF | Limit? | MW | Eq | Sample Moles (mmol) | Sample Mass (g) | Vol | Molarity | d | % Wt | FM | Reactant Mass (g) |
|---|---|---|---|---|---|---|---|---|---|---|---|---|
| 1 | C20H23N4O4S | ☑ | 415.49 | 1.000 | 0.498 | 0.207 | | | | | 415.49 | 0.207 |
| 2 | C5H6N2 | ☐ | 94.11 | 2.000 | 0.996 | 0.094 | | | | | 94.11 | 0.094 |

Solvents:

| Name | Ratio | Volume |
|---|---|---|
| Dichloromethane | | 5 |

Products:

| | Product MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C22H24N4O4S | 0.122 | 0.277 | 55.6 | | 440.52 | 1.000 | 0.498 | 0.219 | 440.52 |

Preparation:

To a 25 ml RBF containing a magnetic stir bar was added 4-aminopyridine (0.094 g, 0.996 mmol) and dissolved in 1 ml DCM. Let stir under argon, at r.t. To the above solution was added the imidazolide of Bumetanide (0.207 g, 0.498 mmol). Formed a white precipitate. Stirred the above solution under argon at r.t.

Extracted into EtOAc. Washed with water (2×20 ml) and brine (2×20 ml). Combined the organic layers, dried under MgSO$_4$ and filtered. Concentrated under vacuum to obtain a yellowish white solid. NMR in MeOD.

$^1$HNMR (300 MHZ, MeOD) 0.75 ppm (t, J=5.4 Hz, 3H), 1.10 ppm (m, 2H), 1.30 ppm (m, 2H), 2.85 ppm (t, br, 2H), 6.76 ppm (dd, 2H), 7.02 ppm (t, br, J=6.9 Hz, 1H), 8.00 ppm (d, J=6.6 Hz, 1H)

13CNMR (75 MHz, DMSO-d$_6$) 15.52, 22.26, 33.62, 45.27, 56.23, 111.56, 117.75, 131.89, 139.31, 142.72, 144.04, 159.54, 163.02

Preparation of AQP-0014

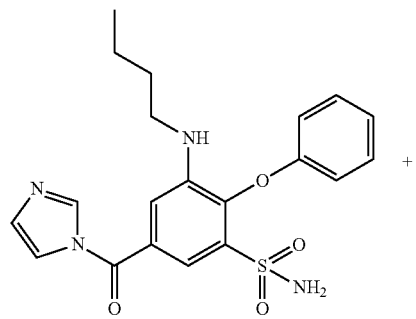

+

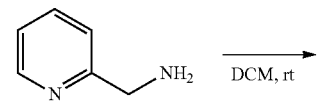

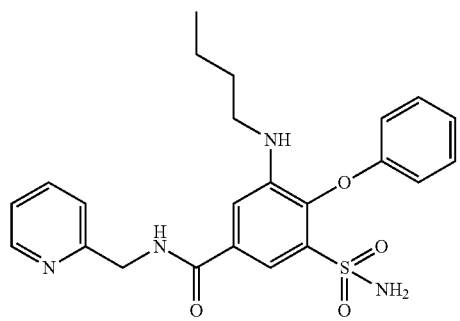

Reaction Conditions:

| | |
|---|---|
| Reaction Molarity | |
| Pressure | Atm |
| Temperature | 25 deg C. |

Reactants:

| | Reactant MF | Limit? | MW | Eq | Moles (mmol) | Sample Mass (g) | Vol (ml) | Molarity | d (g/ml) | % Wt | FM | Reactant Mass (g) |
|---|---|---|---|---|---|---|---|---|---|---|---|---|
| 1 | C20H22N4O4S | ☑ | 414.48 | 1.000 | 0.499 | 0.207 | | | | | 414.48 | 0.207 |
| 2 | C6H8N2 | ☐ | 108.14 | 2.000 | 0.999 | 0.108 | 0.103 | | 1.049 | | 108.14 | 0.108 |

Solvents:

| Name | Ratio | Volume |
|---|---|---|
| Dichloromethane | | 5 |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C23H26N4O4S | 0.179 | 0.394 | 79 | | 454.54 | 1.000 | 0.499 | 0.227 | 454.54 |

Preparation:
To a 25 ml RBF containing a magnetic stir bar was added the imidazolide (0.207 g, 0.499 mmol) and dissolved in 1 ml DCM. Stirred under argon. Added the amine (0.108 g, 0.999 mmol) and stirred overnight. TLC in 100% EtOAc. A more polar spot showed up. Extracted into EtOAc washing with water (2×20 ml) and brine (2×20 ml). Concentrated under vacuum. Dissolved in the minimum amount of EtOAc and reprecipitated from hexanes to obtain white solid.

$^1$HNMR (CDCl$_3$, 300 MHz) 0.82 ppm (t, J=10 Hz, 3H), 1.12 ppm (m, 2H), 1.39 ppm (m, 2H), 4.59 ppm (s,br, 2H), 6.86 ppm(d, J8 Hz, 2H), 7.01 ppm (t, J=7.8 Hz, 1H), 7.26 ppm (m, 2H), 7.33 ppm (d, J=7.8 Hz, 1H), 7.48 ppm (s, 1H), 7.70 ppm (s, 1H), 7.76 ppm (t, 7.8 Hz, 1H), 8.51 ppm (t, J=1.8 Hz, 1H)

13CNMR (75 MHz, DMSO-d$_6$) 14.38, 14.82, 20.16, 21.46, 31.14, 42.79, 45.51, 60.58, 114.06, 114.27, 116.39, 121.81, 122.94, 123.02, 129.91, 132.25, 137.56, 138.18, 139.19, 143.01, 149.67, 157.28, 159.55, 159.56, 166.24

FABMS 455(M+H)$^+$; HRMS calcd for C23H27N4)4S$^+$ 455.18. found 455.17.

Preparation of AQP-0015

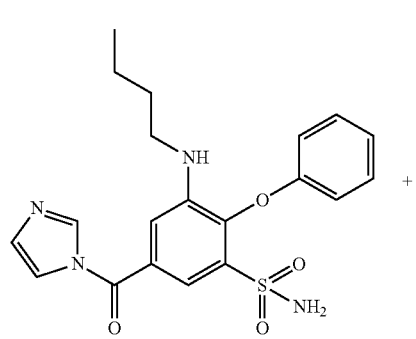

+

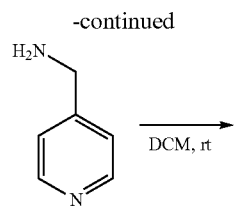

DCM, rt

-continued

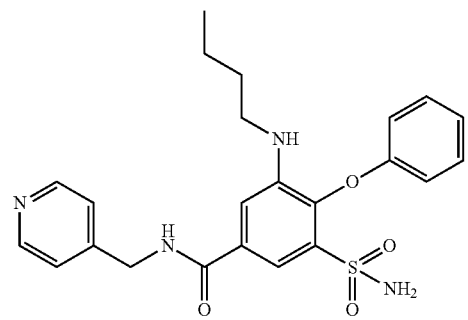

Reaction Conditions:

| Reaction Molarity | |
|---|---|
| Pressure | Atm |
| Temperature | 25 deg C. |

Reactants:

| | Reactant MF | Limit? | MW (g/mol) | Eq | Moles (mmol) | Sample Mass (g) | Vol (ml) | Molarity | d (g/ml) | % Wt | FM | Reactant Mass (g) |
|---|---|---|---|---|---|---|---|---|---|---|---|---|
| 1 | C20H22N4O4S | ☑ | 414.48 | 1.000 | 0.499 | 0.207 | | | | | 414.48 | 0.207 |
| 2 | C6H8N2 | ☐ | 108.14 | 2.000 | 0.999 | 0.108 | 0.100 | | 1.08 | | 108.14 | 0.108 |

Solvents:

| Name | Ratio | Volume |
|---|---|---|
| Dichloromethane | | 5 |

Products:

| | Product MF | Actual Mass (g) | Actual Mol (mmol) | Yield (%) | Purity | MW (g/mol) | Eq | Theo Mol (mmol) | Theo Mass (g) | FM |
|---|---|---|---|---|---|---|---|---|---|---|
| 1 | CH23H26N4O4S | 0.208 | 0.458 | 92 | | 454.54 | 1.000 | 0.499 | 0.227 | 454.54 |

Preparation:
To a RBF containing a magnetic stir bar was added the imidazolide (0.207 g, 0.499 mmol) and dissolved in 1 ml DCM. Stirred under argon. To the above solution was added the amine (0.108 g, 0.999 mmol) and stirred at r.t. (room temperature) overnight. TLC in 100% EtOAc. The reaction was complete in a couple of hours as indicated by a more polar product in TLC. Extracted into EtOAc (25 ml), washed with water (2×20 ml) and brine (2×20 ml). Combined the organic layers and dried under $MgSO_4$. Filtered and concentrated. Dissolved in the minimum amount DCM and reprecipitated from hexanes to obtain a colorless solid.

$^1$HNMR ($CDCl_3$, 300 MHz) 0.82 ppm (t, J=10 Hz, 3H), 1.15 ppm (m, 2H), 1.35 ppm (m,2H), 4.51 ppm (s,2H), 6.86 ppm(d, J=7.8 Hz, 2H), 7.01 ppm (d, J=12.9 Hz, 1H), 7.24 ppm (d, J=6.9 Hz, 1H), 7.29 ppm (t, J=6.9 HzHz, 1H), 7.30 ppm (d, J=2.4 Hz, 2H), 7.45 ppm (s, 1H), 7.68 ppm (t, J=2.1 Hz, 1H), 8.51 (dd, 2H)

13CNMR (75 MHz, DMSO-$d_6$) 19.16, 19.59, 24.91, 26.25, 35.86, 47.34, 47.54, 65.33, 118.80, 118.93, 121.16, 127.72, 127.78, 134.67, 136.79, 142.96, 144.03, 147.79, 154.18, 155.12, 162.02, 171.10

FABMS 455(M+H)$^+$; HRMS calcd for $C_{23}H_{27}N_4O_4S^+$ 455.18. found 455.17.

Preparation of AQP-0016

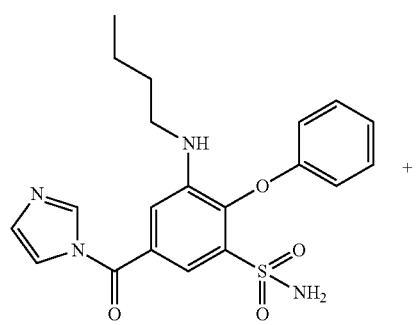

+

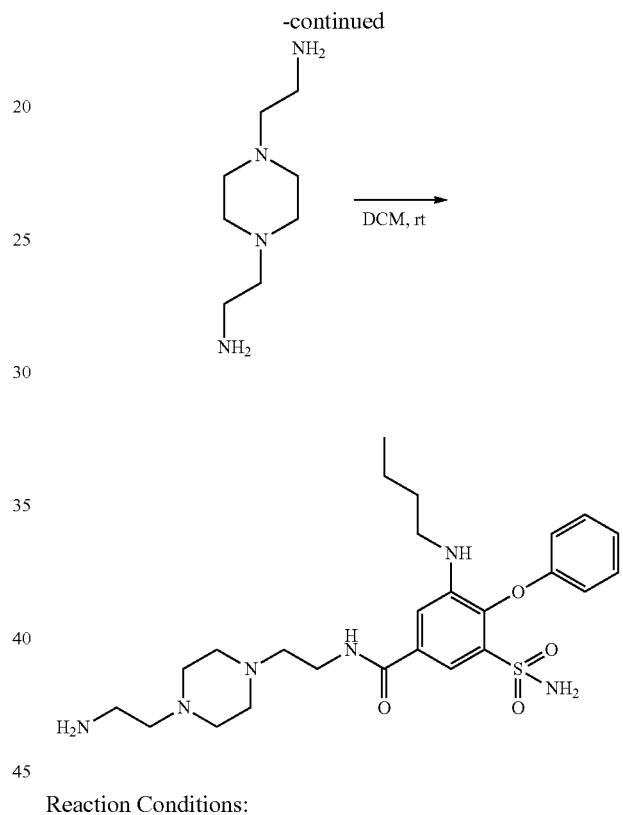

Reaction Conditions:

| Reaction Molarity | |
|---|---|
| Pressure | Atm |
| Temperature | 25 deg C. |

Reactants:

| | Reactant MF | Limit? | MW | Eq | Sample Moles (mmol) | Sample Mass (g) | Vol | Molarity | d | % Wt | FM | Reactant Mass (g) |
|---|---|---|---|---|---|---|---|---|---|---|---|---|
| 1 | C20H22N4O4S | ☑ | 414.48 | 1.000 | 0.499 | 0.207 | | | | | 414.48 | 0.207 |
| 2 | C8H20N4 | ☐ | 172.27 | 2.000 | 0.999 | 0.172 | | | | | 172.27 | 0.172 |

Solvents:

| Name | Ratio | Volume |
|---|---|---|
| Dichloromethane | | 5 |

Products:

| | Product MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C25H38N6O4S | 0.053 | 0.102 | 20.46 | | 518.67 | 1.000 | 0.499 | 0.259 | 518.67 |

Preparation:

To a 25 ml RBF containing a magnetic stir bar was added the imidazolide of Bumetanide (0.207 g, 0.99 mmol) and dissolved in 1 ml DCM. To the above solution was added the amine (0.172 g, 0.999 mmol) and let stir overnight at rt under argon. TLC in 10% MeOH in EtOAc indicated a very polar spot. Extracted the reaction mixture into EtOAc, washed with water (2×20 ml) and then with brine (2×20 ml). The organic layer was dried under MgSO$_4$ and filtered. Concentrated the organic layer under vacuum. Redissolved the crude product in the minimum amount of DCM and reprecipitated from hexanes. Filtered the above precipitate to obtain yellowish white solid. 'HNMR in DMSO-d$_6$+2 drops of MeOD.

'HNMR (300 MHz, DMSO-d$_6$+2 drops of MeOD).0.80 ppm (t, J=10 Hz, 3H), 1.11 ppm (m, 2H), 1.37 ppm (m,2H), 2.50 ppm (m, 8H), 3.05 ppm (t, J=6.6 Hz, 2H), 3.35 ppm (t, J=6.6 Hz, 2H), 4.1 ppm (s, br, 4H), 4.95 ppm (t, br, 1H), 6.85 ppm (d, J=7.8 Hz, 2H), 7.00 ppm (t, 7.2 Hz, 1H), 7.26 ppm (dd, J=7.8 Hz, 2H), 7.6 ppm (s, 1H)

13CNMR (75 MHz, DMSO-d$_6$) 19.23, 24.93, 35.89, 47.50, 58.45, 62.50, 107.50, 119.0, 121.16, 128.0, 134.66, 137.50, 144.0, 143.00, 147.80, 162.20, 171.0

FABMS 519 (M+H)$^+$ calcd m/z for C25H39N6O4S$^+$ 519.28. found 519.27.

Preparation of AQP-0017

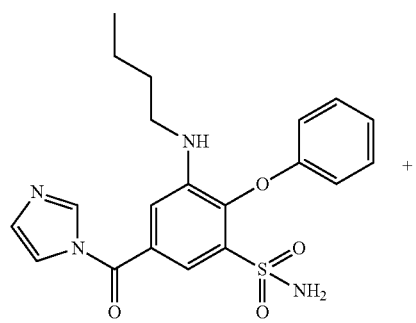

+

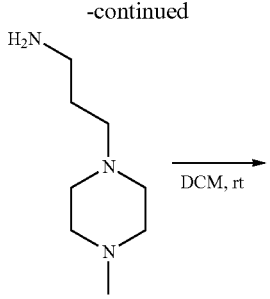

-continued

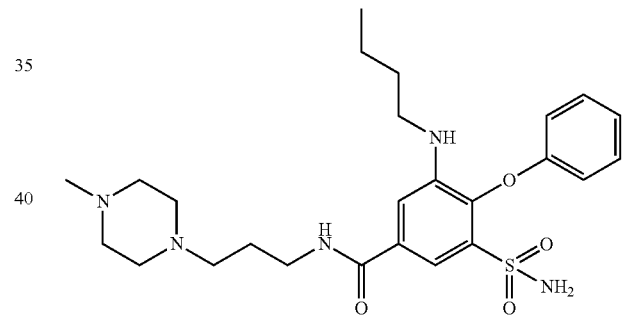

Reaction Conditions:

| | |
|---|---|
| Reaction | |
| Molarity | |
| Pressure | Atm |
| Temperature | 25 deg C. |

Reactants:

| | Reactant MF | Limit? | MW | Eq | Sample Moles (mmol) | Sample Mass (g) | Vol (ml) | Molarity | d (g/ml) | % Wt | FM | Reactant Mass (g) |
|---|---|---|---|---|---|---|---|---|---|---|---|---|
| 1 | C20H22N4O4S | ☑ | 414.48 | 1.000 | 0.499 | 0.207 | | | | | 414.48 | 0.207 |
| 2 | C8H19N3 | ☐ | 157.26 | 2.000 | 0.999 | 0.157 | 0.170 | | 0.924 | | 157.26 | 0.157 |

Solvenst:

| Name | Ratio | Volume |
|---|---|---|
| Dichloromethane | | 5 |

Products:

| | Product MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C25H37N5O4S | 0.181 | 0.359 | 72.0 | | 503.66 | 1.000 | 0.499 | 0.252 | 503.66 |

Preparation:

To a 25 ml RBF containing a magnetic stir bar was added the imidazolide (0.207 g, 0.5 mmol) and dissolved in 1 ml DCM. Let stir under argon. Added the amine (0.170 ml, 1 mmol) and stirred the above solution at rt under argon. The solution became homogeneous. After ~1 h a precipitate started to form. After about three hours TLC showed a more polar spot and the starting material was gone. Extracted into EtOAc (20 ml) and washed with Water (2×20 mL) and brine (2×20 ml). combined the organic layers and dried under MgSO$_4$. Filtered and concentrated. Dissolved in the minimum amount of DCM and reprecipitated from hexanes.

$^1$HNMR (300 MHz, DMSO-d$_6$+2 drops of MeOD) 0.90 ppm (t, J=10 Hz, 3H), 1.10 ppm (m, 2-1), 1.35 ppm (m, 2H), 2.13 ppm (s, 3H), 2.32 ppm (t, J=6.3 Hz, 9H), 3.07 ppm (t, J=6 Hz, 2H), 3.28 ppm (t, 3=5.4 Hz, 2H), 3.35 ppm (s,1H), 4.89 ppm (t, br, 1H), 6.84 ppm (d, J=5.1 Hz, 2H), 7.00 ppm (t, J=10.5 Hz, 1H), 7.23 ppm (dd, J=10.5 Hz, 2H), 7.35 ppm (s, 1H), 7.58 ppm (t, J=2.4 Hz)

13CNMR (75 MHz, DMSO-d$_6$) 19.20, 24.92, 31.93, 35.90, 43.41, 47.56, 51.27, 58.29, 60.33, 61.26, 118.73, 121.14, 127.75, 134.66, 137.60, 142.82, 143.67, 147.64, 162.06, 170.78

FABMS 504 (M+H)$^+$ calcd m/z for C25H38N5O4S$^+$ 504.26. found 504.26.

Preparation of AQP-0019

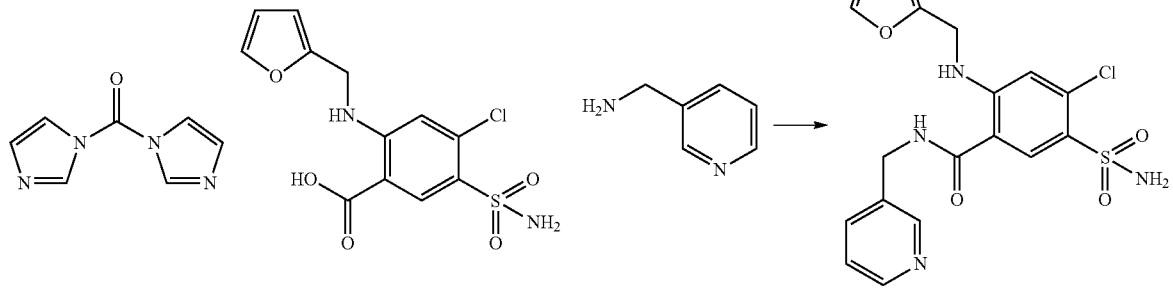

Reaction Conditions:

| | Reaction Molarity Pressure Temperature |
|---|---|

Reactants:

| | Reactant MF | Limit? | MW | Eq | Sample Moles (mmol) | Sample Mass (g) | Vol | Molarity | d | % Wt | FM (g/mol) | Reactant Mass (g) |
|---|---|---|---|---|---|---|---|---|---|---|---|---|
| 1 CDI | C7H6N4O | No | 162.149 | 1.200 | 0.600 | 0.097 | | | | | 162 | 0.097 |
| 2 | C12H11ClN2O5S | Yes | 330.744 | 1.000 | 0.5 | 0.165 | | | | | 331 | 0.165 |
| 3 | C6H8N2 | No | 108.141 | 2.000 | 1.000 | 0.108 | | | | | 108 | 0.108 |

Solvents:

| | Name | Solvent Ratio | Volume (ml) |
|---|---|---|---|
| 1 | EtOAc | | 6.0 |

Products:

| Product | MF | Actual Mass (g) | Actual Mol (mmol) | Yield (%) | Purity | MW | Eq | Theo Mol (mmol) | Theo Mass (g) | FM (g/mol) |
|---|---|---|---|---|---|---|---|---|---|---|
| 1 | C18H17ClN4O4S | 0.150 | 0.356 | 71.3 | | 420.870 | 1.000 | 0.500 | 0.210 | 421 |

Preparation:

To a 10 ml RBF containing a magnetic stirring bar was added furosemide (165 mg, 0.50 mmol) and 3.0 ml EtOAc. The mixture was stirred under argon at 25 deg. C. and 97 mg (0.60 mmol) carbonyldiimidazole (CDI) was added. The mixture was heated with a hot air gun until homogeneous and then allowed to cool. After standing and cooling for 10 minutes, a solution of 108 mg (1.0 mmol) amine in 3 ml EtOAc was added and the mixture was stirred overnight. After this period, a very slightly gummy solid had formed. 10 ml of water was added and the mixture was stirred which resulted in a white fine solid. Filtration followed by washing of the solid with 5 ml water and 5 ml EtOAc and vacuum drying gave 150 mg of a white solid, (ca. 71% yield). TLC indicated that the sample was sufficiently pure and the NMR was Proton NMR=NMR-GAF-60-a, Carbon NMR=NMR-GAF-60-b The compound was registered as AQP-0019.

'HNMR (300 MHz, DMSO-$d_6$) 4.41 ppm (d, J=5 Hz, 2H), 4.51 ppm (d, J=5 Hz, 2H), 6.31 ppm (s, 1H), 6.41 ppm (s, 3H), 7.00 ppm (s,1H), 7.23 ppm (bs, 2H), 7.36 ppm (dd, J=5 Hz, 1H), 7.61 ppm (s,1H), 7.70 ppm (d, J=6 Hz, 11H), 8.20 ppm (s, 1H), (s,1H), 8.48 ppm (d, J=3 Hz, 1H), 8.54 ppm (s,1H), 8.72 ppm (t, J=7 Hz, 18), 9.36 ppm (t, J=7 Hz, 1H)

Preparation of AQP-0020

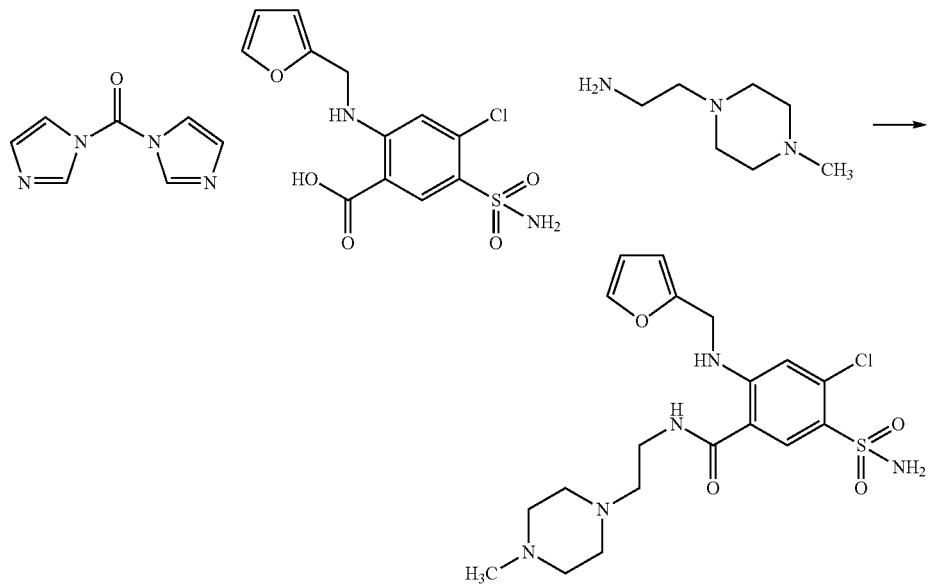

Reaction Conditions:

| | |
|---|---|
| | Reaction |
| | Molarity |
| | Pressure |
| | Temperature |

Reactants:

| Reactant | MF | Limit? | MW | Eq | Moles (mmol) | Sample Mass (g) | Vol | Molarity | d | % Wt | FM (g/mol) | Reactant Mass (g) |
|---|---|---|---|---|---|---|---|---|---|---|---|---|
| 1 CDI | C7H6N4O | No | 162.149 | 1.200 | 0.600 | 0.097 | | | | | 162 | 0.097 |
| 2 | C12H11ClN2O5S | Yes | 330.744 | 1.000 | 0.5 | 0.165 | | | | | 331 | 0.165 |
| 3 | C7H17N3 | No | 143.230 | 2.000 | 1.000 | 0.143 | | | | | 143 | 0.143 |

Solvents:

| | Name | Solvent Ratio | Volume (ml) |
|---|---|---|---|
| 1 | EtOAc | | 6.0 |

Products:

| Product | MF | Actual Mass | Actual Mol | Yield | Purity | MW | Eq | Theo Mol (mmol) | Theo Mass (g) | FM (g/mol) |
|---|---|---|---|---|---|---|---|---|---|---|
| 1 | C19H26ClN5O4S | | | | | 455.959 | 1.000 | 0.500 | 0.228 | 456 |

Preparation:

To a 10 ml RBF containing a magnetic stirring bar was added Furosemide (165 mg, 0.50 mmol) and 3.0 ml EtOAc. The mixture was stirred under argon at 25 deg. C. and 97 mg (0.60 mmol) carbonyldiimidazole (CDI) was added. The mixture was heated with a hot air gun until homogeneous and then allowed to cool. Upon cooling, and standing for 10 minutes, a solution of 143 mg (1.0 mmol) amine in 3 ml EtOAc was added. The mixture was stirred overnight. The reaction was treated with 10 ml water with stirring for 5 min. The organic layer was removed by pipet and the aqueous layer was extracted similarly with 3×5 ml EtOAc. the combined organic extracts were concentrated. The resulting solid was triturated with DCM and then diluted with 50% DCM hexanes and filtered to give: 220 mg of an off white solid.

Proton NMR=NMR-GAF-59-a $^1$HNMR (300 MHz, DMSO-d$_6$) 2.19 ppm (s, 3H), 2.44 ppm (bm, 10H), 3.36 ppm (m, 1H), 5.54 ppm (d, J=5.1 Hz, 2H), 6.37 ppm (s,1H), 6.46 ppm (s, 1H), 7.00 ppm (s, 1H1), 7.08 ppm (s,1H), 7.28 ppm (d, J=6 Hz, 1H), 7.66 ppm (s, 1H), 7.70 ppm (s,1H), 8.10 ppm (s, 1H), 8.60 ppm (s,1H), 8.72 ppm (m, 2H)

This compound was registered as AQP-0020.

Preparation of AQP-0022 and AQP-0023

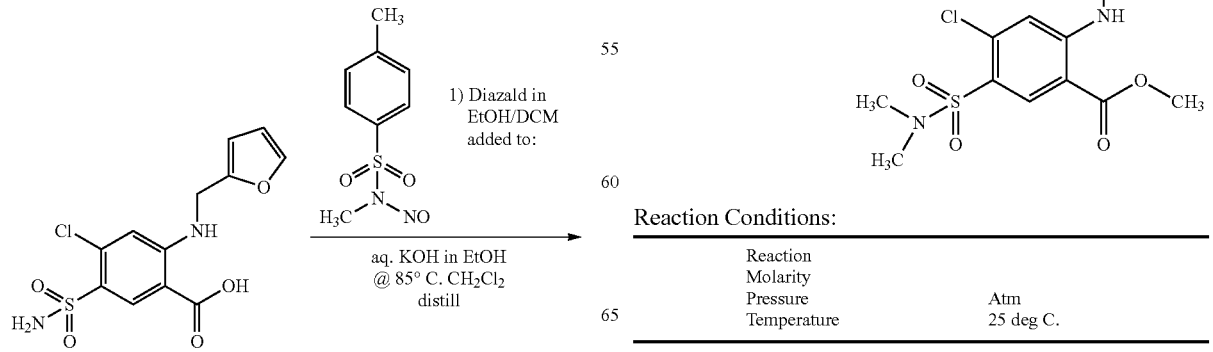

-continued

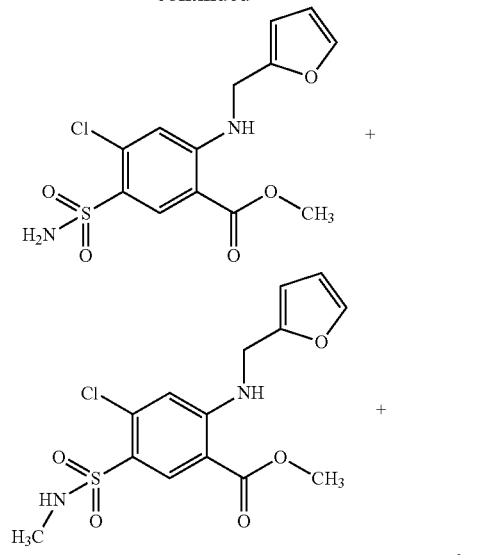

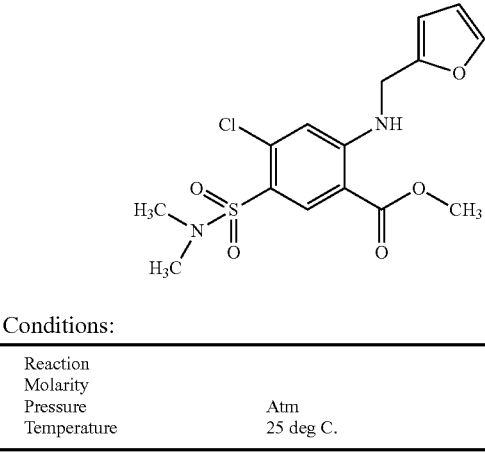

Reaction Conditions:

| Reaction Molarity | |
|---|---|
| Pressure | Atm |
| Temperature | 25 deg C. |

Reactants:

| Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C12H11ClN2O5S | ☑ | 330.74 | 1.000 | 1 | 0.331 | | | | | 330.74 | 0.331 |
| 2 | C8H10N2O3S | ☐ | 214.24 | 10.000 | 10.00 | 2.142 | | | | | 214.24 | 2.142 |

Solvents:

| Name | Ratio | Volume |
|---|---|---|
| Dichloromethane | | |

Products:

| Product | MF | Actual Mass | Actual Mol | Yield (%) | Purity | MW | Eq | Theo Mol (mmol) | Theo Mass (g) | FM |
|---|---|---|---|---|---|---|---|---|---|---|
| 1 | C13H13ClN2O5S | 0.308 g | 0.893 mmol | 89 | | 344.77 | 1.000 | 1.000 | 0.345 | 344.77 |
| 2 | C14H15ClN2O5S | 0.229 g | 0.638 mmol | 63.8 | | 358.80 | 1.000 | 1.000 | 0.359 | 358.80 |
| 3 | C15H17ClN2O5S | no product | 0.00 µmol | 0.00 | | 372.82 | 1.000 | 1.000 | 0.373 | 372.82 |

Preparation:

To a solution of 8 mg KOH in 6 ml of distilled water and 6 ml EtOH in a 100 ml RBF equipped with teflon joint distillation head, chilled condenser with receiving flask in an ice-water bath, and addition funnel was added 10 ml of DCM and the two-phase system was heated to 85° C. Once distillation had initiated, a solution of 2.14 g (10 mmol) Diazald in 10 ml DCM and 5 ml EtOH was added over 15 min. Once the distillation solution was not yellow anymore, the resulting yellow distillate was stoppered and stored in an ice-bath till used.

Two 50 ml Erlenmeyer flasks were prepared with 331 mg (1 mmol) of Furosemide for two experiments. One flask was treated with $CH_2N_2$ solution until a very faint yellow color persisted, gas evolution was observed. The second flask was treated with the remaining $CH_2N_2$ solution, gas evolution was observed, stoppered loosely and allowed to stand overnight.

After 24 hours the first solution was colorless with a precipitate. Added a little bit of hexanes to the solution, started forming crystals, set aside till crystallization is complete. The second solution was also colorless. TLC indicated a less polar product than the first solution.

Did the same thing to the second solution and let recrystalize. From the first solution a colorless, shiny crystalline solid was obtained. From the second solution an off white crystalline solid was collected. $^1$HNMR, 13CNMR and MS were obtained for the two products.

Furosemide methyl ester=NTF-2006-1-018A

Furosemide methyl ester monomethyl sulfonamide=NTF-2006-1-018B.

NTF-AQP-018A HNMR (CDCl$_3$, 300 MHz) ppm 3.10 (BrS, 2H), 3.87 (s, 3H), 4.48 (d, J=6 Hz, 2H), 6.30 (q, J=0.9 D) 6.65 (brs, 2H), 6.89 (s, 1H), 7.41 (dd, J=3 Hz, 1H), 7.62 (s, 1H), 8.54 (s, 2H)

C13 NMR (CDCl$_3$, 75 MHz) 44.65, 44.92, 45.20, 45.47, 45.76, 57.24, 112.92, 113.06, 115.69, 118.63, 138.79, 147.62, 155.69.

MS API-ES calculated m/z for $C_{13}H_{14}ClN_2O_5S^+$ 345.03; obtained 345.1

$^1$HNMR NTF-AQP-018B (CDCl$_3$, 300 MHz) ppm 2.65 (d, J=6 Hz, 3H), 3.90 (s, 3H), 4.46 (d, J=6 Hz, 2H), 4.75 (q, J=6 Hz, 1H), 6.30 (q, J=0.6 Hz, 1H), 6.37 (q, J=0.6 Hz, 1H), 6.89 (s, 1H), 7.42 (q, J=1.2 Hz, 1H), 8.62 (s, 1H), 8.67 (t, 1H)

C13 NMR (CDCl$_3$) 29.707, 40.64, 52.47, 52.53, 108.22, 108.95, 110.91, 113.89, 118.58, 121.55, 136.72, 137.61, 143.03, 150.57, 153.53, 167.99

MS API-ES calculated m/z for $C_{14}H_{16}ClN_2O_5S^+$ 359.05; obtained 359.1

Preparation of AQP-0024

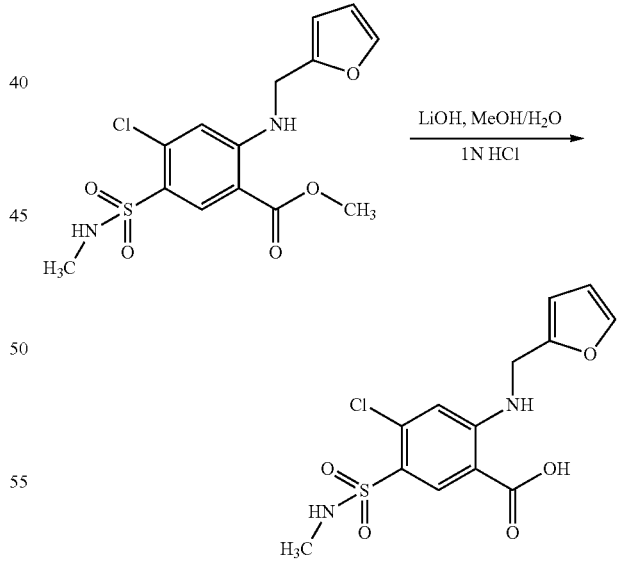

Reaction Conditions:

| | |
|---|---|
| Reaction | |
| Molarity | |
| Pressure | Atm |
| Temperature | 25 deg C. |

Reactants:

| Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C14H15ClN2O5S | ☑ | 358.80 | 1.000 | 0.279 | 0.100 | | | | | 358.80 | 0.100 |
| 2 | LiOH | ☐ | 42 | 5.5 | 1.533 | 0.065 | | | | | | 0.065 |

Solvents:

| Name | Ratio | Volume |
|---|---|---|
| Methanol Water | | |

Products:

| Product | MF | Actual Mass (g) | Actual Mol | Yield | Purity | MW | Eq | Theo Mol (mmol) | Theo Mass (µg) | FM |
|---|---|---|---|---|---|---|---|---|---|---|
| 1 | C13H13ClN2O5S | 0.0805 | | | | | 1.000 | 0.279 | 0.00 | |

Preparation:
A mixture of 100 mg (0.279 mmol) ester and 65 mg (1.533 mmol) LiOH.H$_2$O in 3 ml 3:1 MeOH/H$_2$0 was stirred at r.t. TLC in 50% EtOAc in hexanes, after ~6 hours.

Added another 1.0 ml of 0.5M LiOH in 3:1 MeOH/H$_2$O. Stirred overnight. After 24 hr TLC indicated completion of reaction. Added 1N HCl to the reaction solution. Filtered the precipitate and washed with distilled water. Dried to obtain an off-white fluffy solid.

$^1$HNMR (CDCl$_3$, 300 MHz) ppm 2.40 (d, J=5.1 Hz, 3H), 4.58 (d, J=5.7 Hz, 2H), 6.38 (t, J=9 Hz, 1H), 6.425 (t, J=2.1 Hz, 1H), 7.10 (s, 1H), 7.34 (d, J=5.1 Hz, 1H), 7.62 (q, J=0.9 Hz, 1H), 8.34 (s, 1H), 8.68 (t, 1H)

C13NMR (CDCl$_3$, 75 MHz) ppm 29, 108.9, 111.42, 114.5, 122.5, 136.0, 137.0, 143.63, 152.0, 153.5, 169

MS API-ES calculated m/z for C13H14ClN2O5S$^+$ 345.03; obtained 345.1.

Furosemide is AQP-0025

Preparation of AQP-0026

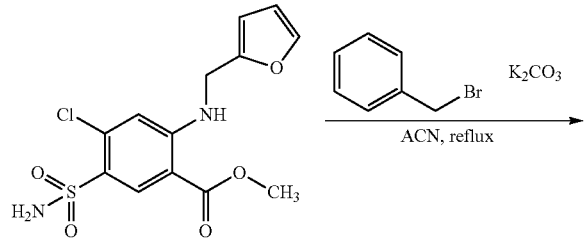

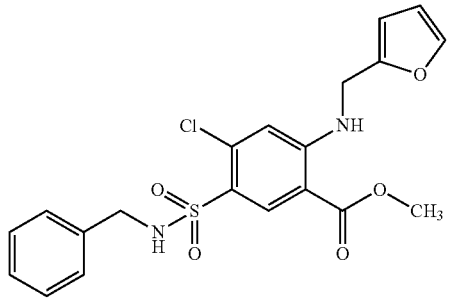 [SMILES: COC(=O)c1cc(S(=O)(=O)NCc2ccccc2)c(Cl)cc1NCc1ccco1]

Reaction Conditions:

| | |
|---|---|
| Reaction Molarity | |
| Pressure | Atm |
| Temperature | 100 deg C. |

Reactants:

| Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C13H13ClN2O5S | ☑ | 344.77 | 1.000 | 1.000 | 0.34477 | | | | | 344.77 | 0.345 |
| 2 | C7H7Br | ☐ | 171.03 | 2.000 | 2.000 | 0.342 | | | | | 171.03 | 0.342 |
| 3 | CK2O3 | ☐ | 138.21 | 2.000 | 2.000 | 0.276 | | | | | 138.21 | 0.276 |

Solvents:

| Name | Ratio | Volume |
|---|---|---|
| Acetonitrile | | |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C20H19ClN2O5S | 0.177 | 0.407 | 40.7 | | 434.89 | 1.000 | 1.000 | 0.435 | 434.89 |

Preparation:

In a 25 ml RBF, containing a magnetic stir bar was dissolved 1 mmol of the methyl ester of furosemide in ACN (2 ml). To the above solution was added $K_2CO_3$ in excess and refluxed for ~6 h. TLC indicated a high percentage of the desired product (non-polar) and some of the di-substituted product (even less polar) and also some of the starting material. Quenched the reaction with water and extracted into EtOAC while washing with water. Concentrated down the organic layer and obtained an orange color crude oil. The residue was purified via Biotage (starting with 10% ethyl acetate/hexanes and increasing the ratio up to 80% of EtOAc, column size 25+M). Collected three fractions. Concentrated the desired fraction and recrystallized in a mixture of Hexanes/DCM. Obtained glassy colorless crystals. Named NTF-AQP-027B.

'HNMR (CDCl$_3$, 300 MHz) ppm 3.89 (s, 3H), 4.08 (d, J=6 Hz, 2H), 4.49 (d, J=6 Hz, 2H), 5.03 (t, J=6 Hz, 1H), 6.29 (d, J=3 Hz, 1H), 6.37 (d, J=3 Hz, 1H), 6.82 (s, 1H), 7.24 (m, 5H), 7.41 (d, J=0.6 Hz, 1H), 8.59 (d, J=1.2 Hz, 1H), 8.65 (BrS, 1H)

C13NMR (CDCl$_3$, 75 MHz) ppm 41.0, 48.0, 52.53, 108.22, 109.0, 110.92, 114.0, 123.0, 128.35, 129.07, 136.0, 137.5, 143.03, 150.05, 153.50, 168.0

MS API-ES calculated for C20H20ClN2O5S$^+$ 435.90; obtained 435.1

Preparation of AQP-0027

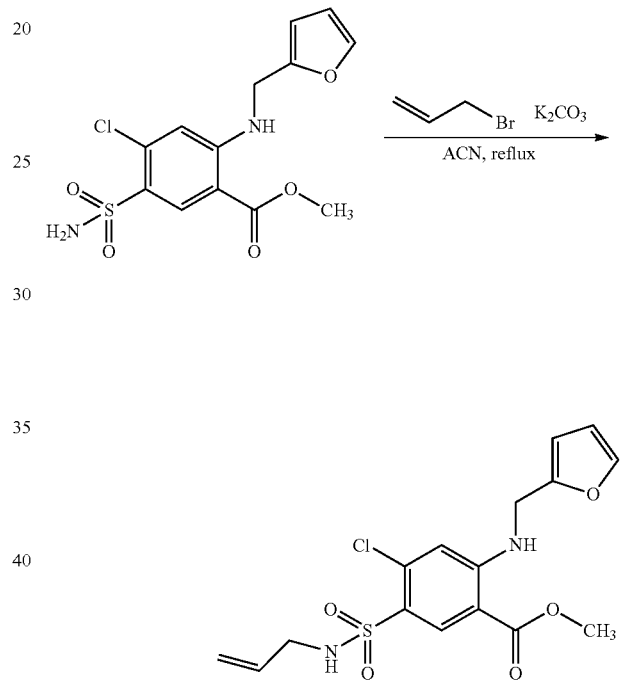

Reaction Conditions:

| | |
|---|---|
| Reaction | |
| Molarity | |
| Pressure | Atm |
| Temperature | 100 deg C. |

Reactants:

| | Reactant MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C13H13ClN2O5S | ☑ | 344.77 | 1.000 | 1.000 | 0.34477 | | | | | 344.77 | 0.345 |
| 2 | C3H5Br | ☐ | 120.98 | 1.000 | 1.000 | 0.121 | | | | | 120.98 | 0.121 |
| 3 | CK2O3 | ☐ | 138.21 | 1.000 | 1.000 | 0.138 | | | | | 138.21 | 0.138 |

Solvents:

| Name | Ratio | Volume |
|---|---|---|

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C16H17ClN2O5S | 0.172 | 0.447 | 44.7 | | 384.83 | 1.000 | 1.000 | 0.385 | 384.83 |

Preparation:

To a 25 ml RBF containing a magnetic stir bar was added the furosemide methyl ester (1 mmol) and dissolved in 1 ml ACN. To the above solution was added $K_2CO_3$ (2 eq.) and allyl bromide (2eq) and refluxed for ~6 h. TLC indicated two less polar products the mono substituted being more significant over the other. Quenched with water, extracted into EtOAc, washed with water and combined the desired organic layer and concentrated. Obtained an orange color crude oil. The residue was purified via Biotage (started with 10% EtOAc/Hexanes and increased the ratio up to 80% EtOAc/Hexanes, column size 25+M). Collected three fractions. The desired fraction was concentrated and recrystallized in a mixture of Hexanes/DCM. Obtained glassy, colorless crystals. Named NTF-AQP-028B.

'HNMR in $CDCl_3$ (300 MHz) ppm 1.60 (s, 1H), 3.58 (m, 2H), 3.95 (s, 3H), 4.46 (d, J=5.7 Hz, 2H), 4.84 (t, J=6.3 Hz, 1H), 5.20 (two overlapped doublets, geminal allyl Hs), 5.78 (m, vinyl allyl H), 6.36 (dd, 2H), 6.90 (s,1H), 7.35 (s, 1H), 8.65 (s, 1H), 8.80 (t, 1H)

13CNMR ($CDCl_3$, 75 MHz) ppm 40.66, 46.27, 52.53, 108.22, 108.89, 110.92, 113.91, 118.37, 122.98, 133.19, 136.30, 137.70, 143.04, 150.56, 153.49, 168

MS API-ES calculated for $C_{16}H_{18}ClN_2O_5S^+$ 385.84; obtained 385.

Preparation of AQP-0028

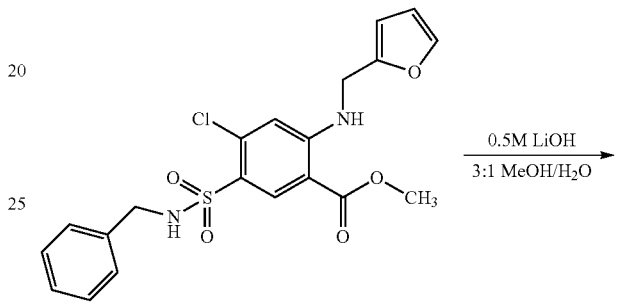

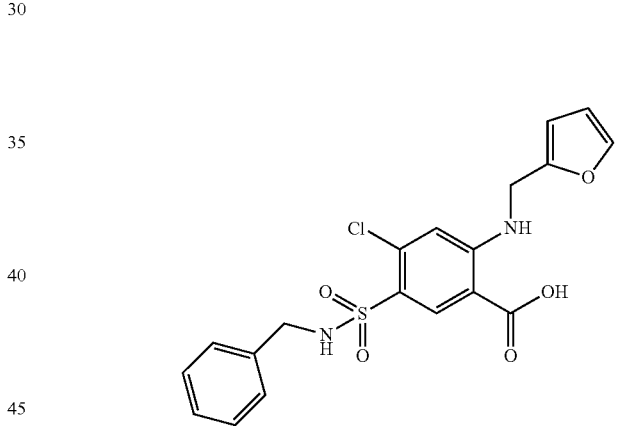

Reaction Conditions:

| Reaction Molarity | |
|---|---|
| Pressure | Atm |
| Temperature | 25 deg C. |

Reactants:

| | Reactant MF | Limit? | MW | Eq | Moles (mmol) | Sample Mass (g) | Vol (ml) | Molarity (M) | % d Wt | FM | Reactant Mass (g) |
|---|---|---|---|---|---|---|---|---|---|---|---|
| 1 | C20H19ClN2O5S | ☑ | 434.89 | 1.000 | 0.202 | 0.088 | | | | 434.89 | 0.088 |
| 2 | LiOH | ☐ | | 5.000 | 1.012 | | 2.023 | 0.5 | | | |

Solvents:

| Name | Ratio | Volume |
|---|---|---|
| Methanol Water | | |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C19H17ClN2O5S | 0.063 | 0.150 | 74.0 | | 420.87 | 1.000 | 0.202 | 0.085 | 420.87 |

Preparation:

To a 25 ml RBF containing a magnetic stir bar was added pyridinyl sufonamide methyl ester of Furosemide (88 mg, 0.202 mmol) and 0.5M LiOH in 3:1 MeOH/H$_2$O (2.023 ml, 1.012 mmol) and stirred for 24 h. After 24 h heated the reaction a little to get the reaction go to completion. After all the starting material was gone, quenched the reaction with 1N HCl (1 ml). Filtered the white precipitate that was formed and dried under vacuum to obtain a white powder (74% yield).

$^1$HNMR (DMSO-d$_6$, 300 MHz) ppm 4.07 (d, J=12 Hz, 2H), 4.56 (d, J=5.7 Hz, 2H), 6.36 (d, J=1.2 Hz, 1H), 6.44 (d, J=1.2 Hz, 1H), 6.99 (s, 1H), 7.15 (brm, 6H), 7.64 (s, 1H), 8.12 (t, J=6 Hz, 1H), 8.29 (s, 1H), 8.65 (t, J=6 Hz, 1H)

13CNMR (DMSO-d$_6$, 75 MHz) ppm 47.0, 108.52, 111.41, 124.15, 128.34, 128.88, 129.0, 138.00, 138.47, 142.50, 152.11, 153.5, 169.36

MS API-ES, Neg. Scan calculated for C19H18ClN2O5S$^+$ 421.87; obtained 419.0

Preparation of AQP-0029

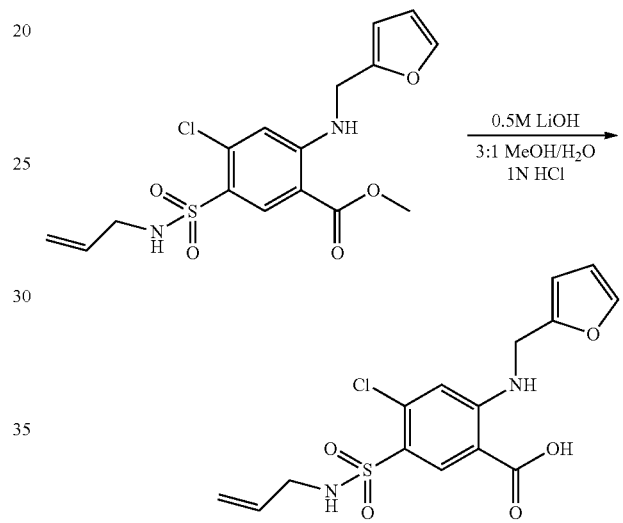

Reaction Conditions:

| | |
|---|---|
| Reaction Molarity | |
| Pressure | Atm |
| Temperature | 25 deg C. |

Reactants:

| Reactant | MF | Limit? | MW | Eq | Moles (mmol) | Sample Mass (g) | Vol (ml) | Molarity (molar) | d | % Wt | FM | Reactant Mass (g) |
|---|---|---|---|---|---|---|---|---|---|---|---|---|
| 1 | C16H17ClN2O5S | ☑ | 384.83 | 1.000 | 0.223 | 0.086 | | | | | 384.83 | 0.086 |
| 2 | | ☐ | | 1.000 | 0.223 | | | | | | | |
| 3 | LiOH | ☐ | | 5.000 | 1.117 | | 2.235 | 0.5 | | | | |

Solvents:

| Name | Ratio | Volume |
|---|---|---|
| Methanol Water | | |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C15H15ClN2O5S | 0.055 | 0.148 | 66.4 | | 370.81 | 1.000 | 0.223 | 0.083 | 370.81 |

Preparation:
A mixture of starting ester (0.086 mg, 0.223 mmol) and 0.5M LiOH in 3:1 MeOH/H$_2$O (2.235 ml, 1.117 mmol) was stirred at rt for 24 h. Heated the reaction mixture using the heat gun to get the reaction go to completion. 1.0 ml of 1N HCl was added to the reaction mixture to quench it and the white precipitate that was formed was filtered and suction dried to give 0.055 g (66%) white powder.

$^1$HNMR (DMSO-d$_6$, 300 MHz) ppm 3.45 (d, J=5.7 Hz, 2H), 4.65 (d, J=17.7, 2H), 5.10 (d, J=1.5, 1 H), 5.19 (d, J=1.5 Hz, 1H), 5.65 (m, 1H), 6.37 (d, J=3 Hz, 1H0, 6.42 (d, J=1.2 Hz, 1H), 7.10 (s, 1H), 7.62 (s, 1H), 7.77 (t, J=6 Hz, 1H), 8.43 (s, 1H), 8.67 (t, 5.4 Hz, 1H), 13.4 (brs, 11H)

13CNMR (DMSO-d$_6$, 75 MHz) ppm 45.62, 108.54, 109.22, 111.41, 114.59, 117.19, 124.06, 135.14, 135.81, 137.30, 143.62, 152.08, 153.54, 169.38

Ms API-ES Neg. Scan calculated for C15H16ClN2O5S$^+$ 371.82; obtained 368.9

Preparation of AQP-0030

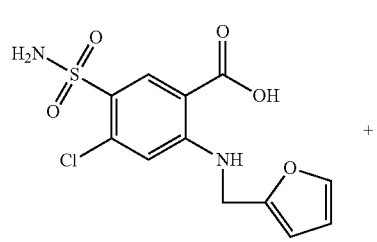

+

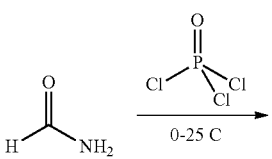

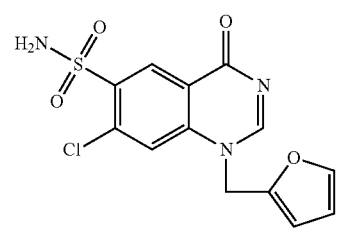

Reaction Conditions:

| | |
|---|---|
| Reaction | |
| Molarity | |
| Pressure | Atm |
| Temperature | 0-25° C. |

Reactants:

| Reactant | MF | Limit? | MW | Eq | Moles (mmol) | Sample Mass (g) | Vol (ml) | Molarity | d (g/ml) | % Wt | FM | Reactant Mass (g) |
|---|---|---|---|---|---|---|---|---|---|---|---|---|
| 1 | C12H11ClN2O5S | ☑ | 330.74 | 1.000 | 0.907 | 0.300 | | | | | 330.74 | 0.300 |
| 2 | CH3NO | ☐ | 45.04 | 30.00 | 27.2 | 1.226 | 1.085 | | 1.13 | | 45.04 | 1.226 |
| 3 | Cl3OP | ☐ | 153.33 | 4.000 | 3.63 | 0.556 | 0.337 | | 1.65 | | 153.33 | 0.556 |

Solvents:

| Name | Ratio | Volume |
|---|---|---|
| Formamide | | |

Products:

| Product | MF | Actual Mass | Actual Mol | Yield | Purity | MW | Eq | Theo Mol (mmol) | Theo Mass (g) | FM |
|---|---|---|---|---|---|---|---|---|---|---|
| 1 | C13H10ClN3O4S | | | | | 339.75 | 1.000 | 0.907 | 0.308 | 339.75 |

Preparation:

The starting compound was suspended in formamide and was stirred vigorously. The 25 mL round bottom flask containing the reaction was then placed in an ice bath. The POCl3 was added to a drop funnel and adapted to the reaction flask. The POCl3 was added dropwise over a period of 30 minutes, regulating the temp. below 25 degrees C. After the addition of POCl3 the reaction continued for an additional 45 minutes at room temp. before being stopped. As the reaction proceeded, stirred stopped due to the viscosity of the solution, because of this, 2 more equivalents of formamide was added to reinitiate stirring. To the reaction flask was added ~20 mL of cold DI water, when a precipitate fell out of solution that was buchner filtered. TLC analysis of this solid indicated starting material was present. Recrystalization was attempted in DMF, which was unsuccessful, so this was resubmitted to the previous reaction conditions. The filtrate from the initial reaction had formed crystals that were filtered from the water and upon TLC and NMR analysis indicated that this was the desired product.

$^1$H NMR analysis: 8.857 (s, 1H), 8.668 (s, 1H), 8.071 (s, 1H), 7.512 (m, 1H), 6.645 (m, 1H), 6.434 (m, 1H), 5.52 (s, 2H), 3.359 (s, 2H).

$^{13}$C NMR analysis: 155.98, 147.58, 144.19, 142.18, 137.50, 130.06, 119.67, 118.36, 110.95, 110.62, 78.63, 78.20, 77.76.

MS API-ES, Pos. Scan calculated for C13H11ClN3O4S$^+$ 340.75; octaned 340.0

Preparation of AQP-0031

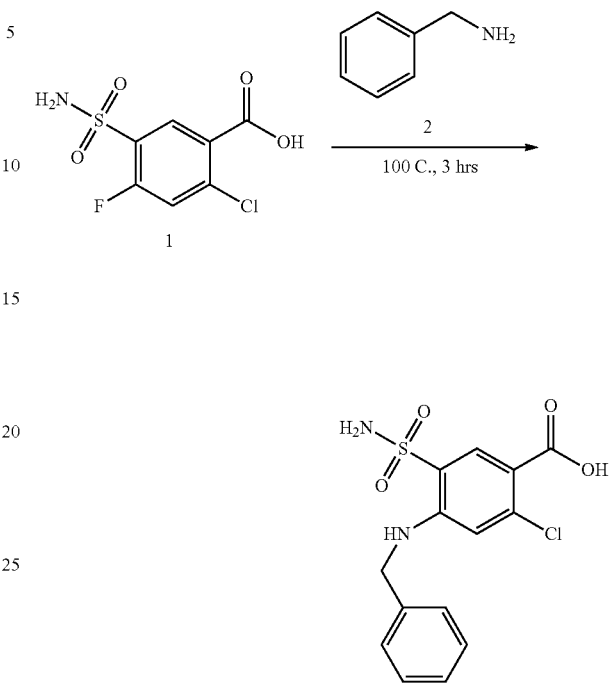

Reaction Conditions:

| Reaction | |
| Molarity | |
| Pressure | |
| Temperature | |

Reactants:

| | Reactant MF | Limit? | MW | Eq | Moles (mmol) | Sample Mass (g) | Vol (ml) | Molarity | d (g/ml) | % Wt | FM | Reactant Mass (g) |
|---|---|---|---|---|---|---|---|---|---|---|---|---|
| 1 | C7H5C1FNO4S | ☑ | 253.64 | 1.000 | 0.394 | 0.100 | | | | | 253.64 | 0.100 |
| 2 | C7H9N | ☐ | 107.15 | 27.00 | 10.65 | 1.141 | 1.164 | | 0.98 | | 107.15 | 1.141 |

Solvents:

| Name | Ratio | Volume |
|---|---|---|
| | | |

Products:

| | Product MF | Actual Mass | Actual Mol | Yield | Purity | MW | Eq | Theo Mol (mmol) | Theo Mass (g) | FM |
|---|---|---|---|---|---|---|---|---|---|---|
| 1 | C14H13C1N2O4S | | | | | 340.78 | 1.000 | 0.394 | 0.134 | 340.78 |

Preparation:

Compound 1 was dissolved in 1 mL of compound 2 and heated to 100 C and monitored by TLC until complete. When complete, as indicated by TLC, the reaction was removed from the heat. A pale yellow goo remained, containing crystals. To this mixture was added 1M HCl and this stirred for 10 min. At this time, a precipitate fell out of solution that was subsequently filtered to yield the pure product as indicated by NMR.

1H NMR: 8.25 (s, 1H), 7.5-7.2 (m, 5H), 6.71 (s, 1H), 4.54 (s, 2H), 4.0 (s, 1H), 3.3 (s, 2H).

Ms API-ES Neg. Scan calculated for C14H12C1N2O4S—339.02.; obtained 339.2

Preparation of AQP-0032

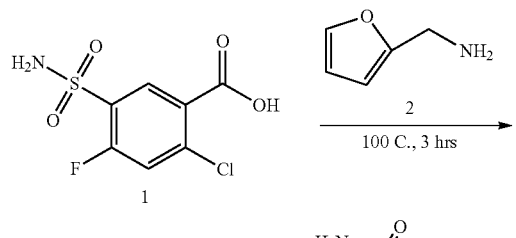

Preparation:

Compound 1 was dissolved in compound 2 and heated to 100 C and was monitored by TLC until complete (3.5 hrs). When complete, 1 M HCl (~30 mL) was added to the reaction mixture and ~30 mL of toluene was added to the reaction and this stirred for 5 minutes in the flask. This was poured from the reaction vessel into a separatory funnel. An emulsion was formed that was then washed with brine. The water layer was then separated from the toluene. At this time, the toluene layer was evaporated and a precipitate began to fall out of the water layer. This flask containing the water and precipitate sat overnight, at which time more solid fell out of solution. This white crystalline solid was filtered and washed with DI water, then EtOAc. Upon NMR evaluation, the desired product had been formed.

1H NMR data: 8.06 (s, 1H), 7.54 (m, 1H), 6.77 (s, 1H), 6.34 (m, 1H), 6.30 (m, 1H), 4.39 (s, 2H), 3.73 (s, 1H).

Ms API-ES Neg. Scan calculated for C12H10ClN2O5S—329.00.; obtained 329.2

Preparation of AQP-0033

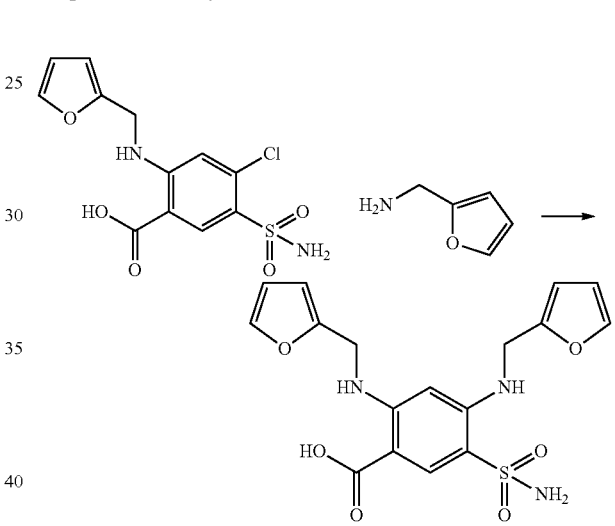

Reaction Conditions:

| | | |
|---|---|---|
| Reaction | | |
| Molarity | | |
| Pressure | | |
| Temperature | 100° C. | |

Reactants:

| Reactant | MF | Limit? | MW | Eq | Moles (mmol) | Sample Mass (g) | Vol (ml) | Molarity | d (g/ml) | % Wt | FM | Reactant Mass (g) |
|---|---|---|---|---|---|---|---|---|---|---|---|---|
| 1 | C7H5C1FNO4S | ☑ | 253.64 | 0.985 | 11.83 | 3.00 | | | | | 253.64 | 3.00 |
| 2 | C5H7NO | ☐ | 97.12 | 27.000 | 324 | 31.5 | 30 | | 1.05 | | 97.12 | 31.5 |

Solvents:

| Name | Ratio | Volume |
|---|---|---|
| | | |

Reaction Conditions:

| | |
|---|---|
| Reaction | |
| Molarity | |
| Pressure | |
| Temperature | |

Products:

| Product | MF | Actual Mass | Actual Mol | Yield | Purity | MW | Eq | Theo Mol (mmol) | Theo Mass (g) | FM |
|---|---|---|---|---|---|---|---|---|---|---|
| 1 | C12H11C1N2O5S | | | | | 330.74 | 1.000 | 12.01 | 3.97 | 330.74 |

Reactants:

| | Reactant MF | Limit? | MW | Eq | Moles (mmol) | Sample Mass (g) | Vol | Molarity | d | % Wt | FM (g/mol) | Reactant Mass (g) |
|---|---|---|---|---|---|---|---|---|---|---|---|---|
| 1 | C12H11C1N2O5S | Yes | 330.744 | 0.024 | 0.5 | 0.165 | | | | | 331 | 0.165 |
| 2 | C5H7NO | No | 97.115 | 2.000 | 41.2 | 4 | | | | | 97 | 4.00 |

Solvents:

| | Name | Solvent Ratio | Volume (ml) |
|---|---|---|---|
| 1 | EtOAc | | 6.0 |

Products:

| Product | MF | Actual Mass (mg) | Actual Mol (μmol) | Yield (%) | Purity | MW | Eq | Theo Mol (mmol) | Theo Mass (g) | FM (g/mol) |
|---|---|---|---|---|---|---|---|---|---|---|
| 1 | C17H17N3O6S | 0.015 | 0.038 | 0.00019 | | 391.398 | 1.000 | 20.59 | 8.06 | 391 |

Preparation:
To a 25 ml RBF containing a magnetic stirring bar was added Furosemide (165 mg, 0.50 mmol) and 4.0 ml furfuryl amine. The mixture was stirred under nitrogen at 125 deg. C. for 72 hrs. T solution turned amber. After 72 hrs, the reaction was allowed to cool while a stream of Nitrogen was passed over the reaction, thus evaporating most of the excess furfuryl amine. The residue was then dissolved in 15 ml EtOAc, transferred to a seperatory funnel with 10 ml EtOAc, and washed twice with 20 ml 1N HCl. The organic layer was dried over MgSO4, filtered and concentrated to give a dark brown film.

TLC indicated a more mobile blue fluorescent spot. Flash chromatography on 40 ml silica using 50% EtOAc/hexanes removed most of the dark material. however, a second chromatography on 15 ml silica gel was need to provide a clean sample as a yellow semi-crystalline solid, 15 mg.

MS API-ES, Neg. Scan calculated for C17H16N3O6S—: 390.08; obtained 390.20

Preparation of AQP-0035

-continued

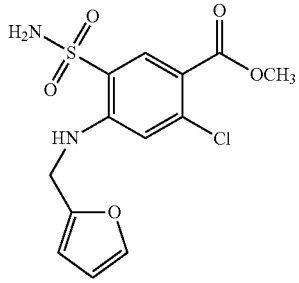

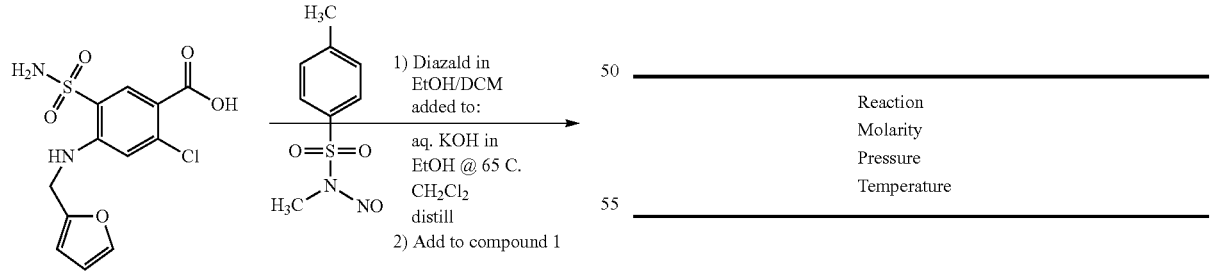

Reaction Conditions:

| | |
|---|---|
| | Reaction |
| | Molarity |
| | Pressure |
| | Temperature |

Reactants:

| | Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|---|
| 1 | | C12H11ClN2O5S | ☑ | 330.74 | 1.000 | 0.907 | .300 | | | | | 330.74 | 0.300 |
| 2 | Diazald | C8H10N2O3S | ☐ | 214.24 | 10.00 | 9.07 | 1.943 | | | | | 214.24 | 1.943 |

Solvents:

| Name | Ratio | Volume |
|------|-------|--------|

Products:

| Product | MF | Actual Mass (g) | Actual Mol (mmol) | Yield (%) | Purity | MW | Eq | Theo Mol (mmol) | Theo Mass (g) | FM |
|---------|----|-----------------|-------------------|-----------|--------|----|----|-----------------|---------------|----|
| 1 | C13H13ClN2O5S | .201 | 0.583 | 64.3 | | 344.77 | 1.000 | 0.907 | 0.313 | 344.77 |

Preparation:

To a solution of 4 g KOH in 3 mL water and 3 mL EtOH in a 100 mL round bottom flask equipped with teflon joined distillation head, chilled condenser with receiving flask in an ice-water bath, and addition funnel was added. 5 mL DCM was then added and the two phase system was heated to 65 C. Once distillation had initiated, a solution of 1.07 g (5 mmol) Diazald in 5 mL DCM and 2.5 mL EtOH was added over 15 min. Once the distillation solutions was no longer yellow, the resulting yellow distillate was stoppered and stored in an ice bath until used.

An Erlenmeyer flask was prepared with 0.300 g (0.907 mmol) of compound 1. flask was treated with CH2N2 solution until a faint yellow color persisted, gas evolution was observed, stoppered loosely and monitored by TLC until complete. After 30 min. TLC indicated that a pure product remained. Hexanes were added to the flask to quench the reaction and the resulting white solid was filtered to give 201 mg of white solid.

1H NMR: 7.96 (s, 1H), 7.56 (s, 1H), 6.95 (s, 2H), 6.66 (m, 1H), 6.27 (m, 2H), 4.35 (s, 2H), 3.70 (s, 11H), 3.29 (s, 3H).

MS API-ES, Neg. Scan calculated for C13H10ClN3O4S$^-$ 343.00; obtained 343.2

Preparation of AQP-0036

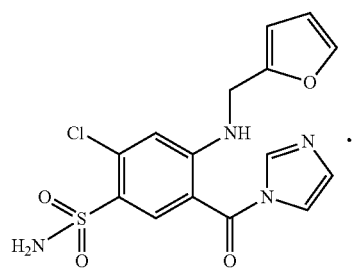

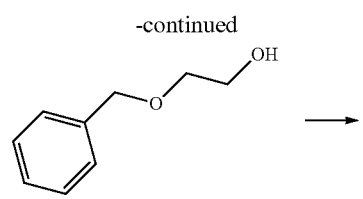

-continued

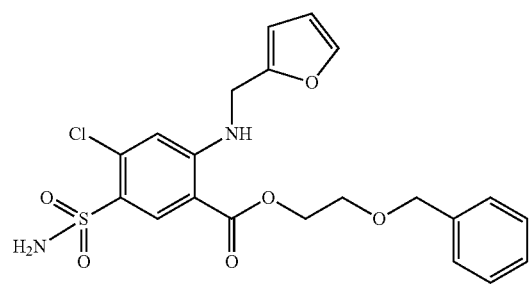

Reaction Conditions:

| Reaction | |
|----------|---|
| Molarity | |
| Pressure | |
| Temperature | |

Reactants:

| Reactant | MF | Limit? | MW | Eq | Moles (mmol) | Sample Mass (g) | Vol (ml) | Molarity | d (g/ml) | % Wt | FM | Reactant Mass (g) |
|----------|----|--------|----|----|--------------|-----------------|----------|----------|----------|------|----|-------------------|
| 1 intermediate | C15H13ClN4O4S | ☑ | 380.81 | 1.000 | 0.263 | 0.100 | | | | | 380.81 | 0.100 |
| 2 2-benzyloxy-ethanol | C9H12O2 | ☐ | 152.19 | 2.0 | 0.525 | 0.080 | 0.075 | | 1.07 | | 152.19 | 0.080 |

Solvents:

| Name | Ratio | Volume |
|------|-------|--------|

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C21H21N2O6S | 0.032 | 0.069 | 26.2 | | 464.92 | 1.000 | 0.263 | 0.122 | 464.92 |

Preparation:

To a 25 ml RBF containing a magnetic stir bar was added the imida zolide of Furosemide (0.100 mg) and 2-benzyloxy ethanol (0.075 mL) and dissolved in 2 ml EtOAc. Let the above solution stir at rt for 1 h. TLC (50% EtOAc in Hexanes) indicated a less polar spot, the top spot is new, while the middle spot is the starting alcohol.

Heating the above solution with a heat gun to drive the reaction further in increments of heating every 5 minutes, and this was done five times. The new less polar spot became more predominant. The reaction mixture was concentrated and the desired compound was separated using flash chromatography. Evaporation of the solvents yielded a pale yellow solid.

1H NMR: 8.52 (m, 9H), 6.45 (m, 2H), 4.67 (m, 4H), 3.45 (m, 2H).

13C NMR: 167.19, 154.56, 152.98, 152.02, 143.61, 139.04, 137.52, 133.82, 129.16, 128.37, 127.86, 114.76, 111.39, 108.54, 72.98, 68.27, 41.21, 40.93, 40.37, 40.10, 39.82

MS API-ES, Neg. Scan Calculated for $C_{21}H_{21}ClN_2O_6S^-$ 463.92; obtained 463.2

-continued

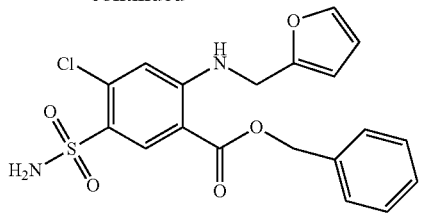

Reaction Conditions:

| Reaction |
| Molarity |
| Pressure |
| Temperature |

Reactants:

| Reactant | MF | Limit? | MW | Eq | Moles (mmol) | Sample Mass (g) | Vol (ml) | Molarity | d (g/ml) | % Wt | FM | Reactant Mass (g) |
|---|---|---|---|---|---|---|---|---|---|---|---|---|
| 1 furosemide | C13H13ClN2O4S | ☑ | 328.77 | 1.455 | 0.304 | .100 | | | | | 328.77 | 0.100 |
| 2 benzyl bromide | C7H7Br | ☐ | 171.03 | 2.0 | 0.418 | 0.072 | 0.05 | | 1.43 | | 171.03 | 0.072 |

Solvents:

| Name | Ratio | Volume |
|---|---|---|

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C19H17ClN2O5S | .051 | 0.121 | 58.0 | | 420.87 | 1.000 | 0.209 | 0.088 | 420.87 |

Preparation of AQP-0037

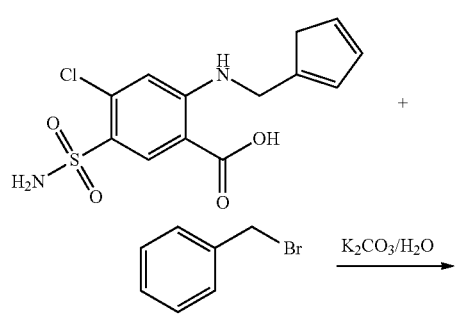

+

K₂CO₃/H₂O →

Preparation:

A 50 mL Erlenmeyer flask was equipped with a small stir bar and 0.100 g of furosemide was suspended in 1 mL of DI water. the 2 eq. of potassium carbonate was dissolved in 1 mL of DI water and added all at once to the Erlenmeyer flask. At this time all the furosemide went into the aqueous solution. benzyl bromide was then added to the flask, and this stirred for one hour at room temperature. To initiate the reaction, heating was added until a new, less polar spot was observed on the TLC plate. This yielded a pale yellow gooey precipitate that was filtered and dried to yield the product.

1H NMR: 7.65 (m, 8H), 6.50 (m, 1H), 6.04 (m,1H), 5.38 (m, 2H), 4.75 (m, 2H) 13C NMR: 166.77, 152.82, 151.24, 143.87, 138.00, 136.45, 134.87, 132.66, 131.93, 130.13, 129.53, 129.45, 129.41, 129.24, 129.12, 128.44, 111.25, 109.97, 35.39

MS API-ES, Neg. Scan Calculated for $C_{19}H_{17}ClN_2O_5S^-$ 420.87; obtained 419.2

Preparation of AQP-0038

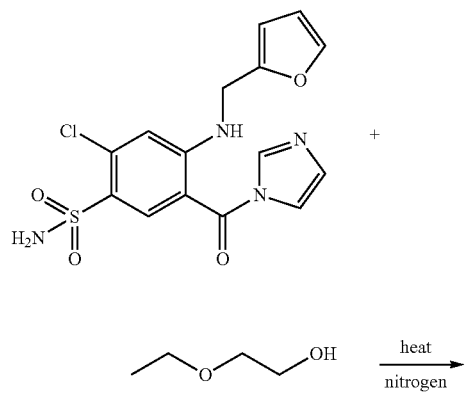

Reaction Condtions:

| | Reaction Molarity Pressure Temperature |
|---|---|

Reactants:

| Reactant | MF | Limit? | MW | Eq | Moles (mmol) | Sample Mass (g) | Vol | Molarity | % d Wt | FM | Reactant Mass (g) |
|---|---|---|---|---|---|---|---|---|---|---|---|
| 1 | C15H13ClN4O4S | ☑ | 380.81 | 1.000 | 0.998 | 0.380 | | | | 380.81 | 0.380 |
| 2 | C4H10O2 | ☐ | 90.12 | 2.000 | 1.996 | 0.180 | | | | 90.12 | 0.180 |

Solvents:

| Name | Ratio | Volume |
|---|---|---|

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C16H19ClN2O6S | 0.045 | 0.112 | 11.19 | | 402.85 | 1.000 | 0.998 | 0.402 | 402.85 |

Preparation:

To a 25 ml RBF containing a magnetic stir bar was added the imidazolide of Furosemide (0.380 mg, 0.998 mmol) and 2-ethoxyethanol (0.180 mg, 1.996 mmol) and dissolved in 2 ml EtOAc. Let the above solution stir at r.t. for 1 h. TLC (50% EtOAc in Hexanes) indicated a less polar spot.

The above solution was heated using a heat gun to drive the reaction further. TLC showed a less polar spot getting bigger but which after a certain point stopped growing. Concentrated the reaction mixture and separated the desired product using flash chromatography. Dried under vacuum to obtain a yellowish solid.

$^1$H NMR (CDCl$_3$, 300 MHz) ppm 1.10 (t, J=6.9 Hz, 3H), 3.50 (q, J=6.9 Hz, 2H), 3.67 (t, J=4.5 Hz, 2H), 4.37 (t, J=4.8 Hz, 2H), 4.60 (d, J=5.7 Hz, 2H), 6.415 (2d, 2H) 7.107 (s, 1H), 7.35 (s, 2H), 7.62 (dd, J=0.9 Hz, 1H), 8.42 (s, 1H)

C13 NMR (CDCl$_3$, 75 MHz) ppm 15.91, 64.99, 66.49, 68.39, 108.2, 108.55, 111.39, 114.9, 128.0, 133.9, 137.5, 143.63, 152.03, 152.94, 167.1

MS API-ES calculated for $C_{16}H_{20}ClN_2O6S^+$ 403.07; obtained (neg. scan) 401.2

Preparation of AQP-0039

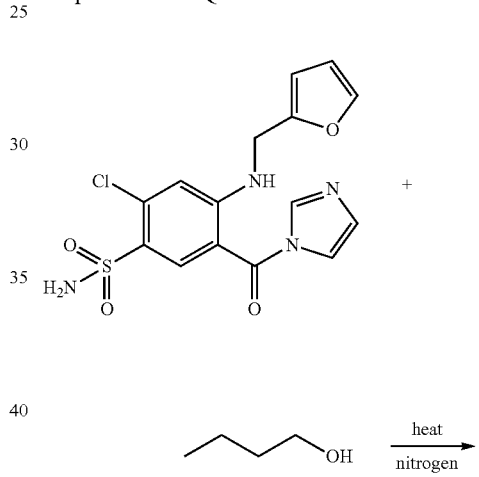

-continued

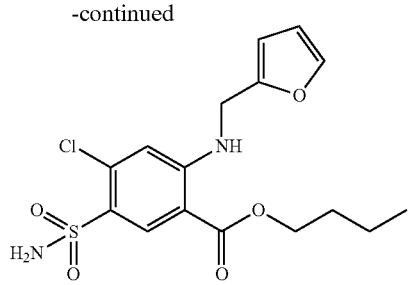

Reaction Conditions:

| Reaction |
|---|
| Molarity |
| Pressure |
| Temperature |

Reactants:

| Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C15H13ClN4O4S | ☑ | 380.81 | 1.000 | 0.998 | 0.380 | | | | | 380.81 | 0.380 |
| 2 | C4H10O2 | ☐ | 74.12 | 2.000 | 1.996 | 0.148 | | | | | 74.12 | 0.148 |

Solvents:

| Name | Ratio | Volume |
|---|---|---|

Products:

| Product | MF | Actual Mass | Actual Mol | Yield | Purity | MW | Eq | Theo Mol (mmol) | Theo Mass (g) | FM |
|---|---|---|---|---|---|---|---|---|---|---|
| 1 | C16H19ClN2O5S | | | | | 386.85 | 1.000 | 0.998 | 0.386 | 386.85 |

Preparation:

To a 25 ml RBF containing a magnetic stir bar was added the imidazolide of Furosemide (0.380 mg, 0.998 mmol) and 1-Butanol (0.148 mg, 1.996 mmol) and dissolved in 2 ml EtOAc. Let the above solution stir at rt for 1 h. TLC (50% EtOAc in Hexanes) indicated a less polar spot.

Heated the above solution using a heat gun to drive the reaction further. The less polar spot was getting bigger but after a certain point it stopped growing any more. Concentrated the reaction mixture and separated the desired product using flash chromatography. Concentrated and dried under vacuum to obtain a yellowish solid.

$^1$H NMR (CDCl$_3$, 300 MHz) ppm 0.92 (t, J=9.3 Hz, 3H), 1.40 (m, 2H), 1.68 (m, 2H), 4.26 (t, J=6.6 Hz, 2H), 4.59 (d, J=5.7 Hz, 2H), 6.41 (2d, J=3 Hz, 2H), 7.09 (s, 1H), 7.36 (s, 2H), 7.62 (t, J=0.9 Hz, 1H), 8.40 (s, 1H)

13C NMR (CDCl$_3$, 75 MHz) ppm 14.44, 19.56, 31.00, 65.38, 108.21, 108.57, 111.40, 127.86, 133.62, 137.39, 143.63, 152.03, 152.95, 167.28

MS API-ES calculated for $C_{16}H_{20}ClN_2O_5S^+$ 387.08; obtained (neg. scan) 385.2

Preparation of AQP-0041

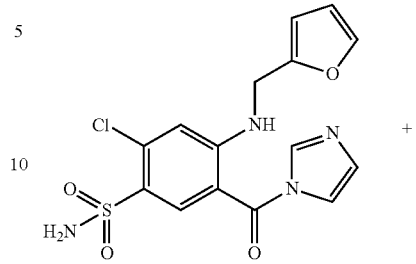

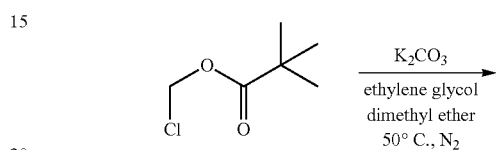

-continued

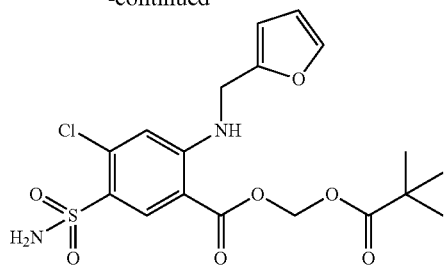

Reaction Conditions:

| Reaction |
|---|
| Molarity |
| Pressure |
| Temperature |

Reactants:

| Reactant | MF | Limit? | MW | Eq | Moles (mmol) | Sample Mass (g) | Vol | Molarity | d | % Wt | FM | Reactant Mass (g) |
|---|---|---|---|---|---|---|---|---|---|---|---|---|
| 1 | C12H11ClN2O5S | ☑ | 330.74 | 1.000 | 0.302 | 0.100 | | | | | 330.74 | 0.100 |
| 2 | C6H11ClO2 | ☐ | 150.60 | 2.000 | 0.605 | 0.091 | | | | | 150.60 | 0.091 |
| 3 | CK2O3 | ☐ | 138.21 | 1.500 | 0.454 | 0.063 | | | | | 138.21 | 0.063 |

Solvents:

| Name | Ratio | Volume |
|---|---|---|
| | | |

Products:

| Product | MF | Actual Mass (g) | Actual Mol (mmol) | Yield (%) | Purity | MW | Eq | Theo Mol (mmol) | Theo Mass (g) | FM |
|---|---|---|---|---|---|---|---|---|---|---|
| 1 | C18H21ClN2O7S | 0.020 | 0.045 | 14.87 | | 444.89 | 1.000 | 0.302 | 0.135 | 444.89 |

Preparation:

To an RBF containing furosemide (0.100 mg, 0.302 mmol) was $K_2CO_3$ (1.5 eq., 63 mg, 0.454 mmol)) and dissolved in ethyeleneglycol dimethyl ether (1 ml). Let stir at room temperature and under nitrogen for 10 min. Added the chloromethyl pivalate (91 mg, 0.605 mmol) and stirred under the same conditions for 30 min. Increased the temperature to 50° C. and stirred under nitrogen over night. TLC in 100% EtOAc showed a less polar product. Extracted the resulting reaction mixture into ethyl acetate and washed with water. Combined the organic layers and concentrated under vacuum. Purified by flash chromatography using 100% EtOAc as the solvent.

'HNMR NTF-AQP-035'HNMR in ($CDCl_3$, 300 MHz) ppm 1.28 (s, 9H), 3.30 (t, 2H), 4.27 (t, 2H), 4.59 (d, 2H), 5.85 (d, 1H), 5.95 (d, 1H), 6.3 (brd, 1H), 7.05 (s, 1H), 7.25 (s, 2H), 7.50 (s, 1H), 7.63 (brd, 1H), 8.40 (s, 1H) NTF-AQP-035'HNMR MS API-ES (neg. scan) calculated for $C19H24ClN2O6S^+$ 443.10; obtained 443.2

Preparation of AQP-0042

-continued

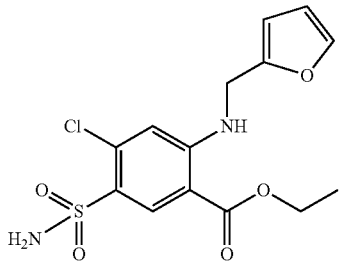

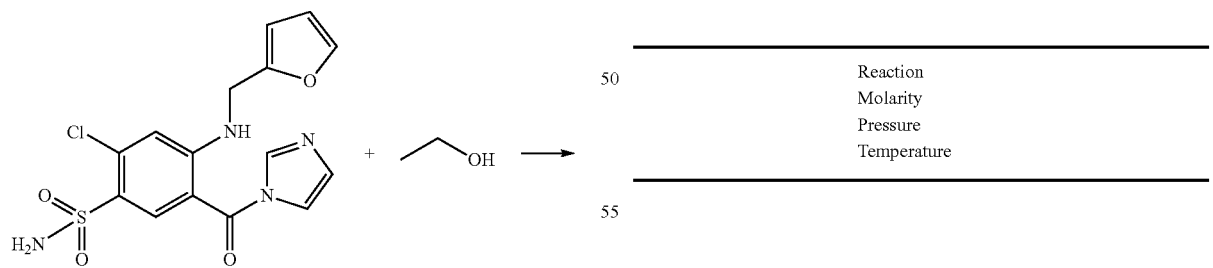

Reaction Conditions:

| | |
|---|---|
| Reaction | |
| Molarity | |
| Pressure | |
| Temperature | |

Reactants:

| Reactant | MF | Limit? | MW | Eq | Moles (mmol) | Sample Mass (g) | Vol (ml) | Molarity | d (g/ml) | % Wt | FM | Reactant Mass (g) |
|---|---|---|---|---|---|---|---|---|---|---|---|---|
| 1 | C15H13ClN4O4S | ☑ | 330.81 | 1.000 | 0.263 | .100 | | | | | 380.81 | 0.100 |
| 2 | C2H6O | ☐ | 46.07 | 2.0 | 0.525 | 0.024 | 0.031 | | 0.79 | | 46.07 | 0.024 |

Solvents:

| Name | Ratio | Volume |
|------|-------|--------|
|      |       |        |

Products:

| Product | MF | Actual Mass (g) | Actual Mol (mmol) | Yield (%) | Purity | MW | Eq | Theo Mol (mmol) | Theo Mass (g) | FM |
|---------|----|-----|------|------|--------|-----|-----|-------|-------|-------|
| 1 | C14H15ClN2O5S | 0.036 | 0.100 | 38.2 |  | 358.80 | 1.000 | 0.263 | 0.094 | 358.80 |

Preparation:

To a 25 ml RBF containing a magnetic stir bar was added the imida zolide of Furosemide (0.100 mg) and 2-benzyloxy ethanol (0.075 mL) and dissolved in 2 ml EtOAc. Let the above solution stir at rt (room temperature) for 1 h. TLC (50% EtOAc in Hexanes) indicated a less polar spot.

Heating the above solution with a heat gun to drive the reaction further in increments of heating every 5 minutes, and this was done five times. The new less polar spot became more predominant. The reaction mixture was concentrated and the desired compound was obtained by evaporation of the solvents.

1H NMR: 8.42 (m, 1H), 7.73 (s, 1H), 7.37 (s, 1H), 7.16 (s, 1H), 6.90 (m, 2H), 4.64 (m, 2H), 4.36 (m, 2H), 1.39 (m, 3H).

MS API-ES, Neg. Scan Calculated for $C_{14}H_{15}ClN_2O_5S^-$ 358.80; obtained 357.2

Appendices 1, 2 and 3 show compounds of the invention. Compounds in Appendix 3 are based on prodrug derivatives of furosemide.

Appendix I

| Structure | NB & Exp# | Originating Chemist | 1H-NMR | 13C-NMR | MS | HiRes MS | Reg # |
|---|---|---|---|---|---|---|---|
| (structure) | Bumetanide | Aldrch | | | | | |
| (structure) | GAF_2005_034 | Gary A. Flynn | NMR_gaf_2005_34-A_1 | NMR_gaf_2005_034-A_2 | MS_gaf_2005_034-A_1 | | AQP-0001 |
| (structure) | GAF_2005_034 | Gary A. Flynn | NMR_gaf_2005_34-B_1 | NMR_gaf_2005_034-B_2 | MS_gaf_2005_034-B_1 | | AQP-0002 |

| | | | | | |
|---|---|---|---|---|---|
| GAF_2005_036 | Gary A. Flynn | NMR_gaf_2005_036_1 | NMR_gaf_2005_036_2 | MS_gaf_2005_036_1 | AQP-0003 |
| GAF_2006_053 | Gary A. Flynn | NMR_gaf_2005_053_6 | NMR_gaf_2005_053_7 | MS_gaf_2005_053_1 | Yes AQP-0004 |
| GAF_2005_034 | Gary A. Flynn | NMR_gaf_2005_34-C_1 | NMR_gaf_2005_034-C_2 | | AQP-0005 |
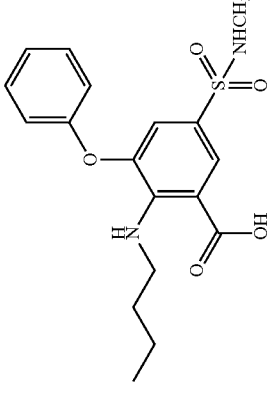
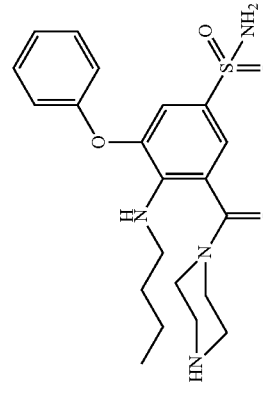
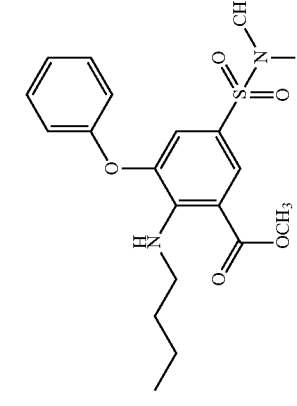

-continued

| | | | | | | |
|---|---|---|---|---|---|---|
| NTF-2006-1-004A | Nilmi T. Fernando | HNMR-NTF-2006-1-004A | 13C NMR-NTF-2006-1-004A | MS-NTF-2006-1-004A | Yes | AQP-0006 |
| NTF-2006-1-006A | Nilmi T. Fernando | HNMR-NTF-2006-1-006A | 13C NMR-NTF-2006-1-006A | MS-NTF-2006-1-006A | Yes | AQP-0007 |
| NTF-2006-1-007A | Nilmi T. Fernando | HNMR-NTF-2006-1-007A | 13C NMR-NTF-2006-1-007A | MS-NTF-2006-1-007A | Yes | AQP-0008 |

| | | | | | | |
|---|---|---|---|---|---|---|
| NTF-2006-1-008A | Nilmi T. Fernando | HNMR-NTF-2006-1-008A | 13C NMR-NTF-2006-1-008A | MS-NTF-2006-1-008A | Yes | AQP-0009 |
| NTF-2006-1-009A | Nilmi T. Fernando | HNMR-NTF-2006-1-009A | 13C NMR-NTF-2006-1-009A | MS-NTF-2006-1-009A | Yes | AQP-0010 |
| NTF-2006-1-010A | Nilmi T. Fernando | HNMR-NTF-2006-1-010A | 13C NMR-NTF-2006-1-010A | MS-NTF-2006-1-010A | Yes | AQP-0011 |

-continued
| Registered 050307 | | |
|---|---|---|
| 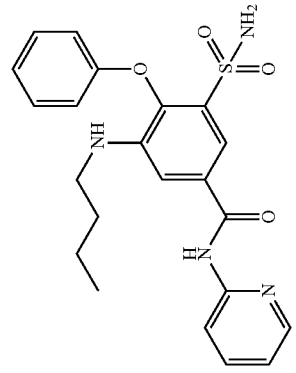 | Nilmi T. Fernando | AQP-0012 |
| 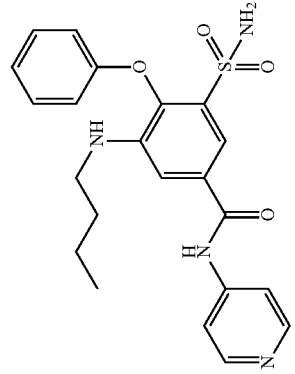 | Nilmi T. Fernando | AQP-0013 |
| 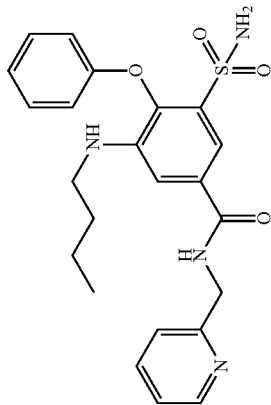 | Nilmi T. Fernando | AQP-0014 |

| AQP-0015 | Nilmi T. Fernando | 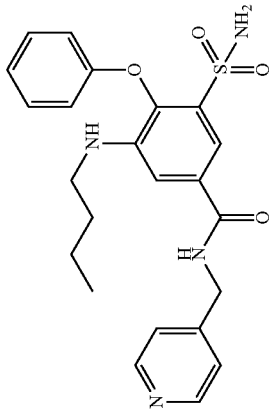 |
| AQP-0016 | Nilmi T. Fernando | 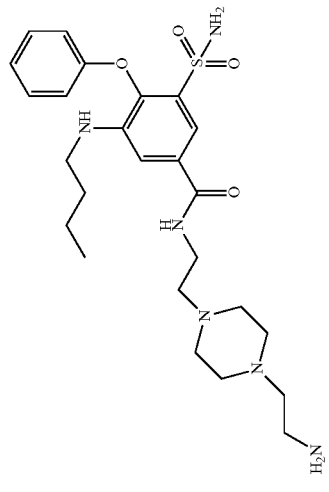 |
| AQP-0017 | Nilmi T. Fernando | 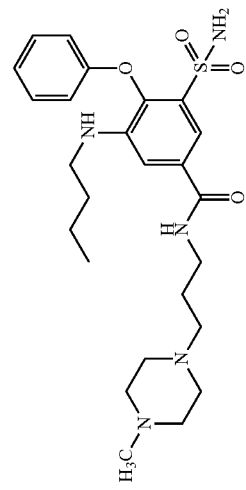 |

| | | | | | |
|---|---|---|---|---|---|
| NTF-AQP-018A | Nilmi T. Fernando | HNMR-NTF-AQP-018A | 13CNMR-NTF-AQP-018A | MS-NTF-AQP-018A | No | AQP-0022 |
| | Gary A. Flynn | | | | | AQP-0020 |
| | Gary A. Flynn | | | | | AQP-0019 |

| | | | | | |
|---|---|---|---|---|---|
|  | NTF-AQP-018B | Nilmi T. Fernando | HNMR-NTF-AQP-018B | 13CNMR-NTF-AQP-018B | MS-NTF-AQP-018B | No | AQP-0023 |
|  | NTF-AQP-019A | Nilmi T. Fernando | HNMR-NTF-AQP-019A | 13CNMR-NTF-AQP-019A | MS-NTF-AQP-019A | No | AQP-0024 |
|  | Furosemide | Purchased | | | | | AQP-0025 |

| | | | -continued | |
|---|---|---|---|---|
| NTF-AQP-027B | Nilmi T. Fernando | HNMR-NTF-AQP-027B | | AQP-0026 |
| NTF-AQP-028B | Nilmi T. Fernando | HNMR-NTF-AQP_028B | | AQP-0027 |
| NTF-AQP-029 | Nilmi T. Fernando | HNMR-NTF-AQP-029 | | AQP-0028 |

| | | | |
|---|---|---|---|
| 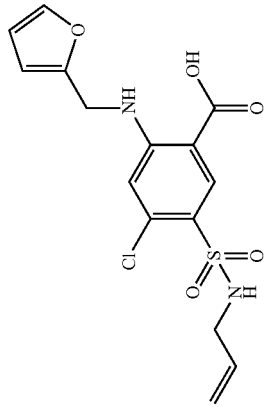 | NTF-AQP-030 | Nilmi T. Fernando | HNMR-NTF_AQP-030 | AQP-0029 |
| 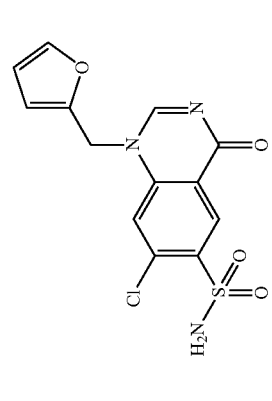 | HNP-AQP-001 | Heather Perry | | AQP-0030 |
| 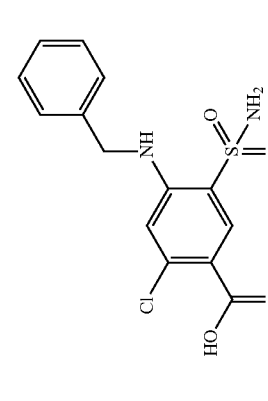 | | Heather Perry | Need MS | AQP-0031 |
| 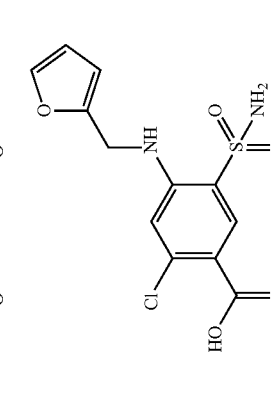 | | Heather Perry | Need MS | AQP-0032 |

| | | | |
|---|---|---|---|
|  | Gary A. Flynn | MS_gaf_2007_061-A_1 OK M+ = 391.2 | AQP-0033 |
|  | Purchased | | AQP-0034 |
|  | Heather Perry | | AQP-0035 |
|  | Heather Perry | | AQP-0036 |

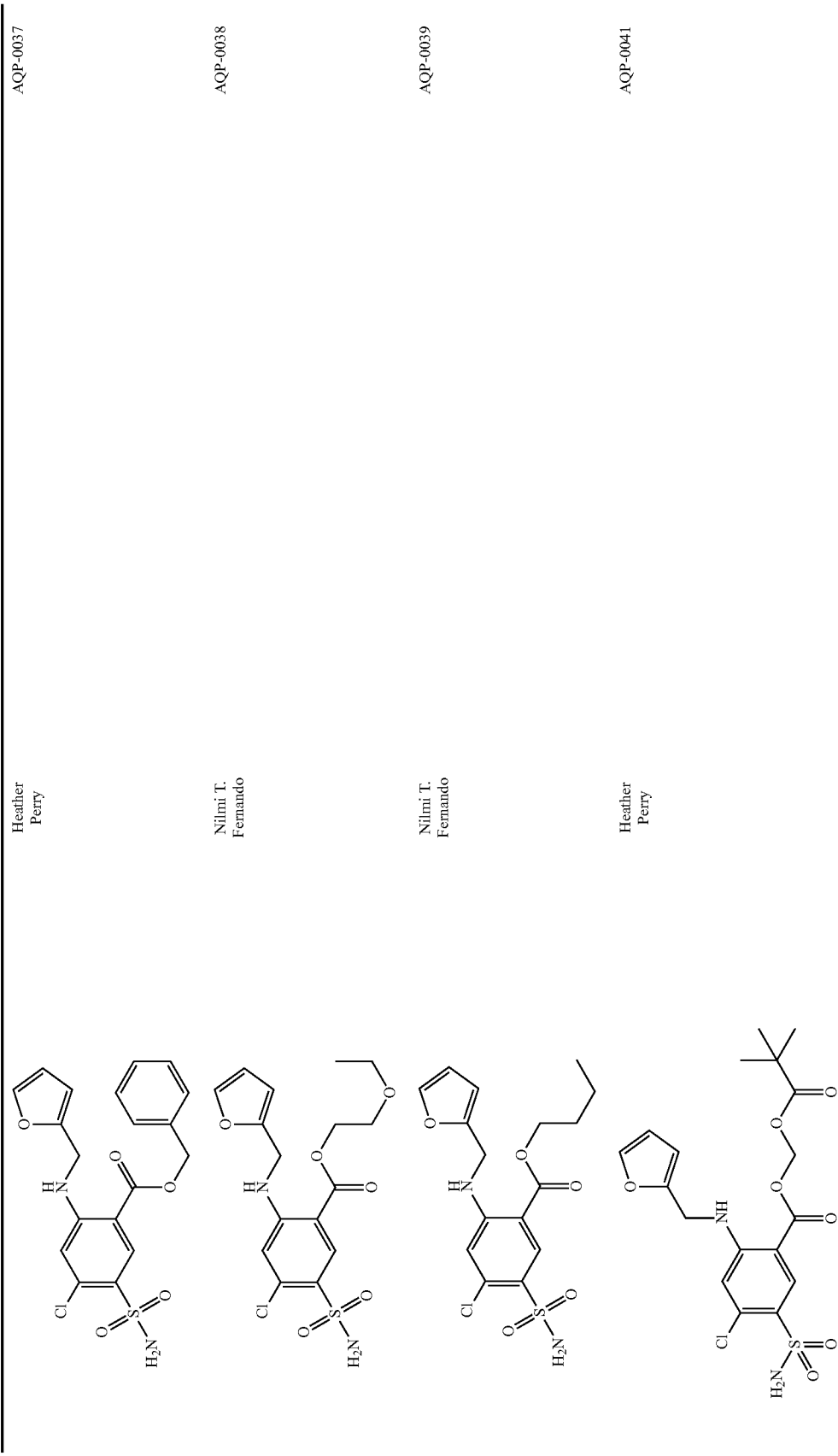

-continued

| | Heather Perry | | | | | | AQP-0042 |
|---|---|---|---|---|---|---|---|
| Structure | Amount Prepared | Comments | Amount Given to Yool Group | Achieved Remaining | AQP-1 effect | AQP-4 effect | |
| [structure: ethyl ester of furosemide-like compound with furfurylamine, chloro, and sulfamoyl groups] | | | | | | −35% block at 100 μM | |
| [structure: 3-phenoxy-4-butylamino-5-sulfamoyl benzoic acid (bumetanide)] | 164 mg | | | | | | |
| [structure: methyl ester of bumetanide, 3-phenoxy-4-butylamino-5-sulfamoyl benzoate] | | Methyl Ester of Bumetanide prepared to improve cellular transport. | 20 mg given 080305 | 140 mg | | Improved potency over bumetanide ~30% block at 1 μM extracellularly | |

-continued

| Structure | | | | |
|---|---|---|---|---|
| (methyl ester, methyl sulfonamide) | 110 mg | Methyl sulfonamide derivative and methyl ester of Bumetanide prepared to evaluate SAR of sulfonamide group. Intermediate to analog below. | 20 mg given 080305 | 90 mg | Improved potency over bumetanide ~40% block at 10 µM extracellularly |
| (carboxylic acid, methyl sulfonamide) | 70 mg | Methyl sulfonamide of Bumetanide prepared to evaluate SAR of sulfonamide group. | 20 mg given 080305 | 50 mg | Improved block ~40% at 100 µM |
| (piperazine carboxamide, sulfonamide) | 150 mg | Piperazine carboxamide of Bumetanide prepared to evaluate SAR of carboxyl group. | 20 mg given 080306 | 130 | |

-continued

| | | | |
|---|---|---|---|
| 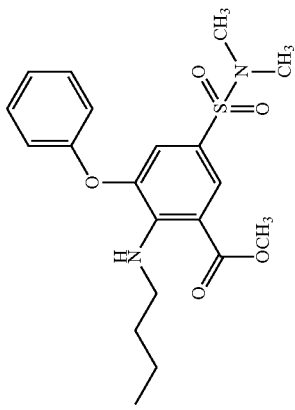 | 20 mg | Dimethyl sulfonamide derivative and methyl ester of Bumetanide prepared to evaluate SAR of sulfonamide group. Compound not given for testing | Compound not given for testing | NA |
| 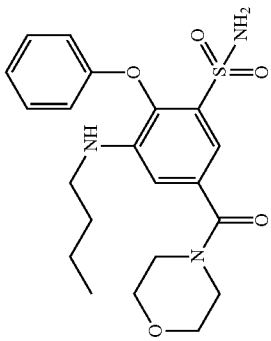 | 190 mg | Morpholine carboxamide of Bumetanide prepared to evaluate SAR of carboxyl group | 50 mg given 101006 | 134.2 mg | 70% Activation at 10 μM |
| 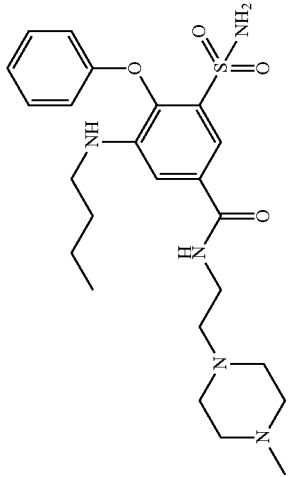 | 169 mg | 2-(4-Methylpiperazine-1-yl) ethanamine carboxamide of Bumetanide to evaluate SAR of caboxyl | 50 mg given 101006 | 102.8 mg | 110% activation at 10 |

| | | | | |
|---|---|---|---|---|
| 57 mg | 1-Methylpiperazine carboxamide of Bumetanide to evaluate SAR of caboxyl group | 35 mg given 101006 | 3.3 mg | No Significant effect at 10 µM |
| 178 mg | 4-(2-Aminoethyl) thiomorpholine 1,1-dioxide carboxamide of Bumetanide to evaluate SAR of caboxyl group | 50 mg given 101006 | 83.4 mg | 60% activation at 10 µM |
| 200 mg | N-ethylaminemorpholine carboxamide of Bumetanide to evaluate SAR of caboxyl group | 50 mg given 101006 | 107.9 mg | Some agonist trend at 10 µM |

| | 181 mg | 3-Aminomethylpyridine carboxamide of Bumetanide to evaluate SAR of caboxyl group | 50 mg given 101006 | 97.1 mg | 50% block at 10 μM |
| --- | --- | --- | --- | --- | --- |

Registered 050307

| | | Analog of AQP-0011 with CH2 removed and nitrogen moved on pyridine linker for SAR exploration. | | | No Significant effect at 10 μM |
| --- | --- | --- | --- | --- | --- |

| | | Analog of AQP-0011 with CH2 removed and nitrogen moved on pyridine linker for SAR exploration. | | | 80% block at 10 μM but some toxicity observed |
| --- | --- | --- | --- | --- | --- |

| | | |
|---|---|---|
| 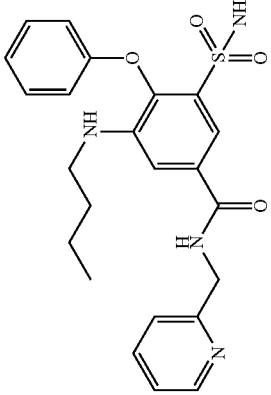 | Analog of AQP-0011, which was a potent blocker in the last round, with nitrogen moved on pyridine ring for SAR exploration. |

| | | | |
|---|---|---|---|
| 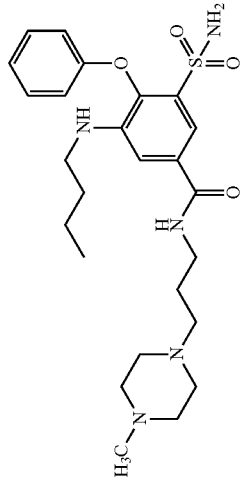 | Analog of AQP-0007, which was a potent stimulator in the last round, with additional carbon in the amide sidechain for SAR exploration | | No Significant effect at 10 μM |
| 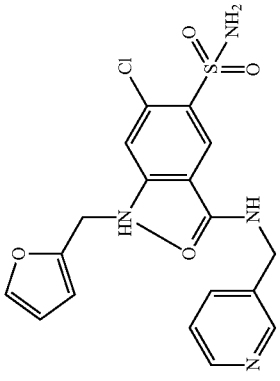 | Prepared to correlate binding mode with bumetanide series. If binding is as bumetanide, this compound should be an channel blocker. If not, then the reverse binding mode is implicated. | 20 mg given 050307 150 mg | No Significant effect at 10 μM |
| 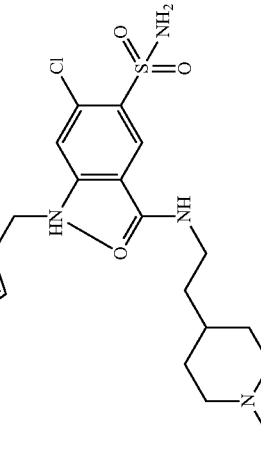 | Prepared to correlate binding mode with bumetanide series. If binding is as bumetanide, this compound should be an stimulator of the channel. If not, then the reverse binding mode is implicated. | 20 mg given 050307 220 mg | No Significant effect at 10 μM |

| | | | | |
|---|---|---|---|---|
| [structure: furfuryl-NH, Cl, SO2NH2, COOCH3 benzene] | 308 mg | Prepared to Improve transport of Furosemide into Oocytes directly or as pro-drug concept. | 10 mg given 083107 Sent in Andrea 090407 | 213 mg | ↓↓ | = |
| [structure: furfuryl-NH, Cl, SO2NHCH3, COOCH3 benzene] | 229 mg | Prepared to Improve transport of Furosemide into Oocytes directly or as pro-drug concept. | 10 mg given 083107 Sent in Andrea 090407 | 119 mg | ↓↓ | Significant Agonist Effect at 100 μM ↑ |
| [structure: furfuryl-NH, Cl, SO2NHCH3, COOH benzene] | 80.5 mg | Prepared to Improve transport of Furosemide into Oocytes directly. | 10 mg given 083107 Sent in Andrea 090407 | 70.5 mg | ↑ | (↑)? |

-continued

| Structure | | Purpose | | Result |
|---|---|---|---|---|
| (furosemide structure) | | To compare the activity with the other Furosemide derivatives | 10 mg given 083107 Sent in Andrea 090407 | = ? ↑ |
| (benzyl sulfonamide structure) | 177 mg | Prepared to Improve transport of Furosemide into Oocytes directly. | 10 mg Sent to Andrea Yool 091207 75 mg | = Significant Agonist Effect at 100 μM ↑ |
| (allyl sulfonamide structure) | 172 mg | Prepared to Improve transport of Furosemide into Oocytes directly. | 10 mg Sent to Andrea Yool 091207 78 mg | = $p > 0.05$ No significant Antagonist Effect at 100 μM (↑)? |

| | | | | | |
|---|---|---|---|---|---|
| 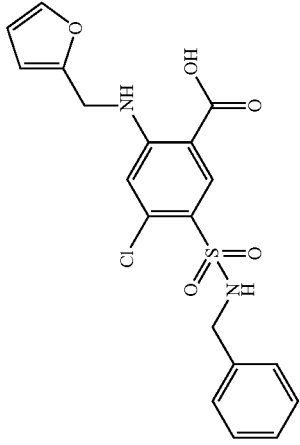 | 63 mg | Prepared to Improve transport of Furosemide into Oocytes directly. | 10 mg Sent to Andrea Yool 091207 | 47 mg | → | = |
| 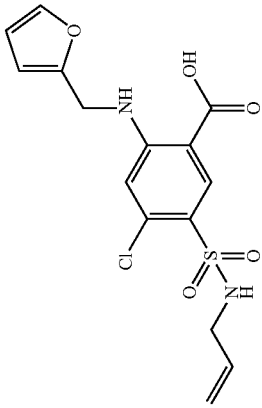 | 55 mg | Prepared to Improve transport of Furosemide into Oocytes directly. | 10 mg Sent to Andrea Yool 091207 | 38 mg | = | Significant Agonist Effect at 100 μM ↑↑ |
| 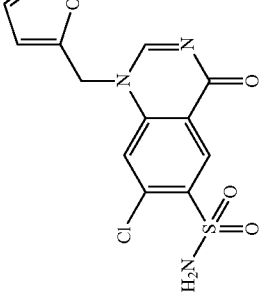 | 167 mg | Prepared to test importance of carboxyl group | 10 mg Sent to Andrea Yool 091207 | 157 mg | → | $p > 0.05$ No significant Antagonist Effect at 100 μM |

| | | | | |
|---|---|---|---|---|
| 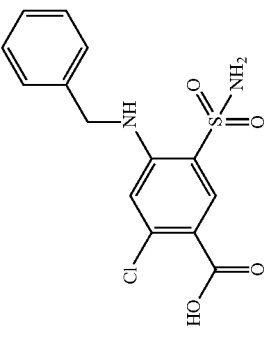 | 102 mg | Prepared to test the importance of the substitution pattern on furosemide | 12 mg Sent to Andrea Yool 100507 | 90 mg | p > 0.05 No significant Antagonist Effect at 100 μM |
| 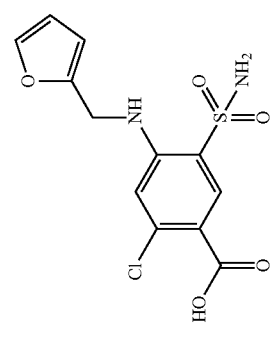 | 15 mg | Prepared to test the importance of the substitution pattern on furosemide | 10 mg Sent to Andrea Yool 100507 | 5 mg | Significant Agonist Effect at 100 μM |
| 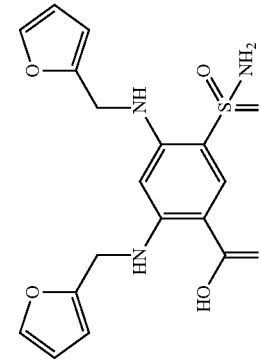 | 10 mg | Prepared to test the importance of the substitution pattern on furosemide | 5 mg Sent to Andrea Yool 100507 | 5 mg | |
| 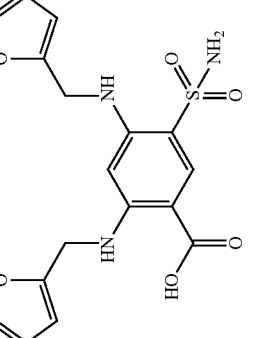 | | Hydrochlorthiazide | 10 mg Sent to Andrea Yool 101607 | | |

-continued

| Methyl ester AQP-0032 for better transport into cells | 10 mg Sent to Andrea Yool -continued
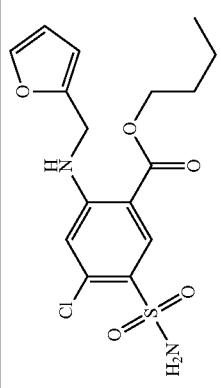
Methyl ester AQP-0032 for better transport into cells
10 mg Sent to Andrea Y Appendix II

| Structure | Reg # | Mol Wt. | ClogP: | tPSA | Comments | AQP-1 effect | AQP-4 effect |
|---|---|---|---|---|---|---|---|
| 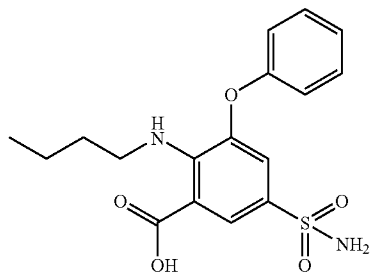 [SMILES: CCCCNc1c(Oc2ccccc2)cc(S(N)(=O)=O)cc1C(=O)O] | Bumetanide AQP-0000 | 330.74 | 1.90 | 140.50 | Marketed loop diuretic | NA | −35% block at 100 μM ↓ |
| 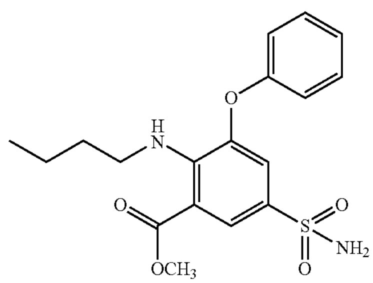 [SMILES: CCCCNc1c(Oc2ccccc2)cc(S(N)(=O)=O)cc1C(=O)OC] | AQP-0001 | 344.77 | 2.10 | 130.80 | | NA | Improved potency over bumetanide −30% block at 1 μM extracellularly ↓↓ |
| 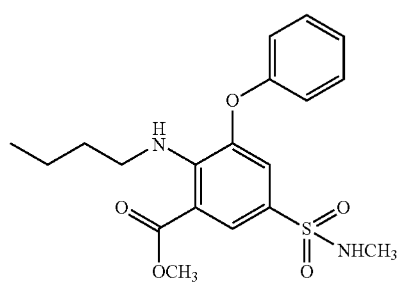 [SMILES: CCCCNc1c(Oc2ccccc2)cc(S(=O)(=O)NC)cc1C(=O)OC] | AQP-0002 | 358.80 | 2.89 | 120.70 | | NA | Improved potency over bumetanide −40% block at 10 μM extracellularly ↓↓ |
| 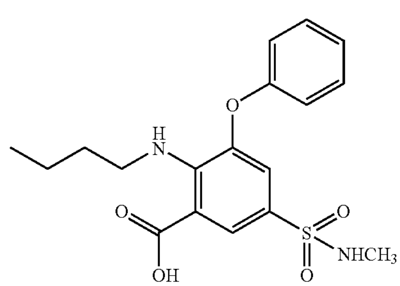 [SMILES: CCCCNc1c(Oc2ccccc2)cc(S(=O)(=O)NC)cc1C(=O)O] | AQP-0003 | 344.77 | 2.75 | 130.40 | | NA | Improved block −40% at 100 μM extracellularly ↓↓ |
| 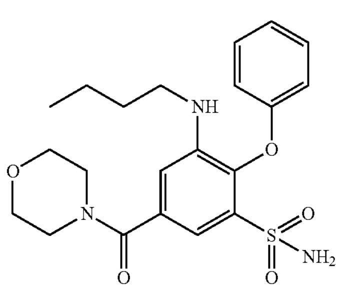 [SMILES: CCCCNc1cc(C(=O)N2CCOCC2)cc(S(N)(=O)=O)c1Oc1ccccc1] | AQP-0006 | 413.88 | 1.04 | 123.40 | | NA | 70% Activation at 10 μM given extracellularly ↑ |

-continued

| Structure | Reg # | Mol Wt. | ClogP: | tPSA | Comments | AQP-1 effect | AQP-4 effect |
|---|---|---|---|---|---|---|---|
| 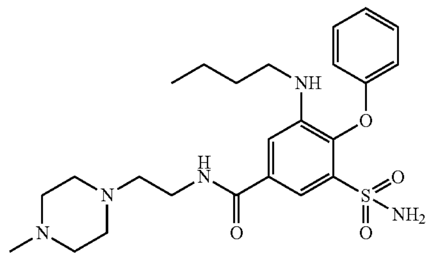 [SMILES: CCCCNc1cc(C(=O)NCCN2CCN(C)CC2)cc(S(N)(=O)=O)c1Oc1ccccc1] | AQP-0007 | 469.99 | 0.79 | 124.80 | | NA | 110% activation at 10 μM given extracellularly ↑↑ |
| 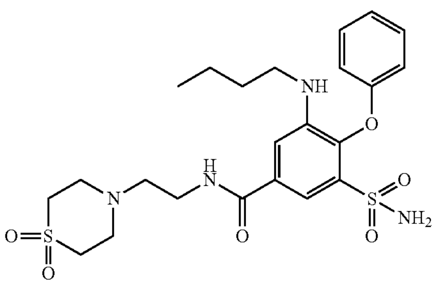 [SMILES: CCCCNc1cc(C(=O)NCCN2CCS(=O)(=O)CC2)cc(S(N)(=O)=O)c1Oc1ccccc1] | AQP-0009 | 505.01 | 0.76 | 166.70 | | NA | 60% activation at 10 μM given extracellularly ↑ |
| 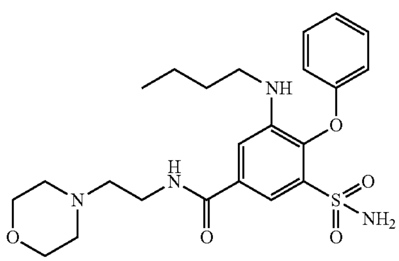 [SMILES: CCCCNc1cc(C(=O)NCCN2CCOCC2)cc(S(N)(=O)=O)c1Oc1ccccc1] | AQP-0010 | 456.94 | 1.75 | 136.20 | | NA | Some agonist trend at 10 μM given extracellularly ↑ |
| 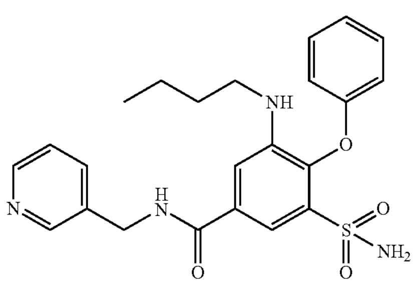 [SMILES: CCCCNc1cc(C(=O)NCc2cccnc2)cc(S(N)(=O)=O)c1Oc1ccccc1] | AQP-0011 | 434.90 | 1.80 | 130.70 | | NA | 50% block at 10 μM given extracellularly ↓↓ |
| 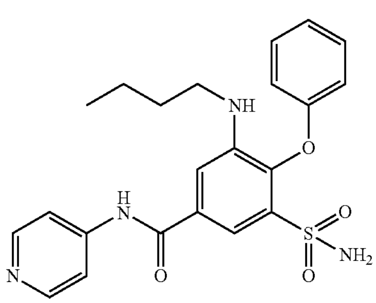 [SMILES: CCCCNc1cc(C(=O)Nc2ccncc2)cc(S(N)(=O)=O)c1Oc1ccccc1] | AQP-0013 | 420.87 | 2.40 | 130.7 | | NA | 80% block at 10 μM given extracellularly ↓↓ |

-continued

| Structure | Reg # | Mol Wt. | ClogP: | tPSA | Comments | AQP-1 effect | AQP-4 effect |
| --- | --- | --- | --- | --- | --- | --- | --- |
| Furosemide | | 330.74 | 1.90 | 140.50 | Marketed loop diuretic | = | Modest effect at 100 μM extracellularly 75% block at 15 μM given intracellularly ↓↓ |
| 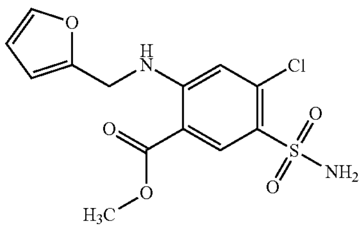 [SMILES: COC(=O)c1cc(S(N)(=O)=O)c(Cl)cc1NCc1ccco1] | AQP-0022 | 344.77 | 2.19 | 130.80 | Furosemide Prodrug | ↓↓ | p > 0.05 No significant effect at 100 μM given extracellularly = |
| 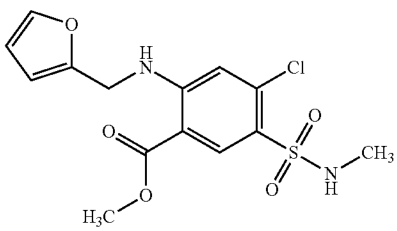 [SMILES: CNS(=O)(=O)c1cc(C(=O)OC)c(NCc2ccco2)cc1Cl] | AQP-0023 | 358.80 | 2.89 | 120.70 | | ↓↓ | Significant Agonist Effect −20% at 100 μM given extracellularly ↑ |
| 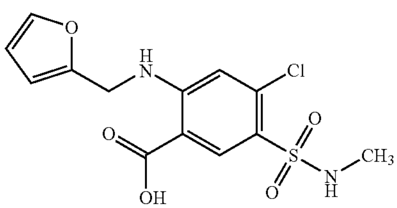 [SMILES: CNS(=O)(=O)c1cc(C(=O)O)c(NCc2ccco2)cc1Cl] | AQP-0042 | 344.77 | 2.75 | 130.40 | | ↑ | p > 0.05 Agonist trend −15% at 100 μM given extracellularly (↑)? |
| 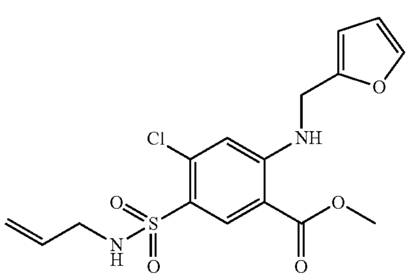 [SMILES: C=CCNS(=O)(=O)c1cc(C(=O)OC)c(NCc2ccco2)cc1Cl] | AQP-0027 | 384.83 | 3.67 | 120.70 | | p > 0.05 No significant effect when given extracellularly = | p > 0.05 Antagonist trend −25% at 100 μM (↓)? |
| 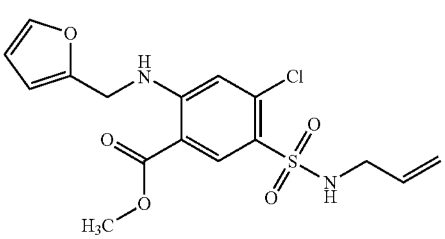 [SMILES: C=CCNS(=O)(=O)c1cc(C(=O)OC)c(NCc2ccco2)cc1Cl] | AQP-0029 | 370.81 | 3.52 | 130.40 | | p > 0.05 No significant effect when given extracellularly = | Significant −40% Agonist Effect at 100 μM ↑↑ |

-continued

| Structure | Reg # | Mol Wt. | ClogP: | tPSA | Comments | AQP-1 effect | AQP-4 effect |
|---|---|---|---|---|---|---|---|
| 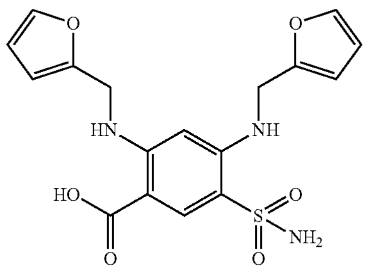 [SMILES: NS(=O)(=O)c1cc(C(=O)O)c(NCc2ccco2)cc1NCc1ccco1] | AQP-0033 | 391.40 | 1.61 | 167.40 | | p > 0.05 No significant effect when given extracellularly = | Significant −25% Agonist Effect at 100 μM ↑ |

Appendix III

| Structure | Reg # | Mol Wt. | ClogP: | tPSA | Comments | AQP-1 effect | AQP-4 effect |
|---|---|---|---|---|---|---|---|
| 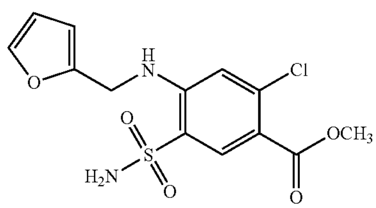 [SMILES: COC(=O)c1cc(S(N)(=O)=O)c(NCc2ccco2)cc1Cl] | AQP-0035 | 344.77 | 1.55 | 130.80 | | NA | NA |
| 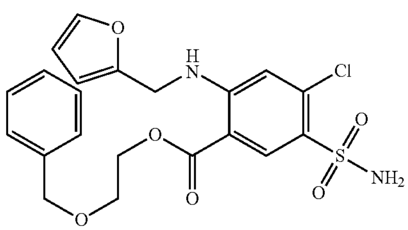 [SMILES: NS(=O)(=O)c1cc(C(=O)OCCOCc2ccccc2)c(NCc2ccco2)cc1Cl] | AQP-0036 | 464.92 | 3.80 | 144.90 | Furosemide Prodrug | NA | NA |
| 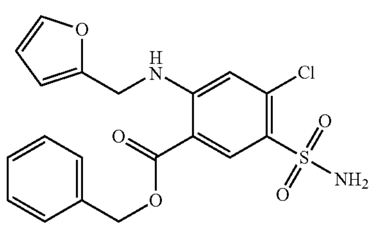 [SMILES: NS(=O)(=O)c1cc(C(=O)OCc2ccccc2)c(NCc2ccco2)cc1Cl] | AQP-0037 | 420.87 | 4.02 | 130.80 | Furosemide Prodrug | NA | NA |
| 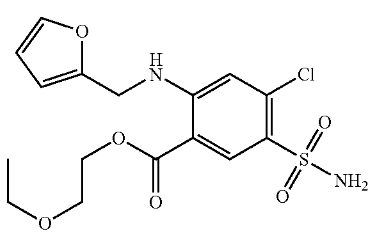 [SMILES: CCOCCOC(=O)c1cc(S(N)(=O)=O)c(Cl)cc1NCc1ccco1] | AQP-0038 | 402.85 | 2.46 | 144.90 | Furosemide Prodrug | NA | NA |
| 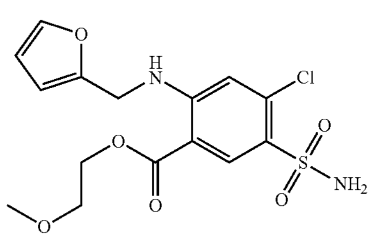 [SMILES: COCCOC(=O)c1cc(S(N)(=O)=O)c(Cl)cc1NCc1ccco1] | AQP-0039 | 386.85 | 3.78 | 130.80 | Furosemide Prodrug | NA | NA |

-continued

| Structure | Reg # | Mol Wt. | ClogP: | tPSA | Comments | AQP-1 effect | AQP-4 effect |
|---|---|---|---|---|---|---|---|
| 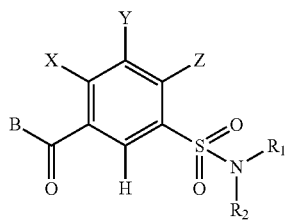 | AQP-0041 | 444.89 | 3.03 | 167.20 | Furosemide Prodrug | NA | NA |
| 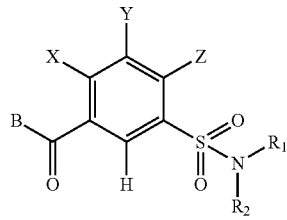 | AQP-0042 | 358.80 | 2.72 | 130.80 | Furosemide Prodrug | NA | NA |

The invention claimed is:

1. A composition comprising a compound of Formula I,

Formula (I)

[Formula I structure]

or a pharmaceutically acceptable salt thereof;
  wherein when B is —OCH$_3$ and X is:

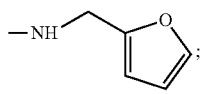

Y is hydrogen;
  Z is chloro;
  R$_1$ is hydrogen, and R$_2$ is benzyl, methyl or —CH$_2$—CH=CH$_2$; or
  when B is —OCH$_3$ and X is —NH—(CH$_2$)$_3$—CH$_3$;
  Y is —O-phenyl;
  Z is hydrogen;
  R$_1$ and R$_2$ are both hydrogen or R$_1$ is hydrogen and R$_2$ is methyl,
  and a prodrug thereof,
  and a pharmacologically acceptable diluent, carrier or expedient.

2. A composition comprising a compound Formula I

Formula (I)

[Formula I structure]

or a pharmaceutically acceptable salt thereof
  wherein when B is —OH;
  X is —NH—(CH$_2$)$_3$—CH$_3$;
  Y is —O-phenyl;
  Z is hydrogen;
  R$_1$ is hydrogen and
  R$_2$ is methyl; or
  when B is a ring structure selected from:

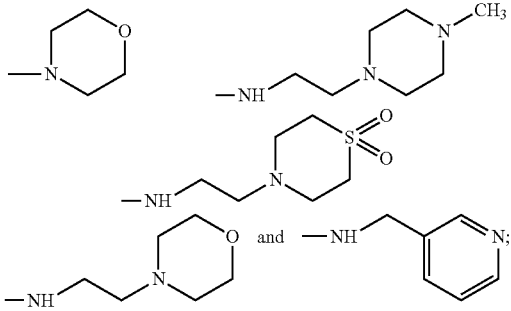

X is hydrogen;
  Y is —NH—(CH$_2$)$_3$—CH$_3$;
  Z is —O-phenyl; and R$_1$ and R$_2$ are both hydrogen,
  and a prodrug thereof,
  and a pharmaceutically acceptable diluent, carrier or expedient.

3. The composition of claim 2, wherein B is
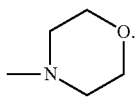
4. A composition comprising a compound of Formula I
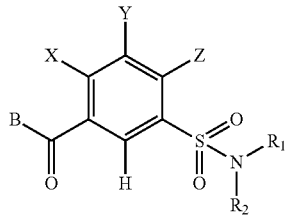
Formula (I)
or a pharmaceutically acceptable salt thereof;
wherein when B is —OH;
X is:
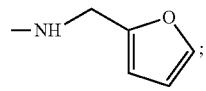
Y is hydrogen;
Z is chloro;
$R_1$ is hydrogen and
$R_2$ is —$CH_2$—CH=$CH_2$,
and a prodrug thereof,
and a pharmaceutically acceptable diluent, carrier or expedient.
* * * * *